US011371048B2

(12) United States Patent
McClain et al.

(10) Patent No.: US 11,371,048 B2
(45) Date of Patent: *Jun. 28, 2022

(54) VECTORS FOR USE IN AN INDUCIBLE COEXPRESSION SYSTEM

(71) Applicant: AbSci, LLC, Portland, OR (US)

(72) Inventors: Sean McClain, Portland, OR (US);
Mark Valasek, San Diego, CA (US);
Philip Barish, Portland, OR (US);
Jeremy Minshull, Newark, CA (US)

(73) Assignee: ABSCI LLC, Vancouver, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/261,984

(22) Filed: Sep. 11, 2016

(65) Prior Publication Data

US 2016/0376602 A1    Dec. 29, 2016

Related U.S. Application Data

(63) Continuation of application No. 14/740,475, filed on Jun. 16, 2015, now abandoned, which is a continuation-in-part of application No. 14/419,653, filed as application No. PCT/US2013/053562 on Aug. 5, 2013, now Pat. No. 9,617,335, said application No. 14/740,475 is a continuation-in-part of application No. PCT/US2014/014968, filed on Feb. 5, 2014, which is a continuation-in-part of application No. PCT/US2013/053562, filed on Aug. 5, 2013.

(60) Provisional application No. 61/747,246, filed on Dec. 29, 2012, provisional application No. 61/679,751, filed on Aug. 5, 2012, provisional application No. 61/747,246, filed on Dec. 29, 2012, provisional application No. 61/679,751, filed on Aug. 5, 2012.

(51) Int. Cl.
*C12N 15/70* (2006.01)
*C07K 16/24* (2006.01)
*C12N 15/63* (2006.01)
*C12P 21/00* (2006.01)

(52) U.S. Cl.
CPC ............ *C12N 15/70* (2013.01); *C07K 16/241* (2013.01); *C12N 15/63* (2013.01); *C12P 21/005* (2013.01); *C07K 2317/24* (2013.01); *C07K 2317/55* (2013.01); *C07K 2317/92* (2013.01); *C12N 2830/002* (2013.01)

(58) Field of Classification Search
CPC .................................................... C12N 15/70
See application file for complete search history.

(56) References Cited

U.S. PATENT DOCUMENTS

| | | | |
|---|---|---|---|
| 6,159,708 A | 12/2000 | Sogo et al. | |
| 6,780,405 B1 | 8/2004 | Curtiss, III et al. | |
| 7,736,851 B2 * | 6/2010 | Stewart | C12N 15/10 435/6.18 |
| 9,617,335 B2 * | 4/2017 | McClain | C07K 16/241 |
| 2006/0246542 A1 * | 11/2006 | Simmons | C07K 16/00 435/69.1 |
| 2009/0203081 A1 * | 8/2009 | Keasling | C12N 15/74 435/91.1 |
| 2009/0305421 A1 * | 12/2009 | Kim | C12N 15/902 435/471 |
| 2010/0255561 A1 | 10/2010 | Steinmetz | |
| 2012/0052542 A1 * | 3/2012 | Marrs | C12P 7/06 435/160 |
| 2014/0120580 A1 | 5/2014 | Simmons et al. | |

FOREIGN PATENT DOCUMENTS

| | | |
|---|---|---|
| EP | 1356052 | 8/2008 |
| EP | 2386641 A1 | 11/2011 |
| WO | WO 02/061090 | 8/2002 |
| WO | 2006133210 A2 | 12/2006 |
| WO | 2011062615 A1 | 5/2011 |
| WO | WO 2014/025663 | 2/2014 |
| WO | 2015020690 A1 | 2/2015 |

OTHER PUBLICATIONS

Bessette et al. (Proc. Natl. Acad. Sci. 96, 24, pp. 13703-13708, 1999) (Year: 1999).*
Faulkner et al., Proc. Natl. Acad. Sci. 105, 18, pp. 6735-6740, 2008). (Year: 2008).*
Li et al. (Ind. J. Clin. Biochem., 25, 3, pp. 319-325, 2010 (Year: 2010).*
Kessler et al. (1969) Arabinose-Leucine Deletion Mutants of *Escherichia coli* B/r. Journal of Bacteriology, 98(3): 1159-1169 (Year: 1969).*
Lee et al. (2006) A Salmonella-based, propionate-inducible, expression system for *Salmonella enterica*. Gene, 377:6-11 (Year: 2006).*
Khlebnikov et al. (2000) Regulatable Arabinose-Inducible Gene Expression System with Consistent Control in All Cells of a Culture. Journal of Bacteriology, 182(24)7029-7034 (Year: 2000).*
Faulkner et al. (2008) Functional plasticity of a peroxidase allows evolution of diverse disulfide-reducing pathways. PNAS, 405(18): 6735-6740 (Year: 2008).*
PCTUS1637942, International Search Report of the International Searching Authority, dated Sep. 23, 2016.
PCTUS1637942, Written Opinion of the International Searching Authority, dated Sep. 23, 2016.
Genbank HO437324.1, "klebsormidium_60434_c1321_c Klebsormidium flaccidum EST library Klebsormidium flaccidum cDNA 5-, mRNA sequence", Jan. 19, 2012, retrieved from the Internet Aug. 28, 2016: <https://www.ncbi.nlm.nih.gov/nucest/HO437324.1>.
Kang et al., "Priority of pentose utilization at the level of transcription: arabinose, xylose, and ribose operons", Mol Cells Jun. 30, 1998; 8(3): 318-323.

(Continued)

*Primary Examiner* — Neil P Hammell
(74) *Attorney, Agent, or Firm* — Marshall, Gerstein & Borun LLP

(57) ABSTRACT

The present invention provides expression vectors for use in an inducible coexpression system, capable of controlled induction of expression of each gene product.

19 Claims, 7 Drawing Sheets

Specification includes a Sequence Listing.

(56) References Cited

OTHER PUBLICATIONS

Lobstein et al., "SHuffle, a novel *Escherichia coli* protein expression strain capable of correctly folding disulfide bonded proteins in its cytoplasm", Microb Cell Fact May 8, 2012; 11: 56; doi: 10.1186/1475-2859-11-56.
Khlebnikov et al., "Homogeneous expression of the P(BAD) promoter in *Escherichia coli* by constitutive expression of the low-affinity high-capacity AraE transporter", Microbiology Dec. 2001; 147(Pt 12): 3241-3247.
Ollis et al., "Cytoplasmic membrane proton motive force energizes periplasmic interactions between ExbD and TonB", Mol Microbiol Aug. 2009; 73(3): 466-481; doi: 10.111/j.1365-2958.2009.06785.x; Epub Jul. 16, 2009.
Mayer, "A new set of useful cloning and expression vectors derived from pBlueScript", Gene Sep. 22, 1995; 163(1): 41-46.
ISA/US, PCT/US2016/037942 International Search Report and Written Opinion of the International Searching Authority, dated Sep. 23, 2016.
GenBank Submission HO437324.1, "klebsormidium_60434_c1321_c Klebsormidium flaccidum EST library <Klebsormidium flaccidum cDNA 5-, mRNA sequence", Jan. 19, 2012.
European Patent Office, Supplementary European Search Report in EP16812476; dated Dec. 7, 2018.
Kim et al., "Two-promoter vector is highly efficient for overproduction of protein complexes" Protein Sci Jun. 2004; 13 (6): 1698-7103; Epub May 7, 2004.
Humphreys et al., "A plasmid system for optimization of Fab' production in *Escherichia coli*: importance of balance of heavy chain and light chain synthesis", Protein Expr Purif Nov. 2002; 26(2): 309-320.

McNally et al., "Coexpression and assembly of myosin heavy chain and myosin light chain in *Escherichia coli*", Proc Natl Acad Sci U S A Oct. 1988; 85(19): 7270-7273.
European Patent Office, Search Opinion in EP16812476; dated Dec. 7, 2018.
ABSCI LLC, Applicant's Response to Search Opinion in EP1681247; dated Jul. 10, 2019.
Canadian IP Office, Examination Report in CA2880285; dated Nov. 15, 2019.
The Patent Office of the People's Republic of China, Office Action in CN201380041522X; dated Nov. 26, 2019.
The Patent Office of the People's Republic of China, Office Action in CN201380041522X, English Translation dated Nov. 26, 2019.
Samuelson et al., "Recent developments in difficult protein expression: a guide to *E. coli* strains, promoters, and relevant host mutations", Methods Mol Biol 2011; 705:195-209; Review.
USPTO, Non-Final Office Action in U.S. Appl. No. 14/909,707; dated Apr. 26, 2018.
USPTO, Final Office Action in U.S. Appl. No. 14/909,707; dated Nov. 8, 2018.
IP Australia, Examination Report in AU2013299910; dated Mar. 28, 2018.
Canadian IP Office, Examination Report in CA2880285; dated Jan. 15, 2019.
European Patent Office, Search Opinion in EP16201998; dated May 3, 2017.
Japan Patent Office, First Notification of Reasons for Refusal in JP 2015526598; dated Jun. 22, 2017.
Japan Patent Office, Second Notification of Reasons for Refusal in JP 2015526598; dated Jan. 30, 2018.
CIPO, Office Action in CN201380041522X; dated May 10, 2019.
CIPO, Office Action in CN201380041522X, English Translation; May 10, 2019.

* cited by examiner

VECTORS FOR USE IN AN INDUCIBLE COEXPRESSION SYSTEM

REFERENCE TO RELATED APPLICATIONS

This application is a continuation of U.S. application Ser. No. 14/740,475, filed 16 Jun. 2015, which is a continuation-in-part of U.S. application Ser. No. 14/419,653, which is a national-stage entry under 35 U.S.C. § 371 of International Application No. PCT/US2013/053562 filed 5 Aug. 2013, which claims the benefit of priority under 35 U.S.C. § 119(e) of U.S. Provisional Application No. 61/679,751, filed 5 Aug. 2012, and of U.S. Provisional Application No. 61/747,246, filed 29 Dec. 2012, the entire disclosures of all of which are incorporated by reference herein.

This application is a continuation of U.S. application Ser. No. 14/740,475, filed 16 Jun. 2015, which is also a continuation-in-part of International Application No. PCT/US2014/014968 filed 5 Feb. 2014, which claims the priority of International Application No. PCT/US2013/053562 filed 5 Aug. 2013, which claims the benefit of priority under 35 U.S.C. § 119(e) of U.S. Provisional Application No. 61/679,751, filed 5 Aug. 2012, and of U.S. Provisional Application No. 61/747,246, filed 29 Dec. 2012, the entire disclosures of all of which are incorporated by reference herein.

REFERENCE TO THE SEQUENCE LISTING

This application includes a sequence listing submitted electronically, in a file entitled "AbSci001CIP1_ST25.txt", created on May 26, 2015 and having a size of 82 kilobytes (KB), which is incorporated by reference herein.

FIELD OF THE INVENTION

The present invention is in the general technical fields of molecular biology and biotechnological manufacturing. More particularly, the present invention is in the technical field of recombinant protein expression.

BACKGROUND OF THE INVENTION

Production of biotechnological substances is a complex process, even more so when the desired product is a combination of molecules encoded by different genes, such as a multimeric protein formed from two or more different polypeptides. Successful coexpression of multiple gene products requires overcoming a number of challenges, which are compounded by the simultaneous expression of more than one gene product. Problems that must be overcome include creating compatible expression vectors when more than one type of vector is used; obtaining the correct stoichiometric ratio of products; producing gene products that are folded correctly and in the proper conformation with respect to binding partners; purifying the desired products away from cells and unwanted proteins, such as proteins that are folded incorrectly and/or are in an incorrect conformation; and minimizing the formation of inclusion bodies, as one aspect of maximizing the yield of the desired product(s). Many different approaches have been taken to address these challenges, but there is still a need for better coexpression methods.

Several inducible bacterial protein expression systems, including plasmids containing the lac and ara promoters, have been devised to express individual proteins. These systems have limited utility in the coexpression of difficult-to-express proteins as they fail to induce protein homogenously within the entire growth culture population in wild-type *E. coli* (Khlebnikov and Keasling, "Effect of lacY expression on homogeneity of induction from the $P_{tac}$ and $P_{trc}$ promoters by natural and synthetic inducers", Biotechnol Prog 2002 May-June; 18(3): 672-674). When expression of the transport proteins for inducers is dependent on the presence of inducer, as is the case for wild-type *E. coli* lac and ara systems, the cellular concentration of the inducer must reach a threshold level to initiate the production of transport proteins, but once that threshold has been reached, an uncontrolled positive feedback loop can occur, with the result being a high level of inducer in the cell and correspondingly high levels of expression from inducible promoters: the "all-or-none" phenomenon. Increasing the concentration of the inducer in the growth medium increases the proportion of cells in the population that are in high-expression mode. Although this type of system results in concentration-dependent induction of protein expression at the population scale, it is suboptimal for expression and production of proteins that require tight control of expression, including those that are toxic, have poor solubility, or require specific concentrations for other reasons.

Some efforts have been made to address the "all-or-none" induction phenomenon in single-promoter expression systems, by eliminating inducer-dependent transport of the inducer. One example is having a null mutation in the lactose permease gene (lacYam) and using an alternate inducer of the lac promoter such as IPTG (isopropyl-thio-β-D-galactoside), which can get through the cell membrane to some degree in the absence of a transporter (Jensen et al., "The use of lac-type promoters in control analysis", Eur J Biochem 1993 Jan. 15; 211(1-2): 181-191). Another approach is the use of an arabinose-inducible promoter in a strain deficient in the arabinose transporter genes, but with a mutation in the lactose permease gene, lacY(A117C), that allows it to transport arabinose into the cell (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377).

The components of individual protein expression systems are often incompatible, precluding their use in coexpression systems, as they may be adversely affected by 'crosstalk' effects between different inducer-promoter systems, or require mutually exclusive genomic modifications, or be subject to general metabolic regulation. An attempt to address the 'crosstalk' problem between the lac and ara inducible promoter systems included directed evolution of the AraC transcriptional activator to improve its ability to induce the araBAD promoter in the presence of IPTG, an inducer of the lac promoter (Lee et al., "Directed evolution of AraC for improved compatibility of arabinose- and lactose-inducible promoters", Appl Environ Microbiol 2007 September; 73(18): 5711-5715; Epub 2007 Jul. 20). However, the compatibility between expression vectors based on ara and lac inducible promoters is still limited due to the requirement for mutually exclusive genomic modifications: a lacY point mutation (lacY(A117C)) for homogenous induction of the araBAD promoter by arabinose, and a null lacY gene for homogenous induction of the lac promoter by IPTG. General metabolic regulation—for example, carbon catabolite repression (CCR)—can also affect the compatibility of inducible promoters. CCR is characterized by the repression of genes needed for utilization of a carbon-containing compound when a more preferred compound is present, as seen in the preferential use of glucose before other sugars. In the case of the ara and prp inducible promoter systems, the presence of arabinose reduces the ability of propionate to induce expression from the prpBCDE promoter, an effect believed to involve CCR (Park et al., "The mechanism of sugar-mediated catabolite repression of the propionate catabolic genes in *Escherichia coli*", Gene 2012 Aug. 1; 504(1): 116-121, Epub 2012 May 3). There is clearly a need for an inducible coexpression system that overcomes these problems.

SUMMARY OF THE INVENTION

The present invention provides expression constructs for use in inducible coexpression systems capable of controlled induction of each gene product component. One embodiment of the invention is an expression construct comprising two or more inducible promoters, wherein at least one of said inducible promoters is responsive to an inducer that is different than the inducer of another of said inducible promoters, and wherein none of the inducible promoters is an inducible promoter selected from the group consisting of: a tetracycline-inducible promoter, a copper-inducible promoter, and a methionine-inducible promoter. In some embodiments, the above expression construct does not comprise a lactose-inducible promoter, and in certain embodiments, the above expression construct does not comprise a promoter inducible by phosphate depletion. In additional embodiments, the expression construct is extrachromosomal. Further embodiments of the invention provide expression constructs comprising two or more inducible promoters, wherein at least one of said inducible promoters is responsive to an inducer that is different than the inducer of another of said inducible promoters, and (A) wherein each inducible promoter is selected from the group consisting of an L-arabinose-inducible promoter, a propionate-inducible promoter, a rhamnose-inducible promoter, a xylose-inducible promoter, a lactose-inducible promoter, and a promoter inducible by phosphate depletion; or (B) wherein at least one inducible promoter is selected from the group consisting of the araBAD promoter, the prpBCDE promoter, the rhaSR promoter, the xlyA promoter, the lacZYA promoter, and the phoA promoter; or (C) wherein the expression construct comprises at least one propionate-inducible promoter, which in some embodiments is the prpBCDE promoter, and at least one inducible promoter selected from the group consisting of an L-arabinose-inducible promoter, a rhamnose-inducible promoter, a xylose-inducible promoter, a lactose-inducible promoter, and a promoter inducible by phosphate depletion; or (D) wherein the expression construct comprises at least one L-arabinose-inducible promoter, which in some embodiments is the araBAD promoter, and at least one inducible promoter selected from the group consisting of a propionate-inducible promoter, a rhamnose-inducible promoter, a xylose-inducible promoter, a lactose-inducible promoter, and a promoter inducible by phosphate depletion; or (E) wherein at least one inducible promoter is a propionate-inducible promoter and at least one other inducible promoter is an L-arabinose-inducible promoter; or (F) wherein the expression construct comprises a nucleotide sequence having at least 80% (or at least 90%, or at least 95%) sequence identity to at least 50 (or at least 75, or at least 100) contiguous bases of nucleotides 4937 through 5185 of SEQ ID NO:15; or (G) wherein the expression construct comprises a nucleotide sequence having at least 80% (or at least 90%, or at least 95%) sequence identity to at least 50 (or at least 75, or at least 100) contiguous bases of nucleotides 2818 through 3151 of SEQ ID NO:15; or (H) wherein the expression construct comprises a nucleotide sequence having at least 80% (or at least 90%, or at least 95%) sequence identity to at least 50 (or at least 75, or at least 100) contiguous bases of nucleotides 2818 through 3151 of SEQ ID NO:15, and at least 80% (or at least 90%, or at least 95%) sequence identity to at least 50 (or at least 75, or at least 100) contiguous bases of nucleotides 4937 through 5185 of SEQ ID NO:15; or (I) wherein the expression construct comprises a nucleotide sequence having at least 80% (or at least 90%, or at least 95%) sequence identity to at least 3000 (or at least 3250) contiguous bases of nucleotides 1833 through 5304 of SEQ ID NO:15; or (J) wherein the expression construct comprises a nucleotide sequence having at least 80% (or at least 90%, or at least 95%) sequence identity to at least 5000 contiguous bases of SEQ ID NO:15; or (K) wherein the expression construct comprises nucleotides 1833 through 5304 of SEQ ID NO:15; or (L) wherein the expression construct comprises SEQ ID NO:15; or (M) wherein the expression construct further comprises a polynucleotide sequence encoding a transcriptional regulator that binds to an inducible promoter, wherein in some embodiments, the transcriptional regulator is selected from the group consisting of: AraC, PrpR, RhaR, and XylR; or (N) wherein the expression construct further comprises at least one polynucleotide sequence encoding at least one gene product to be transcribed from an inducible promoter.

Also provided by the invention is an expression construct comprising a nucleotide sequence selected from the group consisting of: (a) a nucleotide sequence having at least 97% sequence identity to at least 225 (or at least 240) contiguous bases of nucleotides 4937 through 5185 of SEQ ID NO:15; (b) a nucleotide sequence having at least 80% (or at least 90%, or at least 95%) sequence identity to at least 300 (or at least 350) contiguous bases of nucleotides 4937 through 5304 of SEQ ID NO:15; (c) a nucleotide sequence having at least 87% (or at least 90%, or at least 95%) sequence identity to at least 350 (or at least 375, or at least 400, or at least 425) contiguous bases of nucleotides 2818 through 3259 of SEQ ID NO:15; (d) a nucleotide sequence having at least 90% (or at least 95%) sequence identity to at least 400 (or at least 450, or at least 500) contiguous bases of nucleotides 10 through 1822 of SEQ ID NO:2; (e) nucleotides 2818 through 3259 of SEQ ID NO:15; (f) nucleotides 4937 through 5185 of SEQ ID NO:15; (g) nucleotides 2818 through 3259 of SEQ ID NO:15 and nucleotides 4937 through 5185 of SEQ ID NO:15; (h) nucleotides 10 through 1822 of SEQ ID NO:2; and (i) a nucleotide sequence selected from the group consisting of SEQ ID NO:2, SEQ ID NO:4, SEQ ID NO:5, SEQ ID NO:6, SEQ ID NO:7, SEQ ID NO:8, and SEQ ID NO:15. In certain embodiments of the invention, the above expression construct comprises an inducible promoter selected from the group consisting of an L-arabinose-inducible promoter, which in some embodiments is the araBAD promoter; a propionate-inducible promoter, which in some embodiments is the prpBCDE promoter; a rhamnose-inducible promoter, which in some embodiments is the rhaSR promoter; a xylose-inducible promoter, which in some embodiments is the xlyA promoter; a lactose-inducible promoter, which in some embodiments is the lacZYA promoter; and a promoter inducible by phosphate depletion, which in some embodiments is the phoA promoter; and in some embodiments, the above expression construct further comprises at least one polynucleotide sequence encoding at least one gene product to be transcribed from an inducible promoter.

In additional embodiments of the invention, an expression construct is produced by a method comprising a step of inserting a polynucleotide sequence into a plasmid selected from the group consisting of: pBAD240, pPRO43, pPRO44, pPRO45, pPRO430, pPRO430CloDF, and pSOL.

The present invention further provides a host cell comprising at least one expression construct of the invention as described in the above paragraphs, comprising at least one inducible promoter. In some embodiments of the invention, this host cell is a prokaryotic cell, and in some instances, it is an *E. coli* cell, which in certain embodiments is an *E. coli* ASE(DGH) cell. In other embodiments of the invention, the host cell is a eukaryotic cell, and in some instances it is a yeast cell, and in some further instances it is a *Saccharomyces cerevisiae* cell. Also provided by the invention is a host cell further comprising one or more of the following: (a) a deletion of the araBAD genes; (b) an altered gene function of the araE and araFGH genes; (c) a lacY(A177C) gene; (d) a reduced gene function of the prpB and prpD genes; (e) a reduced gene function of the sbm/scpA-ygfD/argK-ygfGH/scpBC genes; (f) a reduced gene function of the gor and trxB genes; (g) a reduced gene function of the AscG gene; (h) a polynucleotide encoding a form of DsbC lacking a signal peptide; (i) a polynucleotide encoding Erv1p; and (j) a polynucleotide encoding a chaperone. In certain additional embodiments, (A) the host cell has an alteration of gene function of at least one gene encoding a transporter protein for an inducer of at least one inducible promoter, and as another example, wherein the gene encoding the transporter protein is selected from the group consisting of araE, araF, araG, araH, rhaT, xylF, xylG, and xylH, or particularly is araE, or wherein the alteration of gene function more particularly is expression of araE from a constitutive promoter; (B) the host cell has a reduced level of gene function of at least one gene encoding a protein that metabolizes an inducer of at least one inducible promoter, and as further examples, wherein the gene encoding a protein that metabolizes an inducer of at least one said inducible promoter is selected from the group consisting of araA, araB, araD, prpB, prpD, rhaA, rhaB, rhaD, xylA, and xylB; and/or (C) the host cell has a reduced level of gene function of at least one gene encoding a protein involved in biosynthesis of an inducer of at least one inducible promoter, which gene in further embodiments is selected from the group consisting of scpA/sbm, argK/ygfD, scpB/ygfG, scpC/ygfH, rmlA, rmlB, rmlC, and rmlD.

In other aspects of the invention, a host cell is provided comprising two or more types of expression constructs, wherein the expression construct of each type comprises an inducible promoter, wherein the expression construct of each type comprises an inducible promoter that is not an inducible promoter of the expression construct of each other type, or wherein the expression construct of each type comprises an origin of replication that is different from the origin of replication of the expression construct of each other type.

In additional embodiments of the invention, at least one expression construct comprised by a host cell further comprises a polynucleotide sequence encoding a transcriptional regulator that binds to an inducible promoter; in some embodiments, the polynucleotide sequence encoding a transcriptional regulator and the inducible promoter to which said transcriptional regulator binds are in the same expression construct; and in further instances, the transcriptional regulator is selected from the group consisting of: AraC, PrpR, RhaR, and XylR; or in particular is AraC, or is PrpR.

A host cell is also provided by the invention, comprising at least one expression construct as described in the above paragraphs, which comprises at least one inducible promoter, wherein the at least one expression construct further comprises at least one polynucleotide sequence encoding at least one gene product to be transcribed from an inducible promoter. Other examples of the invention include a host cell comprising at least one expression construct comprising at least one inducible promoter and at least one polynucleotide sequence encoding a gene product to be transcribed from an inducible promoter, wherein in certain embodiments at least one gene product is a polypeptide, or is a polypeptide that lacks a signal sequence, or is a polypeptide that forms at least one and fewer than twenty disulfide bonds, or at least two and fewer than seventeen disulfide bonds, or at least eighteen and fewer than one hundred disulfide bonds, or at least three and fewer than ten disulfide bonds, or at least three and fewer than eight disulfide bonds, or is a polypeptide that forms a number of disulfide bonds selected from the group consisting of one, two, three, four, five, six, seven, eight, and nine, or is an immunoglobulin heavy or light chain or a fragment thereof, or is an infliximab heavy or light chain or a fragment thereof.

Methods of producing gene products are also provided by the invention, such as by growing a culture of a host cell of the invention as described above; and in some embodiments by adding an inducer of at least one inducible promoter to the culture; and in further embodiments by purifying a gene product from the culture. In particular aspects of the invention, the gene product produced by the above method is a polypeptide that forms at least one disulfide bond, or forms at least two and fewer than seventeen disulfide bonds, or forms at least two and fewer than ten disulfide bonds, or forms a number of disulfide bonds selected from the group consisting of one, two, three, four, five, six, seven, eight, and nine, or is an immunoglobulin heavy or light chain or a fragment thereof. The present invention also provides a gene product produced by the above method, wherein the gene product is a polypeptide that lacks a signal peptide, and that in certain embodiments forms at least one disulfide bond, or at least two and fewer than seventeen disulfide bonds, or at least eighteen and fewer than one hundred disulfide bonds, or at least three and fewer than ten disulfide bonds, or at least three and fewer than eight disulfide bonds, or forms a number of disulfide bonds selected from the group consisting of one, two, three, four, five, six, seven, eight, and nine, or is an immunoglobulin heavy or light chain or a fragment thereof. A gene product produced by this method is also provided by the invention, and in some embodiments is part of a multimeric product, which in certain embodiments is an antibody, or in more particular instances, is an aglycosylated antibody, a chimeric antibody, or a human antibody.

Also provided by the systems and methods of the invention are kits comprising an expression construct as described in the above paragraphs; kits comprising a host cell, the host cell comprising at least one expression construct of the invention as described in the above paragraphs; and kits comprising a gene product or a multimeric product produced by growing a host cell of the invention, which in some embodiments includes adding at least one inducer to the culture, where in some embodiments the multimeric product is an antibody, or in more particular instances, is an aglycosylated antibody, a chimeric antibody, or a human antibody.

DETAILED DESCRIPTION OF THE INVENTION

Figure 1:
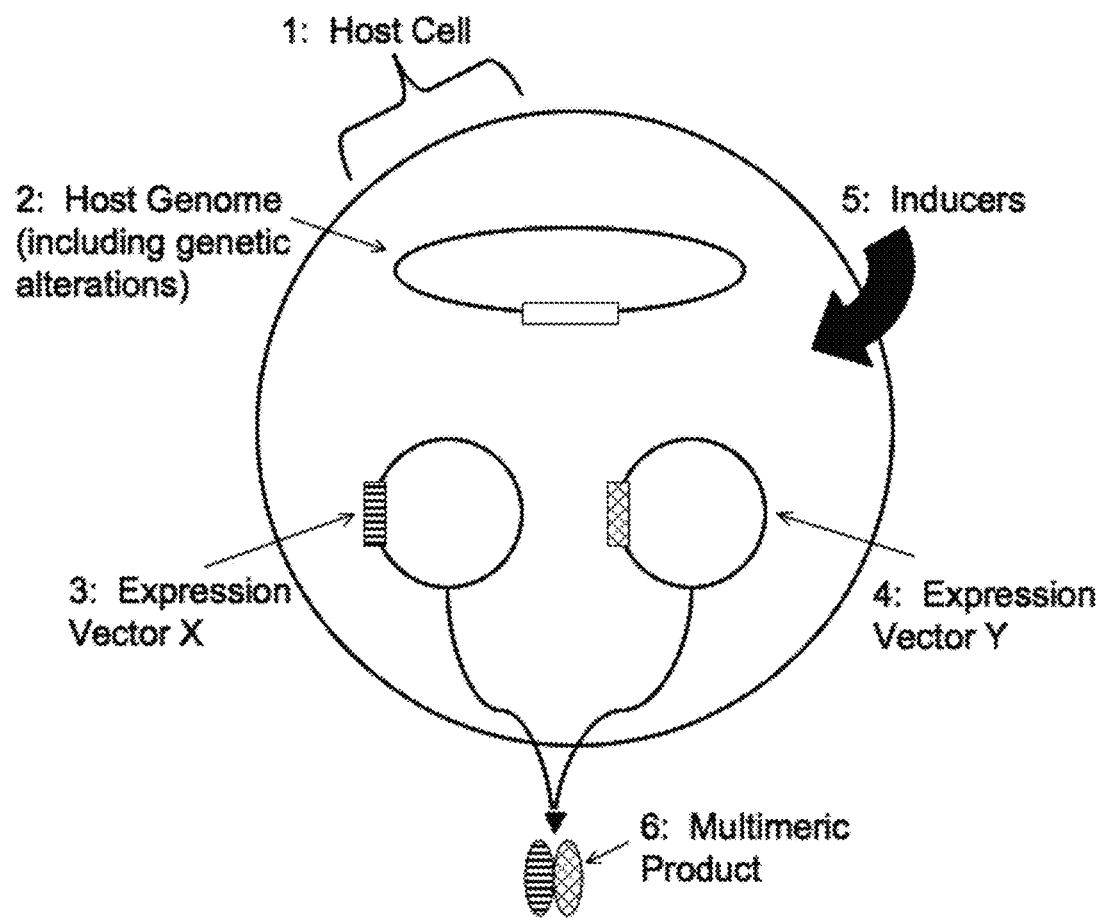
FIG. 1 is a schematic illustration of the inducible coexpression system, which includes a host cell (1) comprising two different inducible expression vectors (3) and (4), which express different gene products upon application of inducers (5), forming a multimeric product (6).

The problem of incompatible coexpression system components is addressed by development of coordinated bacterial coexpression systems which utilize compatible homogenously inducible promoter systems located on separate expression constructs and, in some embodiments, activated by different inducers. The advantages of the present invention include, without limitation: 1) improved compatibility of components within the inducible coexpression system; 2) inducible expression of gene products that together form multimers, or other combinations of gene products (coexpression of two or more gene products); 3) improved control of gene product coexpression by independently titratible induction; 4) improved expression of gene product complexes and other products that are difficult to express such as multimeric products and products forming disulfide bonds; 5) streamlined optimization of gene product coexpression.

Coexpressed Gene Products.

The inducible coexpression systems of the invention are designed to coexpress two or more different gene products that contribute to a desired product. The desired product can be a multimer, formed from coexpressed gene products, or coexpression can be used to produce a combination of the desired product plus an additional product or products that assist in expression of the desired product.

A 'multimeric product' refers to a set of gene products that coassemble to carry out the function of the multimeric product, and does not refer to transitory associations between gene products and other molecules, such as modifying enzymes (kinases, peptidases, and the like), chaperones, transporters, etc. In certain embodiments of the invention, the multimeric products are heteromultimers. In many embodiments, the coexpressed gene products will be polypeptides that are subunits of multimeric proteins. However, it is also possible to use the inducible coexpression systems of the invention to coexpress multiple different non-coding RNA molecules, or a combination of polypeptide and non-coding RNA gene products. Non-coding RNA molecules, also called non-protein-coding RNA (npcRNA), non-messenger RNA (nmRNA), and functional RNA (fRNA), include many different types of RNA molecules such as microRNAs that are not messenger RNAs and thus are not templates for the formation of polypeptides through translation.

Many biologically important products are formed from combinations of different polypeptide chains. In addition to antibodies and antibody fragments, other multimeric products that can be produced by the inducible coexpression methods of the invention include G-coupled protein receptors and ligand-gated ion channels such as nicotinic acetylcholine receptors, $GABA_A$ receptors, glycine receptors, serotonin receptors, glutamate receptors, and ATP-gated receptors such as P2X receptors. The botulinum neurotoxin (often referred to as BoTN, BTX, or as one of its commercially available forms, BOTOX® (onabotulinumtoxinA)) is formed from a heavy chain and a light chain, linked by a disulfide bond (Simpson et al., "The role of the interchain disulfide bond in governing the pharmacological actions of botulinum toxin", J Pharmacol Exp Ther 2004 March; 308(3): 857-864, Epub 2003 Nov. 14). Another example of a product formed from different polypeptide chains is insulin, which in eukaryotes is first translated as a single polypeptide chain, folded, and then cleaved ultimately into two polypeptide chains held together by disulfide bonds. Efficient production of botulinum neurotoxin or of mature insulin in a single host cell are examples of uses of the inducible coexpression methods of the invention.

The methods of the invention are designed to produce gene products that have been correctly folded and/or assembled into functional products, and that have a desired number of disulfide bonds in the desired locations within such functional products (which can be determined by methods such as that of Example 11). The number of disulfide bonds for a gene product such as a polypeptide is the total number of intramolecular and intermolecular bonds formed by that gene product when it is present in a desired functional product. For example, a light chain of a human IgG antibody typically has three disufide bonds (two intramolecular bonds and one intermolecular bond), and a heavy chain of a human IgG antibody typically has seven disufide bonds (four intramolecular bonds and three intermolecular bonds). In some embodiments, desired gene products are coexpressed with other gene products, such as chaperones, that are beneficial to the production of the desired gene product. Chaperones are proteins that assist the non-covalent folding or unfolding, and/or the assembly or disassembly, of other gene products, but do not occur in the resulting monomeric or multimeric gene product structures when the structures are performing their normal biological functions (having completed the processes of folding and/or assembly). Chaperones can be expressed from an inducible promoter or a constitutive promoter within an expression construct, or can be expressed from the host cell chromosome; preferably, expression of chaperone protein(s) in the host cell is at a sufficiently high level to produce coexpressed gene products that are properly folded and/or assembled into the desired product. Examples of chaperones present in *E. coli* host cells are the folding factors DnaK/DnaJ/GrpE, DsbC/DsbG, GroEL/GroES, IbpA/IbpB, Skp, Tig (trigger factor), and FkpA, which have been used to prevent protein aggregation of cytoplasmic or periplasmic proteins. DnaK/DnaJ/GrpE, GroEL/GroES, and ClpB can function synergistically in assisting protein folding and therefore expression of these chaperones in combinations has been shown to be beneficial for protein expression (Makino et al., "Strain engineering for improved expression of recombinant proteins in bacteria", Microb Cell Fact 2011 May 14; 10: 32). When expressing eukaryotic proteins in prokaryotic host cells, a eukaryotic chaperone protein, such as protein disulfide isomerase (PDI) from the same or a related eukaryotic species, is coexpressed or inducibly coexpressed with the desired gene product in certain embodiments of the invention.

Inducible Promoters.

The following is a description of inducible promoters that can be used in expression constructs for coexpression of gene products, along with some of the genetic modifications that can be made to host cells that contain such expression constructs. Examples of these inducible promoters and related genes are, unless otherwise specified, from *Escherichia coli* (*E. coli*) strain MG1655 (American Type Culture Collection deposit ATCC 700926), which is a substrain of *E. coli* K-12 (American Type Culture Collection deposit ATCC 10798). Table 1 lists the genomic locations, in *E. coli* MG1655, of the nucleotide sequences for these examples of inducible promoters and related genes. Nucleotide and other genetic sequences, referenced by genomic location as in Table 1, are expressly incorporated by reference herein. Additional information about *E. coli* promoters, genes, and strains described herein can be found in many public sources, including the online EcoliWiki resource, located at ecoliwiki.net.

Arabinose Promoter.

(As used herein, 'arabinose' means L-arabinose.) Several *E. coli* operons involved in arabinose utilization are inducible by arabinose—araBAD, araC, araE, and araFGH—but the terms 'arabinose promoter' and 'ara promoter' are typically used to designate the araBAD promoter. Several additional terms have been used to indicate the *E. coli* araBAD promoter, such as $P_{ara}$, $P_{araB}$, $P_{araBAD}$, and $P_{BAD}$. The use herein of 'ara promoter' or any of the alternative terms given above, means the *E. coli* araBAD promoter. As can be seen from the use of another term, 'araC-araBAD promoter', the araBAD promoter is considered to be part of a bidirectional promoter, with the araBAD promoter controlling expression of the araBAD operon in one direction, and the araC promoter, in close proximity to and on the opposite strand from the araBAD promoter, controlling expression of the araC coding sequence in the other direction. The AraC protein is both a positive and a negative transcriptional regulator of the araBAD promoter. In the absence of arabinose, the AraC protein represses transcription from $P_{BAD}$, but in the presence of arabinose, the AraC protein, which alters its conformation upon binding arabinose, becomes a positive regulatory element that allows transcription from $P_{BAD}$. The araBAD operon encodes proteins that metabolize L-arabinose by converting it, through the intermediates L-ribulose and L-ribulose-phosphate, to D-xylulose-5-phosphate. For the purpose of maximizing induction of expression from an arabinose-inducible promoter, it is useful to eliminate or reduce the function of AraA, which catalyzes the conversion of L-arabinose to L-ribulose, and optionally to eliminate or reduce the function of at least one of AraB and AraD, as well. Eliminating or reducing the ability of host cells to decrease the effective concentration of arabinose in the cell, by eliminating or reducing the cell's ability to convert arabinose to other sugars, allows more arabinose to be available for induction of the arabinose-inducible promoter. The genes encoding the transporters which move arabinose into the host cell are araE, which encodes the low-affinity L-arabinose proton symporter, and the araFGH operon, which encodes the subunits of an ABC superfamily high-affinity L-arabinose transporter. Other proteins which can transport L-arabinose into the cell are certain mutants of the LacY lactose permease: the LacY(A177C) and the LacY(A177V) proteins, having a cysteine or a valine amino acid instead of alanine at position 177, respectively (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377). In order to achieve homogenous induction of an arabinose-inducible promoter, it is useful to make transport of arabinose into the cell independent of regulation by arabinose. This can be accomplished by eliminating or reducing the activity of the AraFGH transporter proteins and altering the expression of araE so that it is only transcribed from a constitutive promoter. Constitutive expression of araE can be accomplished by eliminating or reducing the function of the native araE gene, and introducing into the cell an expression construct which includes a coding sequence for the AraE protein expressed from a constitutive promoter. Alternatively, in a cell lacking AraFGH function, the promoter controlling expression of the host cell's chromosomal araE gene can be changed from an arabinose-inducible promoter to a constitutive promoter. In similar manner, as additional alternatives for homogenous induction of an arabinose-inducible promoter, a host cell that lacks AraE function can have any functional AraFGH coding sequence present in the cell expressed from a constitutive promoter. As another alternative, it is possible to express both the araE gene and the araFGH operon from constitutive promoters, by replacing the native araE and araFGH promoters with constitutive promoters in the host chromosome. It is also possible to eliminate or reduce the activity of both the AraE and the AraFGH arabinose transporters, and in that situation to use a mutation in the LacY lactose permease that allows this protein to transport arabinose. Since expression of the lacY gene is not normally regulated by arabinose, use of a LacY mutant such as LacY(A177C) or LacY(A177V), will not lead to the 'all or none' induction phenomenon when the arabinose-inducible promoter is induced by the presence of arabinose. Because the LacY(A177C) protein appears to be more effective in transporting arabinose into the cell, use of polynucleotides encoding the LacY(A177C) protein is preferred to the use of polynucleotides encoding the LacY (A177V) protein.

Propionate Promoter.

The 'propionate promoter' or 'prp promoter' is the promoter for the *E. coli* prpBCDE operon, and is also called $P_{prpB}$. Like the ara promoter, the prp promoter is part of a bidirectional promoter, controlling expression of the prpBCDE operon in one direction, and with the prpR promoter controlling expression of the prpR coding sequence in the other direction. The PrpR protein is the transcriptional regulator of the prp promoter, and activates transcription from the prp promoter when the PrpR protein binds 2-methylcitrate ('2-MC'). Propionate (also called propanoate) is the ion, $CH_3CH_2COO^-$, of propionic acid (or 'propanoic acid'), and is the smallest of the 'fatty' acids having the general formula $H(CH_2)_nCOOH$ that shares certain properties of this class of molecules: producing an oily layer when salted out of water and having a soapy potassium salt. Commercially available propionate is generally sold as a monovalent cation salt of propionic acid, such as sodium propionate ($CH_3CH_2COONa$), or as a divalent cation salt, such as calcium propionate (Ca($CH_3CH_2COO$)$_2$). Propionate is membrane-permeable and is metabolized to 2-MC by conversion of propionate to propionyl-CoA by PrpE (propionyl-CoA synthetase), and then conversion of propionyl-CoA to 2-MC by PrpC (2-methylcitrate synthase). The other proteins encoded by the prpBCDE operon, PrpD (2-methylcitrate dehydratase) and PrpB (2-methylisocitrate lyase), are involved in further catabolism of 2-MC into smaller products such as pyruvate and succinate. In order to maximize induction of a propionate-inducible promoter by propionate added to the cell growth medium, it is therefore desirable to have a host cell with PrpC and PrpE activity, to convert propionate into 2-MC, but also having eliminated or reduced PrpD activity, and optionally eliminated or reduced PrpB activity as well, to prevent 2-MC from being metabolized. Another operon encoding proteins involved in 2-MC biosynthesis is the scpA-argK-scpBC operon, also called the sbm-ygfDGH operon. These genes encode proteins required for the conversion of succinate to propionyl-CoA, which can then be converted to 2-MC by PrpC. Elimination or reduction of the function of these proteins would remove a parallel pathway for the production of the 2-MC inducer, and thus might reduce background levels of expression of a propionate-inducible promoter, and increase sensitivity of the propionate-inducible promoter to exogenously supplied propionate. It has been found that a deletion of sbm-ygfD-ygfG-ygfH-ygfI, introduced into *E. coli* BL21(DE3) to create strain JSB (Lee and Keasling, "A propionate-inducible expression system for enteric bacteria", Appl Environ Microbiol 2005 November; 71(11): 6856-6862), was helpful in reducing background expression in the absence of exogenously supplied inducer, but this deletion also reduced overall expression from the prp promoter in strain JSB. It should be noted, however, that the deletion sbm-ygfD-ygfG-ygfH-ygfI also apparently affects ygfI, which encodes a putative LysR-family transcriptional regulator of unknown function. The genes sbm-ygfDGH are transcribed as one operon, and ygfI is transcribed from the opposite strand. The 3' ends of the ygfH and ygfI coding sequences overlap by a few base pairs, so a deletion that takes out all of the sbm-ygfDGH operon apparently takes out ygfI coding function as well. Eliminating or reducing the function of a subset of the sbm-ygfDGH gene products, such as YgfG (also called ScpB, methylmalonyl-CoA decarboxylase), or deleting the majority of the sbm-ygfDGH (or scpA-argK-scpBC) operon while leaving enough of the 3' end of the ygfH (or scpC) gene so that the expression of ygfI is not affected, could be sufficient to reduce background expression from a propionate-inducible promoter without reducing the maximal level of induced expression.

Rhamnose Promoter.

(As used herein, 'rhamnose' means L-rhamnose.) The 'rhamnose promoter' or 'rha promoter', or $P_{rhaSR}$, is the promoter for the *E. coli* rhaSR operon. Like the ara and prp promoters, the rha promoter is part of a bidirectional promoter, controlling expression of the rhaSR operon in one direction, and with the rhaBAD promoter controlling expression of the rhaBAD operon in the other direction. The rha promoter, however, has two transcriptional regulators involved in modulating expression: RhaR and RhaS. The RhaR protein activates expression of the rhaSR operon in the presence of rhamnose, while RhaS protein activates expression of the L-rhamnose catabolic and transport operons, rhaBAD and rhaT, respectively (Wickstrum et al., "The AraC/XylS family activator RhaS negatively autoregulates rhaSR expression by preventing cyclic AMP receptor protein activation", J Bacteriol 2010 January; 192(1): 225-232). Although the RhaS protein can also activate expression of the rhaSR operon, in effect RhaS negatively autoregulates this expression by interfering with the ability of the cyclic AMP receptor protein (CRP) to coactivate expression with RhaR to a much greater level. The rhaBAD operon encodes the rhamnose catabolic proteins RhaA (L-rhamnose isomerase), which converts L-rhamnose to L-rhamnulose; RhaB (rhamnulokinase), which phosphorylates L-rhamnulose to form L-rhamnulose-1-P; and RhaD (rhamnulose-1-phosphate aldolase), which converts L-rhamnulose-1-P to L-lactaldehyde and DHAP (dihydroxyacetone phosphate). To maximize the amount of rhamnose in the cell available for induction of expression from a rhamnose-inducible promoter, it is desirable to reduce the amount of rhamnose that is broken down by catalysis, by eliminating or reducing the function of RhaA, or optionally of RhaA and at least one of RhaB and RhaD. *E. coli* cells can also synthesize L-rhamnose from alpha-D-glucose-1-P through the activities of the proteins RmlA, RmlB, RmlC, and RmlD (also called RfbA, RfbB, RfbC, and RfbD, respectively) encoded by the rmlB-DACX (or rfbBDACX operon. To reduce background expression from a rhamnose-inducible promoter, and to enhance the sensitivity of induction of the rhamnose-inducible promoter by exogenously supplied rhamnose, it could be useful to eliminate or reduce the function of one or more of the RmlA, RmlB, RmlC, and RmlD proteins. L-rhamnose is transported into the cell by RhaT, the rhamnose permease or L-rhamnose:proton symporter. As noted above, the expression of RhaT is activated by the transcriptional regulator RhaS. To make expression of RhaT independent of induction by rhamnose (which induces expression of RhaS), the host cell can be altered so that all functional RhaT coding sequences in the cell are expressed from constitutive promoters. Additionally, the coding sequences for RhaS can be deleted or inactivated, so that no functional RhaS is produced. By eliminating or reducing the function of RhaS in the cell, the level of expression from the rhaSR promoter is increased due to the absence of negative autoregulation by RhaS, and the level of expression of the rhamnose catalytic operon rhaBAD is decreased, further increasing the ability of rhamnose to induce expression from the rha promoter.

Xylose Promoter.

(As used herein, 'xylose' means D-xylose.) The xylose promoter, or 'xyl promoter', or $P_{xylA}$, means the promoter for the E. coli xylAB operon. The xylose promoter region is similar in organization to other inducible promoters in that the xylAB operon and the xylFGHR operon are both expressed from adjacent xylose-inducible promoters in opposite directions on the E. coli chromosome (Song and Park, "Organization and regulation of the D-xylose operons in Escherichia coli K-12: XylR acts as a transcriptional activator", J Bacteriol. 1997 November; 179(22): 7025-7032). The transcriptional regulator of both the $P_{xylA}$ and $P_{xylF}$ promoters is XylR, which activates expression of these promoters in the presence of xylose. The xylR gene is expressed either as part of the xylFGHR operon or from its own weak promoter, which is not inducible by xylose, located between the xylH and xylR protein-coding sequences. D-xylose is catabolized by XylA (D-xylose isomerase), which converts D-xylose to D-xylulose, which is then phosphorylated by XylB (xylulokinase) to form D-xylulose-5-P. To maximize the amount of xylose in the cell available for induction of expression from a xylose-inducible promoter, it is desirable to reduce the amount of xylose that is broken down by catalysis, by eliminating or reducing the function of at least XylA, or optionally of both XylA and XylB. The xylFGHR operon encodes XylF, XylG, and XylH, the subunits of an ABC superfamily high-affinity D-xylose transporter. The xylE gene, which encodes the E. coli low-affinity xylose-proton symporter, represents a separate operon, the expression of which is also inducible by xylose. To make expression of a xylose transporter independent of induction by xylose, the host cell can be altered so that all functional xylose transporters are expressed from constitutive promoters. For example, the xylFGHR operon could be altered so that the xylFGH coding sequences are deleted, leaving XylR as the only active protein expressed from the xylose-inducible $P_{xylF}$ promoter, and with the xylE coding sequence expressed from a constitutive promoter rather than its native promoter. As another example, the xylR coding sequence is expressed from the $P_{xylA}$ or the $P_{xylF}$ promoter in an expression construct, while either the xylFGHR operon is deleted and xylE is constitutively expressed, or alternatively an xylFGH operon (lacking the xylR coding sequence since that is present in an expression construct) is expressed from a constitutive promoter and the xylE coding sequence is deleted or altered so that it does not produce an active protein.

Lactose Promoter.

The term 'lactose promoter' refers to the lactose-inducible promoter for the lacZYA operon, a promoter which is also called lacZp1; this lactose promoter is located at ca. 365603-365568 (minus strand, with the RNA polymerase binding ('-35') site at ca. 365603-365598, the Pribnow box ('-10') at 365579-365573, and a transcription initiation site at 365567) in the genomic sequence of the E. coli K-12 substrain MG1655 (NCBI Reference Sequence NC_000913.2, 11 Jan. 2012). In some embodiments, inducible coexpression systems of the invention can comprise a lactose-inducible promoter such as the lacZYA promoter. In other embodiments, the inducible coexpression systems of the invention comprise one or more inducible promoters that are not lactose-inducible promoters.

Alkaline Phosphatase Promoter.

The terms 'alkaline phosphatase promoter' and 'phoA promoter' refer to the promoter for the phoApsiF operon, a promoter which is induced under conditions of phosphate starvation. The phoA promoter region is located at ca. 401647-401746 (plus strand, with the Pribnow box ('-10') at 401695-401701 (Kikuchi et al., "The nucleotide sequence of the promoter and the amino-terminal region of alkaline phosphatase structural gene (phoA) of Escherichia coli", Nucleic Acids Res 1981 Nov. 11; 9(21): 5671-5678)) in the genomic sequence of the E. coli K-12 substrain MG1655 (NCBI Reference Sequence NC_000913.3, 16 Dec. 2014). The transcriptional activator for the phoA promoter is PhoB, a transcriptional regulator that, along with the sensor protein PhoR, forms a two-component signal transduction system in E. coli. PhoB and PhoR are transcribed from the phoBR operon, located at ca. 417050-419300 (plus strand, with the PhoB coding sequence at 417,142-417,831 and the PhoR coding sequence at 417,889-419,184) in the genomic sequence of the E. coli K-12 substrain MG1655 (NCBI Reference Sequence NC_000913.3, 16 Dec. 2014). The phoA promoter differs from the inducible promoters described above in that it is induced by the lack of a substance—intracellular phosphate—rather than by the addition of an inducer. For this reason the phoA promoter is generally used to direct transcription of gene products that are to be produced at a stage when the host cells are depleted for phosphate, such as the later stages of fermentation. In some embodiments, inducible coexpression systems of the invention can comprise a phoA promoter. In other embodiments, the inducible coexpression systems of the invention comprise one or more inducible promoters that are not phoA promoters.

TABLE 1

Genomic Locations of E. coli Inducible Promoters and Related Genes [1]

| Promoter or Gene | Genomic Location: | Comments: |
|---|---|---|
| araBAD promoter | [2] (ca. 70165)-70074 (minus strand) | Smith and Schleif [3]: RNA pol [4] binding ('-35') 70110-70104, Pribnow box ('-10') 70092-70085 |
| araBAD operon | 70075-65855 (minus strand) | Smith and Schleif [3]: transcript start 70075, araB ATG 70048; NCBI: araB end of TAA 68348; araA ATG 68337, end of TAA 66835; araD ATG 66550, end of TAA 65855 |
| araC promoter | [2] (ca. 70166)-70241 (plus strand) | Smith and Schleif [3]: RNA pol binding ('-35') 70210-7021, Pribnow box ('-10') 70230-70236 |
| araC gene | 70242-71265 (plus strand) | Miyada [5]: transcript start 70242, araC ATG 70387; NCBI: end of TAA 71265 |

TABLE 1-continued

Genomic Locations of E. coli Inducible Promoters and Related Genes [1]

| Promoter or Gene | Genomic Location: | Comments: |
|---|---|---|
| araE promoter | [2] (ca. 2980349)-2980231 (minus strand) | Stoner and Schleif [6]: CRP binding 2980349-2980312, RNA pol binding ('−35') 2980269-2980264, Pribnow box ('−10') 2980244-2980239 |
| araE gene | 2980230-2978786 (minus strand) | Stoner and Schleif [6]: transcript start 2980230, ATG 2980204; NCBI: end of TGA 2978786 |
| araFGH promoter | [2] (ca. 1984423)-1984264 (minus strand) | Hendrickson [7]: AraC binding ca. 1984423-ca. 1984414 and 1984326-1984317, CRP binding 1984315-1984297, RNA pol binding ('−35') 1984294-1984289, Pribnow box ('−10') 1984275-1984270 |
| araFGH operon | 1984263-1980578 (minus strand) | Hendrickson [7]: transcript start 1984263; NCBI: araF ATG 1984152, end of TAA 1983163; araG ATG 1983093, end of TGA 1981579; araH ATG 1981564, end of TGA 1980578 |
| lacY gene | 362403-361150 (minus strand) | Expressed as part of the lacZYA operon. NCBI: ATG 362403, end of TAA 361150 |
| prpBCDE promoter | [2] ca. 347790-ca. 347870 (plus strand) | Keasling [8]: RNA pol binding ('−24') 347844-347848, Pribnow box ('−12') 347855-347859 |
| prpBCDE operon | (ca. 347871)-353816 (plus strand) | Keasling [8]: inferred transcript start ca. 347871, prpB ATG 347906; NCBI: prpB end of TAA 348796; prpC ATG 349236, end of TAA 350405; prpD ATG 350439, end of TAA 351890; prpE ATG 351930, end of TAG 353816 |
| prpR promoter | [2] ca. 347789-ca. 347693 (minus strand) | Keasling [8]: CRP binding 347775-347753, RNA pol binding ('−35') 347728-347723, Pribnow box ('−10') 347707-347702 |
| prpR gene | (ca. 347692)-346081 (minus strand) | Keasling [8]: inferred transcript start ca. 347692, prpR ATG 347667; NCBI: end of TGA 346081 |
| scpA-argK-scpBC (or sbm-ygfDGH) operon | 3058872-3064302 (plus strand) | NCBI: scpA ATG 3058872, end of TAA 3061016; argK ATG 3061009, end of TAA 3062004; scpB ATG 3062015, end of TAA 3062800; scpC ATG 3062824, end of TAA 3064302 |
| rhaBAD promoter | [2] (ca. 4095605)-4095496 (minus strand) | Wickstrum [9]: CRP binding 4095595-4095580, RNA pol binding ('−35') 4095530-4095525, Pribnow box ('−10') 4095506-4095501 |
| rhaBAD operon | 4095495-4091471 (minus strand) | Wickstrum [9]: transcript start 4095495, rhaB ATG 4095471; NCBI: rhaB end of TGA 4094002; rhaA ATG 4094005, end of TAA 4092746; rhaD ATG 4092295, end of TAA 4091471 |
| rhaSR promoter | [2] (ca. 4095606)-4095733 (plus strand) | Wickstrum [9]: CRP binding 4095615-4095630, RNA pol binding ('−35') 4095699-4095704, Pribnow box ('−10') 4095722-4095727 |
| rhaSR operon | 4095734-4097517 (plus strand) | Wickstrum [9]: transcript start 4095734, rhaS ATG 4095759; NCBI: rhaS end of TAA 4096595; rhaR ATG 4096669, end of TAA 4097517 |
| rfbBDACX (or rmlBDACX) operon | 2111085-2106361 (minus strand) | NCBI: rfbB GTG 2111085, end of TAA 2110000; rfbD ATG 2110000, end of TAA 2109101; rfbA ATG 2109043, end of TAA 2108162; rfbC ATG 2108162, end of TGA 2107605; rfbX ATG 2107608, end of TGA 2106361 |
| rhaT promoter | [2] (ca. 4098690)-4098590 (minus strand) | Vía [10]: CRP binding 4098690-4098675, RNA pol binding ('−35') 4098621-4098616, Pribnow box ('−10') 4098601-4098596 |
| rhaT gene | 4098589-4097514 (minus strand) | Vía [10]: transcript start 4098589, rhaT ATG 4098548; NCBI: rhaT end of TAA 4097514 |
| xylAB promoter | [2] (ca. 3728960)-3728831 (minus strand) | Song and Park [11]: CRP binding 3728919-3728901, RNA pol binding ('−35') 3728865-3728860, Pribnow box ('−10') 3728841-3728836 |
| xylAB operon | 3728830-3725940 (minus strand) | Song and Park [11]: transcript start 3728830, xylA ATG 3728788; NCBI: xylA end of TAA 3727466; xylB ATG 3727394, end of TAA 3725940 |

TABLE 1-continued

Genomic Locations of *E. coli* Inducible Promoters and Related Genes [1]

| Promoter or Gene | Genomic Location: | Comments: |
|---|---|---|
| xylFGHR promoter | [2] (ca. 3728961)-3729091 (plus strand) | Song and Park [11]: RNA pol binding ('-35') 3729058-3729063, Pribnow box ('-10') 3729080-3729085 |
| xylFGHR operon | 3729092-3734180 (plus strand) | Song and Park [11]: transcript start 3729092, xylF ATG 3729154; NCBI: xylF end of TAA 3730146, xylG ATG 3730224, end of TGA 3731765; xylH ATG 3731743, end of TGA 3732924; xylR ATG 3733002, end of TAG 3734180 |
| xylE promoter | [2] ca. 4240482-ca. 4240320 (minus strand) | Davis and Henderson [12]: possible Pribnow box ('-10') 4240354-4240349, possible Pribnow box ('-10') 4240334-4240329 |
| xylE gene | (ca. 4240319)-4238802 (minus strand) | Davis and Henderson [12]: inferred transcript start ca. 4240319, xylE ATG 4240277, end of TAA 4238802 |

Notes for Table 1:
[1] All genomic sequence locations refer to the genomic sequence of *E. coli* K-12 substrain MG1655, provided by the National Center for Biotechnology Information (NCBI) as NCBI Reference Sequence NC_000913.2, 11 JAN. 2012.
[2] The location of the 5' (or 'upstream') end of the promoter region is approximated; for 'bidirectional' promoters, a nucleotide sequence location that is approximately equidistant between the transcription start sites is selected as the designated 5' 'end' for both of the individual promoters. In practice, the promoter portion of an expression construct can have somewhat less sequence at its 5' end than the promoter sequences as indicated in the table, or it can have a nucleotide sequence that includes additional sequence from the region 5' (or 'upstream') of the promoter sequences as indicated in the table, as long as it retains the ability to promote transcription of a downstream coding sequence in an inducible fashion.
[3] Smith and Schleif, "Nucleotide sequence of the L-arabinose regulatory region of *Escherichia coli* K12", J Biol Chem 1978 Oct. 10; 253(19): 6931-6933.
[4] 'RNA pol' indicates RNA polymerase throughout the table.
[5] Miyada, et al., "DNA sequence of the araC regulatory gene from *Escherichia coli* B/r", Nucleic Acids Res 1980 Nov. 25; 8(22): 5267-5274.
[6] Stoner and Schleif, "*E. coli* araE regulatory region araE codes for the low affinity L-arabinose uptake protein", GenBank Database Accession X00272.1, revision date 6 JUL. 1989.
[7] Hendrickson et al., "Sequence elements in the *Escherichia coli* araFGH promoter", J Bacteriol 1992 November; 174(21): 6862-6871.
[8] U.S. Pat. No. 8,178,338 B2; May 15, 2012; Keasling, Jay; FIG. 9.
[9] Wickstrum et al., "The AraC/XylS family activator RhaS negatively autoregulates rhaSR expression by preventing cyclic AMP receptor protein activation", J Bacteriol 2010 January; 192(1): 225-232.
[10] Via et al., "Transcriptional regulation of the *Escherichia coli* rhaT gene", Microbiology 1996 July; 142(Pt 7): 1833-1840.
[11] Song and Park, "Organization and regulation of the D-xylose operons in *Escherichia coli* K-12: XylR acts as a transcriptional activator", J Bacteriol. 1997 November; 179(22): 7025-7032.
[12] Davis and Henderson, "The cloning and DNA sequence of the gene xylE for xylose-proton symport in *Escherichia coli* K12", J Biol Chem 1987 Oct. 15; 262(29): 13928-13932.

Expression Constructs.

Expression constructs are polynucleotides designed for the expression of one or more gene products of interest, and thus are not naturally occurring molecules. Expression constructs can be integrated into a host cell chromosome, or maintained within the host cell as polynucleotide molecules replicating independently of the host cell chromosome, such as plasmids or artificial chromosomes. An example of an expression construct is a polynucleotide resulting from the insertion of one or more polynucleotide sequences into a host cell chromosome, where the inserted polynucleotide sequences alter the expression of chromosomal coding sequences. An expression vector is a plasmid expression construct specifically used for the expression of one or more gene products. One or more expression constructs can be integrated into a host cell chromosome or be maintained on an extrachromosomal polynucleotide such as a plasmid or artificial chromosome. The following are descriptions of particular types of polynucleotide sequences that can be used in expression constructs for the coexpression of gene products.

Origins of Replication.

Expression constructs must comprise an origin of replication, also called a replicon, in order to be maintained within the host cell as independently replicating polynucleotides. Different replicons that use the same mechanism for replication cannot be maintained together in a single host cell through repeated cell divisions. As a result, plasmids can be categorized into incompatibility groups depending on the origin of replication that they contain, as shown in Table 2.

TABLE 2

Origins of Replication and Representative Plasmids for Use in Expression Constructs [1]

| Incompatibility Group: | Origin of Replication: | Copy Number: | Representative Plasmids (ATCC Deposit No.): |
|---|---|---|---|
| colE1, pMB1 | colE1 | 15-20 | colE1 (ATCC 27138) |
| | pMB1 | 15-20 | pBR322 (ATCC 31344) |
| | Modified pMB1 | 500-700 | pUC9 (ATCC 37252) |
| IncFII, pT181 F, P1, p15A, pSC101, R6K, RK2 [2] | R1(ts) | 15-120 | pMOB45 (ATCC 37106) |
| | p15A | 18-22 | pACYC177 (ATCC 37031); pACYC184 (ATCC 37033); pPRO33 (Addgene 17810) [3] |
| | pSC101 | ~5 | pSC101 (ATCC 37032): pGBM1 (ATCC 87497) |
| | RK2 | 4-7 [2] | RK2 (ATCC 37125) |
| CloDF13 [4] | CloDF13 | 20-40 [4] | pCDFDuet ™-1 (EMD Millipore Catalog No. 71340-3) |
| ColA [4] | ColA | 20-40 [4] | pCOLADuet ™-1 (EMD Millipore Catalog No. 71406-3) |

TABLE 2-continued

Origins of Replication and Representative Plasmids
for Use in Expression Constructs [1]

| Incompatibility Group: | Origin of Replication: | Copy Number: | Representative Plasmids (ATCC Deposit No.): |
|---|---|---|---|
| RSF1030 [4] | RSF1030 (also called NTP1) | >100 [4] | pRSFDuet ™-1 (EMD Millipore Catalog No. 71341-3) |

Notes for Table 2:
[1] Adapted from bio.davidson.edu, and Sambrook and Russell, "Molecular Cloning: A laboratory manual", 3$^{rd}$ Ed., Cold Spring Harbor Laboratory Press, 2001.
[2] Kües and Stahl, "Replication of plasmids in gram-negative bacteria", Microbiol Rev 1989 December; 53(4): 491-516.
[3] The pPRO33 plasmid (U.S. Pat. No. 8,178,338 B2; May 15, 2012; Keasling, Jay) is available from Addgene (addgene.org) as Addgene plasmid 17810.
[4] openwetware.org/wiki/CH391L/S12/Origins_of_Replication; accessed 3 Aug. 2013.

Origins of replication can be selected for use in expression constructs on the basis of incompatibility group, copy number, and/or host range, among other criteria. As described above, if two or more different expression constructs are to be used in the same host cell for the coexpression of multiple gene products, it is best if the different expression constructs contain origins of replication from different incompatibility groups: a pMB1 replicon in one expression construct and a p15A replicon in another, for example. The average number of copies of an expression construct in the cell, relative to the number of host chromosome molecules, is determined by the origin of replication contained in that expression construct. Copy number can range from a few copies per cell to several hundred (Table 2). In one embodiment of the invention, different expression constructs are used which comprise inducible promoters that are activated by the same inducer, but which have different origins of replication. By selecting origins of replication that maintain each different expression construct at a certain approximate copy number in the cell, it is possible to adjust the levels of overall production of a gene product expressed from one expression construct, relative to another gene product expressed from a different expression construct. As an example, to coexpress subunits A and B of a multimeric protein, an expression construct is created which comprises the colE1 replicon, the ara promoter, and a coding sequence for subunit A expressed from the ara promoter: 'colE1-P$_{ara}$-A'. Another expression construct is created comprising the p15A replicon, the ara promoter, and a coding sequence for subunit B: 'p15A-P$_{ara}$-B'. These two expression constructs can be maintained together in the same host cells, and expression of both subunits A and B is induced by the addition of one inducer, arabinose, to the growth medium. If the expression level of subunit A needed to be significantly increased relative to the expression level of subunit B, in order to bring the stoichiometric ratio of the expressed amounts of the two subunits closer to a desired ratio, for example, a new expression construct for subunit A could be created, having a modified pMB1 replicon as is found in the origin of replication of the pUC9 plasmid ('pUC9ori'): pUC9ori-P$_{ara}$-A. Expressing subunit A from a high-copy-number expression construct such as pUC9ori-P$_{ara}$-A should increase the amount of subunit A produced relative to expression of subunit B from p15A-P$_{ara}$-B. In a similar fashion, use of an origin of replication that maintains expression constructs at a lower copy number, such as pSC101, could reduce the overall level of a gene product expressed from that construct. Selection of an origin of replication can also determine which host cells can maintain an expression construct comprising that replicon. For example, expression constructs comprising the colE1 origin of replication have a relatively narrow range of available hosts, species within the Enterobacteriaceae family, while expression constructs comprising the RK2 replicon can be maintained in *E. coli, Pseudomonas aeruginosa, Pseudomonas putida, Azotobacter vinelandii*, and *Alcaligenes eutrophus*, and if an expression construct comprises the RK2 replicon and some regulator genes from the RK2 plasmid, it can be maintained in host cells as diverse as *Sinorhizobium meliloti, Agrobacterium tumefaciens, Caulobacter crescentus, Acinetobacter calcoaceticus*, and *Rhodobacter sphaeroides* (Kües and Stahl, "Replication of plasmids in grain-negative bacteria", Microbiol Rev 1989 December; 53(4): 491-516).

Similar considerations can be employed to create expression constructs for inducible coexpression in eukaryotic cells. For example, the 2-micron circle plasmid of *Saccharomyces cerevisiae* is compatible with plasmids from other yeast strains, such as pSR1 (ATCC Deposit Nos. 48233 and 66069; Araki et al., "Molecular and functional organization of yeast plasmid pSR1", J Mol Biol 1985 Mar. 20; 182(2): 191-203) and pKD1 (ATCC Deposit No. 37519; Chen et al., "Sequence organization of the circular plasmid pKD1 from the yeast *Kluyveromyces drosophilarum*", Nucleic Acids Res 1986 Jun. 11; 14(11): 4471-4481).

Selectable Markers.

Expression constructs usually comprise a selection gene, also termed a selectable marker, which encodes a protein necessary for the survival or growth of host cells in a selective culture medium. Host cells not containing the expression construct comprising the selection gene will not survive in the culture medium. Typical selection genes encode proteins that confer resistance to antibiotics or other toxins, or that complement auxotrophic deficiencies of the host cell. One example of a selection scheme utilizes a drug such as an antibiotic to arrest growth of a host cell. Those cells that contain an expression construct comprising the selectable marker produce a protein conferring drug resistance and survive the selection regimen. Some examples of antibiotics that are commonly used for the selection of selectable markers (and abbreviations indicating genes that provide antibiotic resistance phenotypes) are: ampicillin (Amp$^R$), chloramphenicol (Cml$^R$ or Cm$^R$), kanamycin (Kan$^R$), spectinomycin (Spc$^R$), streptomycin (Str$^R$), and tetracycline (Tet$^R$). Many of the representative plasmids in Table 2 comprise selectable markers, such as pBR322 (Amp$^R$, Tet$^R$); pMOB45 (Cm$^R$, Tet$^R$); pACYC177 (Amp$^R$, Kan$^R$); and pGBM1 (Spc$^R$, Str$^R$). The native promoter region for a selection gene is usually included, along with the coding sequence for its gene product, as part of a selectable marker portion of an expression construct. Alternatively, the coding sequence for the selection gene can be expressed from a constitutive promoter.

Inducible Promoter.

As described herein, there are several different inducible promoters that can be included in expression constructs as part of the inducible coexpression systems of the invention. Preferred inducible promoters share at least 80% polynucleotide sequence identity (more preferably, at least 90% identity, and most preferably, at least 95% identity) to at least 30 (more preferably, at least 40, and most preferably, at least 50) contiguous bases of a promoter polynucleotide sequence as defined in Table 1 by reference to the *E. coli* K-12 substrain MG1655 genomic sequence, where percent polynucleotide sequence identity is determined using the methods of Example 11. Under 'standard' inducing conditions (see Example 5), preferred inducible promoters have at least 75% (more preferably, at least 100%, and most preferably, at least 110%) of the strength of the corresponding 'wild-type' inducible promoter of *E. coli* K-12 substrain MG1655, as determined using the quantitative PCR method of De Mey et al. (Example 6). Within the expression construct, an inducible promoter is placed 5' to (or 'upstream of') the coding sequence for the gene product that is to be inducibly expressed, so that the presence of the inducible promoter will direct transcription of the gene product coding sequence in a 5' to 3' direction relative to the coding strand of the polynucleotide encoding the gene product.

Ribosome Binding Site.

For polypeptide gene products, the nucleotide sequence of the region between the transcription initiation site and the initiation codon of the coding sequence of the gene product that is to be inducibly expressed corresponds to the 5' untranslated region ('UTR') of the mRNA for the polypeptide gene product. Preferably, the region of the expression construct that corresponds to the 5' UTR comprises a polynucleotide sequence similar to the consensus ribosome binding site (RBS, also called the Shine-Dalgarno sequence) that is found in the species of the host cell. In prokaryotes (archaea and bacteria), the RBS consensus sequence is GGAGG or GGAGGU, and in bacteria such as *E. coli*, the RBS consensus sequence is AGGAGG or AGGAGGU. The RBS is typically separated from the initiation codon by 5 to 10 intervening nucleotides. In expression constructs, the RBS sequence is preferably at least 55% identical to the AGGAGGU consensus sequence, more preferably at least 70% identical, and most preferably at least 85% identical, and is separated from the initiation codon by 5 to 10 intervening nucleotides, more preferably by 6 to 9 intervening nucleotides, and most preferably by 6 or 7 intervening nucleotides. The ability of a given RBS to produce a desirable translation initiation rate can be calculated at the website salis.psu.edu/software/RBSLibraryCalculatorSearchMode, using the RBS Calculator; the same tool can be used to optimize a synthetic RBS for a translation rate across a 100,000+ fold range (Salis, "The ribosome binding site calculator", Methods Enzymol 2011; 498: 19-42).

Multiple Cloning Site.

A multiple cloning site (MCS), also called a polylinker, is a polynucleotide that contains multiple restriction sites in close proximity to or overlapping each other. The restriction sites in the MCS typically occur once within the MCS sequence, and preferably do not occur within the rest of the plasmid or other polynucleotide construct, allowing restriction enzymes to cut the plasmid or other polynucleotide construct only within the MCS. Examples of MCS sequences are those in the pBAD series of expression vectors, including pBAD18, pBAD18-Cm, pBAD18-Kan, pBAD24, pBAD28, pBAD30, and pBAD33 (Guzman et al., "Tight regulation, modulation, and high-level expression by vectors containing the arabinose PBAD promoter", J Bacteriol 1995 July; 177(14): 4121-4130); or those in the pPRO series of expression vectors derived from the pBAD vectors, such as pPRO18, pPRO18-Cm, pPRO18-Kan, pPRO24, pPRO30, and pPRO33 (U.S. Pat. No. 8,178,338 B2; May 15, 2012; Keasling, Jay). A multiple cloning site can be used in the creation of an expression construct: by placing a multiple cloning site 3' to (or downstream of) a promoter sequence, the MCS can be used to insert the coding sequence for a gene product to be coexpressed into the construct, in the proper location relative to the promoter so that transcription of the coding sequence will occur. Depending on which restriction enzymes are used to cut within the MCS, there may be some part of the MCS sequence remaining within the expression construct after the coding sequence or other polynucleotide sequence is inserted into the expression construct. Any remaining MCS sequence can be upstream or, or downstream of, or on both sides of the inserted sequence. A ribosome binding site can be placed upstream of the MCS, preferably immediately adjacent to or separated from the MCS by only a few nucleotides, in which case the RBS would be upstream of any coding sequence inserted into the MCS. Another alternative is to include a ribosome binding site within the MCS, in which case the choice of restriction enzymes used to cut within the MCS will determine whether the RBS is retained, and in what relation to, the inserted sequences. A further alternative is to include a RBS within the polynucleotide sequence that is to be inserted into the expression construct at the MCS, preferably in the proper relation to any coding sequences to stimulate initiation of translation from the transcribed messenger RNA.

Expression from Constitutive Promoters.

Expression constructs of the invention can also comprise coding sequences that are expressed from constitutive promoters. Unlike inducible promoters, constitutive promoters initiate continual gene product production under most growth conditions. One example of a constitutive promoter is that of the Tn3 bla gene, which encodes beta-lactamase and is responsible for the ampicillin-resistance ($Amp^R$) phenotype conferred on the host cell by many plasmids, including pBR322 (ATCC 31344), pACYC177 (ATCC 37031), and pBAD24 (ATCC 87399). Another constitutive promoter that can be used in expression constructs is the promoter for the *E. coli* lipoprotein gene, lpp, which is located at positions 1755731-1755406 (plus strand) in *E. coli* K-12 substrain MG1655 (Inouye and Inouye, "Uppromoter mutations in the lpp gene of *Escherichia coli*", Nucleic Acids Res 1985 May 10; 13(9): 3101-3110). A further example of a constitutive promoter that has been used for heterologous gene expression in *E. coli* is the trpLEDCBA promoter, located at positions 1321169-1321133 (minus strand) in *E. coli* K-12 substrain MG1655 (Windass et al., "The construction of a synthetic *Escherichia coli* trp promoter and its use in the expression of a synthetic interferon gene", Nucleic Acids Res 1982 Nov. 11; 10(21): 6639-6657). Constitutive promoters can be used in expression constructs for the expression of selectable markers, as described herein, and also for the constitutive expression of other gene products useful for the coexpression of the desired product. For example, transcriptional regulators of the inducible promoters, such as AraC, PrpR, RhaR, and XylR, if not expressed from a bidirectional inducible promoter, can alternatively be expressed from a constitutive promoter, on either the same expression construct as the inducible promoter they regulate, or a different expression construct. Similarly, gene products useful for the production or transport of the inducer, such as PrpEC, AraE, or Rha, or proteins that modify the reduction-oxidation environment of the cell, as a few examples, can be expressed from a constitutive promoter within an expression construct. Gene products useful for the production of coexpressed gene products, and the resulting desired product, also include chaperone proteins, cofactor transporters, etc.

Signal Peptides.

Polypeptide gene products coexpressed by the methods of the invention can contain signal peptides or lack them, depending on whether it is desirable for such gene products to be exported from the host cell cytoplasm into the periplasm, or to be retained in the cytoplasm, respectively. Signal peptides (also termed signal sequences, leader sequences, or leader peptides) are characterized structurally by a stretch of hydrophobic amino acids, approximately five to twenty amino acids long and often around ten to fifteen amino acids in length, that has a tendency to form a single alpha-helix. This hydrophobic stretch is often immediately preceded by a shorter stretch enriched in positively charged amino acids (particularly lysine). Signal peptides that are to be cleaved from the mature polypeptide typically end in a stretch of amino acids that is recognized and cleaved by signal peptidase. Signal peptides can be characterized functionally by the ability to direct transport of a polypeptide, either co-translationally or post-translationally, through the plasma membrane of prokaryotes (or the inner membrane of grain negative bacteria like *E. coli*), or into the endoplasmic reticulum of eukaryotic cells. The degree to which a signal peptide enables a polypeptide to be transported into the periplasmic space of a host cell like *E. coli*, for example, can be determined by separating periplasmic proteins from proteins retained in the cytoplasm, using a method such as that provided in Example 12.

Host Cells.

The inducible coexpression systems of the invention are designed to express multiple gene products; in certain embodiments of the invention, the gene products are coexpressed in a host cell. Examples of host cells are provided that allow for the efficient and cost-effective inducible coexpression of components of multimeric products. Host cells can include, in addition to isolated cells in culture, cells that are part of a multicellular organism, or cells grown within a different organism or system of organisms. In addition, the expression constructs of the inducible coexpression systems of the invention can be used in cell-free systems, such as those based on wheat germ extracts or on bacterial cell extracts, such as a continuous-exchange cell-free (CECF) protein synthesis system using *E. coli* extracts and an incubation apparatus such as the RTS ProteoMaster (Roche Diagnostics GmbH; Mannheim, Germany) (Jun et al., "Continuous-exchange cell-free protein synthesis using PCR-generated DNA and an RNase E-deficient extract", Biotechniques 2008 March; 44(3): 387-391).

Prokaryotic Host Cells.

In some embodiments of the invention, expression constructs designed for coexpression of gene products are provided in host cells, preferably prokaryotic host cells. Prokaryotic host cells can include archaea (such as *Haloferax volcanii, Sulfolobus solfataricus*), Grain-positive bacteria (such as *Bacillus subtilis, Bacillus licheniformis, Brevibacillus choshinensis, Lactobacillus brevis, Lactobacillus buchneri, Lactococcus lactis,* and *Streptomyces lividans*), or Grain-negative bacteria, including Alphaproteobacteria (*Agrobacterium tumefaciens, Caulobacter crescentus, Rhodobacter sphaeroides,* and *Sinorhizobium meliloti*), Betaproteobacteria (*Alcaligenes eutrophus*), and Gammaproteobacteria (*Acinetobacter calcoaceticus, Azotobacter vinelandii, Escherichia coli, Pseudomonas aeruginosa,* and *Pseudomonas putida*). Preferred host cells include Gammaproteobacteria of the family Enterobacteriaceae, such as *Enterobacter, Erwinia, Escherichia* (including *E. coli*), *Klebsiella, Proteus, Salmonella* (including *Salmonella typhimurium*), *Serratia* (including *Serratia marcescens*), and *Shigella*.

Eukaryotic Host Cells.

Many additional types of host cells can be used for the inducible coexpression systems of the invention, including eukaryotic cells such as yeast (*Candida shehatae, Kluyveromyces lactis, Kluyveromyces fragilis,* other *Kluyveromyces* species, *Pichia pastoris, Saccharomyces cerevisiae, Saccharomyces pastorianus* also known as *Saccharomyces carlsbergensis, Schizosaccharomyces pombe, Dekkera/Brettanomyces* species, and *Yarrowia lipolytica*); other fungi (*Aspergillus nidulans, Aspergillus niger, Neurospora crassa, Penicillium, Tolypocladium, Trichoderma reesia*); insect cell lines (*Drosophila melanogaster* Schneider 2 cells and *Spodoptera frugiperda* Sf9 cells); and mammalian cell lines including immortalized cell lines (Chinese hamster ovary (CHO) cells, HeLa cells, baby hamster kidney (BHK) cells, monkey kidney cells (COS), human embryonic kidney (HEK, 293, or HEK-293) cells, and human hepatocellular carcinoma cells (Hep G2)). The above host cells are available from the American Type Culture Collection.

Alterations to Host Cell Gene Functions.

Certain alterations can be made to the gene functions of host cells comprising inducible expression constructs, to promote efficient and homogeneous induction of the host cell population by an inducer. Preferably, the combination of expression constructs, host cell genotype, and induction conditions results in at least 75% (more preferably at least 85%, and most preferably, at least 95%) of the cells in the culture expressing gene product from each induced promoter, as measured by the method of Khlebnikov et al. described in Example 6. For host cells other than *E. coli*, these alterations can involve the function of genes that are structurally similar to an *E. coli* gene, or genes that carry out a function within the host cell similar to that of the *E. coli* gene. Alterations to host cell gene functions include eliminating or reducing gene function by deleting the gene protein-coding sequence in its entirety, or deleting a large enough portion of the gene, inserting sequence into the gene, or otherwise altering the gene sequence so that a reduced level of functional gene product is made from that gene. Alterations to host cell gene functions also include increasing gene function by, for example, altering the native promoter to create a stronger promoter that directs a higher level of transcription of the gene, or introducing a missense mutation into the protein-coding sequence that results in a more highly active gene product. Alterations to host cell gene functions include altering gene function in any way, including for example, altering a native inducible promoter to create a promoter that is constitutively activated. In addition to alterations in gene functions for the transport and metabolism of inducers, as described herein with relation to inducible promoters, and an altered expression of chaperone proteins, it is also possible to alter the carbon catabolite repression (CCR) regulatory system and/or the reduction-oxidation environment of the host cell.

Carbon Catabolite Repression (CCR).

The presence of an active CCR regulatory system within a host can affect the ability of an inducer to activate transcription from an inducible promoter. For example, when a host cell such as *E. coli* is grown in a medium containing glucose, genes needed for the utilization of other carbon sources, such as the araBAD and prpBCDE operons, are expressed at a low level if at all, even if the arabinose or propionate inducer is also present in the growth medium. There is also a hierarchy of utilization of carbon sources other than glucose: as in the case of the ara and prp inducible promoter systems, where the presence of arabinose reduces the ability of propionate to induce expression from the prpBCDE promoter (Park et al., "The mechanism of sugar-mediated catabolite repression of the propionate catabolic genes in *Escherichia coli*", Gene 2012 Aug. 1; 504(1): 116-121; Epub 2012 May 3). The CCR mechanism of the cell therefore makes it more difficult to use two or more carbon-source inducers in an inducible coexpression system, as the presence of the inducer that is the preferred carbon source will inhibit induction by less-preferred carbon sources. The Park et al. authors attempted to relieve the repression of the prp promoter by arabinose, by using either a mutant crp gene that produces an altered cAMP receptor protein that can function independently of cAMP, or a deletion of PTS (phosphotransferase system) genes involved in the regulation of CCR; both approaches were largely unsuccessful. However, the PTS-knockout strain used by the Park et al. authors is based on strain TP2811, which is a deletion of the *E. coli* ptsHI-crr operon (Hernandez-Montalvo et al., "Characterization of sugar mixtures utilization by an *Escherichia coli* mutant devoid of the phosphotransferase system", Appl Microbiol Biotechnol 2001 October; 57(1-2): 186-191). Deletion of the entire ptsHI-crr operon has been found to affect total cAMP synthesis more significantly than a deletion of just the crr gene (Levy et al., "Cyclic AMP synthesis in *Escherichia coli* strains bearing known deletions in the pts phosphotransferase operon", Gene 1990 Jan. 31; 86(1): 27-33). A different approach is to eliminate or reduce the function of ptsG gene in the host cell, which encodes glucose-specific EII A (EII $A^{glc}$), a key element for CCR in *E. coli* (Kiln et al., "Simultaneous consumption of pentose and hexose sugars: an optimal microbial phenotype for efficient fermentation of lignocellulosic biomass", Appl Microbiol Biotechnol 2010 November; 88(5): 1077-1085, Epub 2010 September 14). Another alteration in the genome of a host cell such as *E. coli*, which leads to increased transcription of the prp promoter, is to eliminate or reduce the gene function of the ascG gene, which encodes AscG. AscG is the repressor of the beta-D-glucoside-utilization operon ascFB under normal growth conditions, and also represses transcription of the prp promoter; disruption of the AscG coding sequence has been shown to increase transcription from the prp promoter (Ishida et al., "Participation of regulator AscG of the beta-glucoside utilization operon in regulation of the propionate catabolism operon", J Bacteriol 2009 October; 191(19): 6136-6144; Epub 2009 Jul. 24). A further alternative is to increase expression of the transcriptional regulator of promoters inducible by the less-preferred carbon-source inducer, by placing it either under the control of a strong constitutive promoter, or under the control of the more-preferred carbon-source inducer. For example, to increase the induction of genes needed for the utilization of the less-preferred carbon source xylose in the presence of the more-preferred arabinose, the coding sequence for XylR is placed into the *E. coli* araBAD operon (Groff et al., "Supplementation of intracellular XylR leads to coutilization of hemicellulose sugars", Appl Environ Microbiol 2012 April; 78(7): 2221-2229, Epub 2012 Jan. 27). Host cells comprising inducible coexpression constructs therefore preferably include an increased level of gene function for transcriptional regulators of promoters inducible by the less-preferred carbon-source inducer(s), and an eliminated or reduced gene function for genes involved in the CCR system, such as crr and/or ptsG and/or ascG.

Cellular Transport of Cofactors.

When using the inducible coexpression systems of the invention to produce enzymes that require cofactors for function, it is helpful to use a host cell capable of synthesizing the cofactor from available precursors, or taking it up from the environment. Common cofactors include ATP, coenzyme A, flavin adenine dinucleotide (FAD), $NAD^+$/NADH, and heme.

Host Cell Reduction-Oxidation Environment.

Many multimeric gene products, such as antibodies, contain disulfide bonds. The cytoplasm of *E. coli* and many other cells is normally maintained in a reduced state by the thioredoxin and the glutaredoxin/glutathione enzyme systems. This precludes the formation of disulfide bonds in the cytoplasm, and proteins that need disulfide bonds are exported into the periplasm where disulfide bond formation and isomerization is catalyzed by the Dsb system, comprising DsbABCD and DsbG. Increased expression of the cysteine oxidase DsbA, the disulfide isomerase DsbC, or combinations of the Dsb proteins, which are all normally transported into the periplasm, has been utilized in the expression of heterologous proteins that require disulfide bonds (Makino et al., "Strain engineering for improved expression of recombinant proteins in bacteria", Microb Cell Fact 2011 May 14; 10: 32). It is also possible to express cytoplasmic forms of these Dsb proteins, such as a cytoplasmic version of DsbC ('cDsbC'), that lacks a signal peptide and therefore is not transported into the periplasm. Cytoplasmic Dsb proteins such as cDsbC are useful for making the cytoplasm of the host cell more oxidizing and thus more conducive to the formation of disulfide bonds in heterologous proteins produced in the cytoplasm. The host cell cytoplasm can also be made more oxidizing by altering the thioredoxin and the glutaredoxin/glutathione enzyme systems directly: mutant strains defective in glutathione reductase (gor) or glutathione synthetase (gshB), together with thioredoxin reductase (trxB), render the cytoplasm oxidizing. These strains are unable to reduce ribonucleotides and therefore cannot grow in the absence of exogenous reductant, such as dithiothreitol (DTT). Suppressor mutations (ahpC*) in the gene ahpC, which encodes the peroxiredoxin AhpC, convert it to a disulfide reductase that generates reduced glutathione, allowing the channeling of electrons onto the enzyme ribonucleotide reductase and enabling the cells defective in gor and trxB, or defective in gshB and trxB, to grow in the absence of DTT. A different class of mutated forms of AhpC can allow strains, defective in the activity of gamma-glutamylcysteine synthetase (gshA) and defective in trxB, to grow in the absence of DTT; these include AhpC V164G, AhpC S71F, AhpC E173/S71F, AhpC E171Ter, and AhpC dup162-169 (Faulkner et al., "Functional plasticity of a peroxidase allows evolution of diverse disulfide-reducing pathways", Proc Natl Acad Sci USA 2008 May 6; 105(18): 6735-6740, Epub 2008 May 2). In such strains with oxidizing cytoplasm, exposed protein cysteines become readily oxidized in a process that is catalyzed by thioredoxins, in a reversal of their physiological function, resulting in the formation of disulfide bonds.

Another alteration that can be made to host cells is to express the sulfhydryl oxidase Erv1p from the inner membrane space of yeast mitochondria in the host cell cytoplasm, which has been shown to increase the production of a variety of complex, disulfide-bonded proteins of eukaryotic origin in the cytoplasm of *E. coli*, even in the absence of mutations in gor or trxB (Nguyen et al., "Pre-expression of a sulfhydryl oxidase significantly increases the yields of eukaryotic disulfide bond containing proteins expressed in the cytoplasm of *E. coli*" Microb Cell Fact 2011 Jan. 7; 10: 1). Host cells comprising inducible coexpression constructs preferably also express cDsbC and/or Erv1p, are deficient in trxB gene function, are also deficient in the gene function of either gor, gshB, or gshA, and express an appropriate mutant form of AhpC so that the host cells can be grown in the absence of DTT.

Glycosylation of Polypeptide Gene Products.

Host cells can have alterations in their ability to glycosylate polypeptides. For example, eukaryotic host cells can have eliminated or reduced gene function in glycosyltransferase and/or oligo-saccharyltransferase genes, impairing the normal eukaryotic glycosylation of polypeptides to form glycoproteins. Prokaryotic host cells such as E. coli, which do not normally glycosylate polypeptides, can be altered to express a set of eukaryotic and prokaryotic genes that provide a glycosylation function (DeLisa et al., "Glycosylated protein expression in prokaryotes", WO2009089154A2, 2009 Jul. 16).

Available Host Cell Strains with Altered Gene Functions.

To create preferred strains of host cells to be used in the inducible coexpression systems and methods of the invention, it is useful to start with a strain that already comprises desired genetic alterations (Table 3).

TABLE 3

Host Cell Strains

| Strain: | Genotype: | Source: |
|---|---|---|
| E. coli TOP10 | F- mcrA Δ(mrr-hsdRMS-mcrBC) φ80lacZΔM15 ΔlacX74 recA1 araD139 Δ(ara-leu)7697 galU galK rpsL (Str$^R$) endA1 nupG λ- | Invitrogen Life Technologies Catalog nos. C4040-10, C4040-03, C4040-06, C4040-50, and C4040-52 |
| E. coli Origami™ 2 | Δ(ara-leu)7697 ΔlacX74 ΔphoA PvuII phoR araD139 ahpC galE galK rpsL F'[lac$^+$ lacI$^q$ pro] gor522::Tn10 trxB (Str$^R$, Tet$^R$) | Merck (EMD Millipore Chemicals) Catalog No. 71344 |
| E. coli SHuffle ® Express | fhuA2 [lon] ompT ahpC gal λatt::pNEB3-1-cDsbC (Spec, lacI) ΔtrxB sulA11 R(mcr-73::miniTn10--Tet$^S$)2 [dcm] R(zgb-210::Tn10--Tet$^S$) endA1 Δgor Δ(mcrC-mrr)114::IS10 | New England Biolabs Catalog No. C3028H |

Methods of Altering Host Cell Gene Functions.

There are many methods known in the art for making alterations to host cell genes in order to eliminate, reduce, or change gene function. Methods of making targeted disruptions of genes in host cells such as E. coli and other prokaryotes have been described (Muyrers et al., "Rapid modification of bacterial artificial chromosomes by ET-recombination", Nucleic Acids Res 1999 March 15; 27(6): 1555-1557; Datsenko and Wanner, "One-step inactivation of chromosomal genes in Escherichia coli K-12 using PCR products", Proc Natl Acad Sci USA 2000 Jun. 6; 97(12): 6640-6645), and kits for using similar Red/ET recombination methods are commercially available (for example, the Quick & Easy E. coli Gene Deletion Kit from Gene Bridges GmbH, Heidelberg, Germany). In one embodiment of the invention, the function of one or more genes of host cells is eliminated or reduced by identifying a nucleotide sequence within the coding sequence of the gene to be disrupted, such as one of the E. coli K-12 substrain MG1655 coding sequences incorporated herein by reference to the genomic location of the sequence, and more specifically by selecting two adjacent stretches of 50 nucleotides each within that coding sequence. The Quick & Easy E. coli Gene Deletion Kit is then used according to the manufacturer's instructions to insert a polynucleotide construct containing a selectable marker between the selected adjacent stretches of coding sequence, eliminating or reducing the normal function of the gene. Red/ET recombination methods can also be used to replace a promoter sequence with that of a different promoter, such as a constitutive promoter, or an artificial promoter that is predicted to promote a certain level of transcription (De Mey et al., "Promoter knock-in: a novel rational method for the fine tuning of genes", BMC Biotechnol 2010 March 24; 10: 26). The function of host cell genes can also be eliminated or reduced by RNA silencing methods (Man et al., "Artificial trans-encoded small non-coding RNAs specifically silence the selected gene expression in bacteria", Nucleic Acids Res 2011 April; 39(8): e50, Epub 2011 Feb. 3). Further, known mutations that alter host cell gene function can be introduced into host cells through traditional genetic methods.

Inducible Coexpression Systems of the Invention

Figure 3:
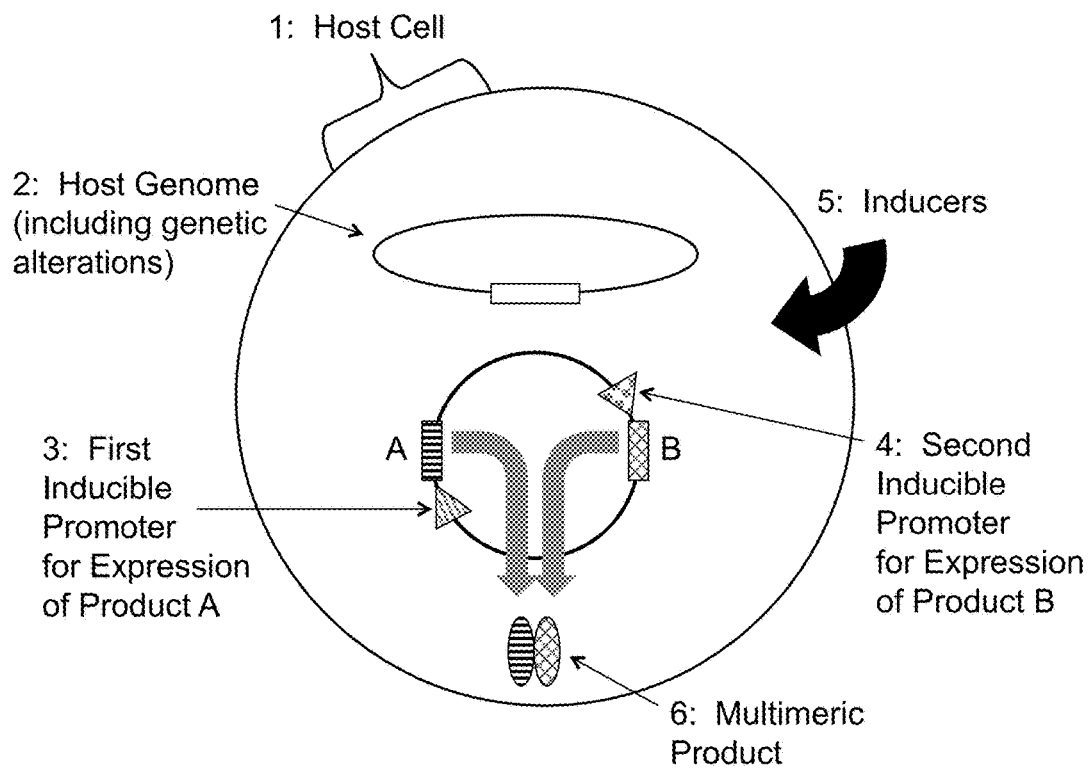
FIG. 3 is a schematic illustration of an inducible coexpression system, which includes a host cell (1) comprising an inducible expression vector comprising two different inducible promoters (3) and (4), which express different gene products upon application of inducers (5), forming a multimeric product (6).

Inducible coexpression systems of the invention involve host cells comprising two or more expression constructs, where the expression constructs comprise inducible promoters directing the expression of gene products, and the host cells have altered gene functions that allow for homogeneous inducible expression of the gene products. FIG. 1 shows a schematic representation of an inducible coexpression system of the invention, with the following components: (1) host cell, (2) host genome (including genetic alterations), (3) an expression vector 'X' comprising an inducible promoter directing expression of a gene product, (4) a different expression vector 'Y' comprising an inducible promoter directing expression of another gene product, (5) chemical inducers of expression, and (6) the multimeric coexpression product. FIG. 3 shows a schematic representation similar to that shown in FIG. 1, with inducible promoters ((3) and (4)) and the coding sequences for the products expressed by the inducible promoters present on the same expression vector.

Figure 2:
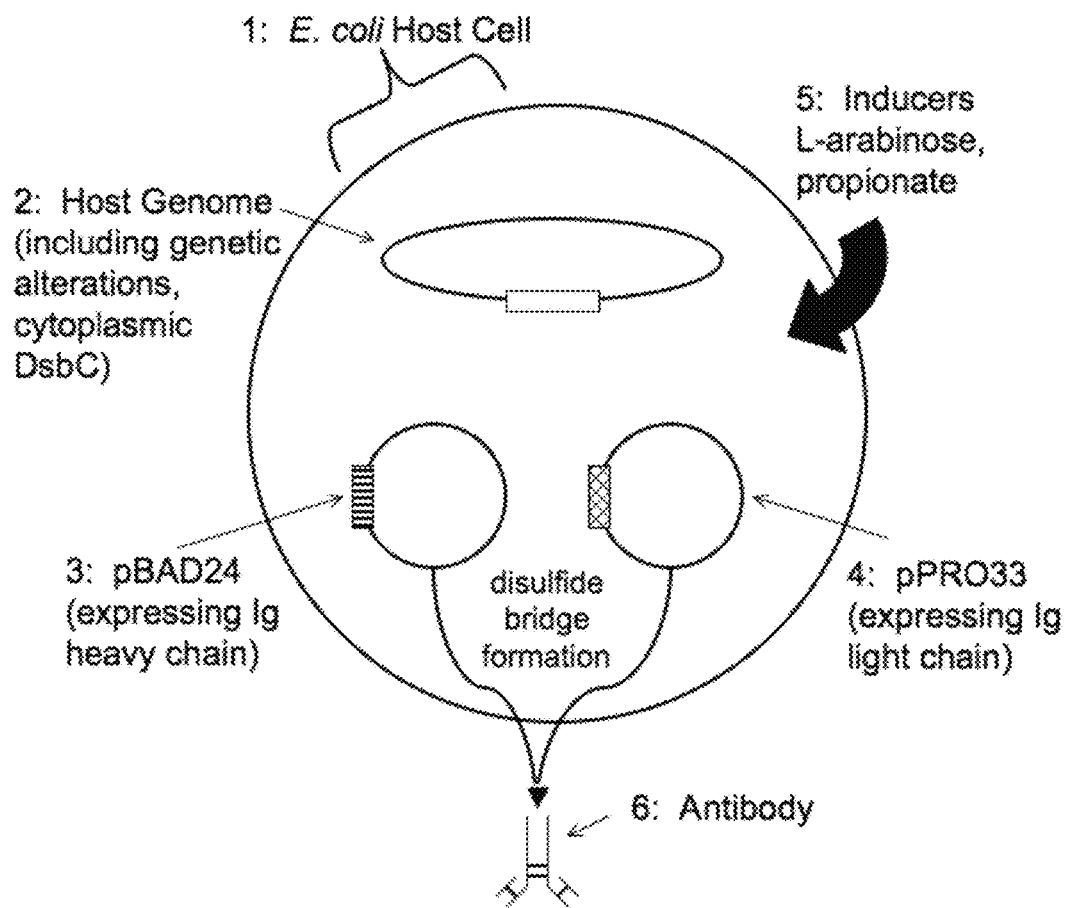
FIG. 2 is a schematic illustration of a particular use of the inducible coexpression system, in which the *E. coli* host cell genome (2) encodes a cytoplasmic form of the disulfide isomerase DsbC which lacks a signal peptide; the expression vector pBAD24 (or another expression vector containing an L-arabinose-inducible promoter, such as pBAD240) (3) provides L-arabinose-inducible expression of an immunoglobulin heavy chain, and the expression vector pPRO33 (or another expression vector containing a propionate-inducible promoter, such as pPRO43, pPRO430, pPRO430 (CloDF13), pPRO44, or pPRO45) (4) provides propionate-inducible expression of an immunoglobulin light chain; forming upon induction (5) the multimeric antibody product (6).

FIG. 2 shows a schematic representation of a particular example of an inducible coexpression system of the invention, utilizing the araBAD promoter on a pBAD24 (or pBAD240) expression vector in combination with a propionate-inducible promoter (prpBCDE promoter) on a pPRO33 (U.S. Pat. No. 8,178,338 B2; May 15, 2012; Keasling, Jay) (or pPRO43, pPRO430, pPRO430 (CloDF13), pPRO44, or pPRO45) expression vector in an E. coli host cell housing the appropriate genomic alterations which allow for homogenously inducible expression. In this manner, tight control and optimization of expression of each component of a multimeric product can be achieved for use in a number of coexpression applications. In this embodiment, the host cell (1) is the Gram-negative bacterium Escherichia coli, commonly used in the art for protein expression. The host genome (2) is the genome of the host cell organism with mutations or other alterations that facilitate homogenously inducible protein coexpression, including expression of a cytoplasmic form of the disulfide isomerase DsbC which lacks a signal peptide. In one embodiment, the genomic alterations include both an araBAD operon knockout mutation, and either expression of araE and araFGH from constitutive promoters, or a point mutation in the lacY gene (A117C) in an araEFGH-deficient background, to facilitate homogenous induction of plasmid-based ara promoters with exogenously applied L-arabinose, and also an inactivated proprionate metabolism gene, prpD, to facilitate homogenous induction of plasmid-based propionate promoters with exogenously applied propionate, which is converted to 2-methylcitrate in vivo.

Other genomic alterations that are useful for the inducible coexpression system, and may be introduced into the host cell, include without limitation: targeted inactivation of the scpA-argK-scpBC operon, to reduce background expression from the prpBCDE promoter; expression of the transcriptional regulator (prpR) for the less-preferred carbon-source (propionate) from an L-arabinose-inducible promoter such as the araBAD promoter, and/or an eliminated or reduced gene function for genes involved in the CCR system, such as crr and/or ptsG, to avoid suppression by the CCR system of induction by propionate in the presence of L-arabinose; reductions in the level of gene function for glutathione reductase (gor) or glutathione synthetase (gshB), together with thioredoxin reductase (trxB), and/or expression of yeast mitochondrial sulfhydryl oxidase Erv1p in the host cell cytoplasm, to provide a less strongly reducing environment in the host cell cytoplasm and promote disulfide bond formation; increased levels of expression, such as from a strong constitutive promoter, of chaperone proteins such as DnaK/DnaJ/GrpE, DsbC/DsbG, GroEL/GroES, IbpA/IbpB, Skp, Tig (trigger factor), and/or FkpA; and other mutations to reduce endogenous protease activity (such as that of the Lon and OmpT proteases) and recombinase activities.

As shown in FIG. 2, two compatible expression vectors (3, 4) are maintained in the host cell to allow for simultaneous expression (coexpression) of two different gene products. In this embodiment, one expression vector ('L-arabinose-induced expression vector') contains an L-arabinose-induced promoter, and is similar or identical to pBAD or related plasmids in which an araBAD promoter drives expression of an inserted expression sequence cloned into the multiple cloning site (MCS). The L-arabinose-induced expression vector also contains a coding sequence for an antibiotic-resistance gene (such as the Tn3 bla gene, which encodes beta-lactamase and confers resistance to ampicillin, or a gene encoding aminoglycoside 3'-phosphotransferase and conferring resistance to kanamycin) to facilitate selection of host cells (bacterial colonies) which contain an intact expression vector. An origin of replication (ORI) is required for propagation of the plasmid within bacterial host cells. The L-arabinose induced expression plasmid also contains a polynucleotide sequence encoding araC, a transcriptional regulator that allows for L-arabinose induction of the araBAD promotor and through transcriptional repression reduces 'leaky' background expression in the non-induced state. The other expression vector ('propionate-induced expression vector') is similar or identical to pPRO or related plasmids, in which a propionate-induced promoter drives expression of an inserted expression sequence cloned into the multiple cloning site (MCS). The plasmid also contains a coding sequence for an antibiotic-resistance gene (such as the cat gene, encoding chloramphenicol acetyltransferase, which confers resistance to chloramphenicol) to facilitate selection of host cells which contain an intact expression vector. An origin of replication (ORI) is required for propagation of the plasmid within bacterial host cells. In addition, the propionate-induced expresssion vector contains a polynucleotide sequence encoding prpR, a transcriptional regulator that allows for propionate (2-methylcitrate) induction of the prpBCDE promotor and reduces 'leaky' background expression in the non-induced state. To facilitate separate titratation of induction, plasmid compatibility, and copropagation of the expression vectors, it is useful for the expression vectors to contain promoters responsive to different inducers, compatible origins of replication, and different antibiotic-resistance markers. In one embodiment of the invention, pBAD24 (pMB1 or 'pBR322' ORI, Amp$^R$) or a related expression vector such as pBAD240 (pMB1 ORI, Kan$^R$) containing an L-arabinose-inducible araBAD promoter is combined in a host cell with a pPRO33, pPRO43, pPRO430, or related expression vector (p15A ORI, Cm$^R$) containing a propionate-inducible prpBCDE promoter. Compatible expression vectors containing a propionate-inducible prpBCDE promoter such as pPRO430(CloDF13), pPRO44 (RSF1030 ORI), or pPRO45 (CloDF13) can also be used in combination with the araBAD-promoter-containing expression vectors (pMB1 ORI). The expression vectors are co-propagated and maintained using growth medium supplemented with the appropriate antibiotics: ampicillin, chloramphenicol, and/or kanamycin. In one embodiment, one expression vector comprises a polynucleotide sequence encoding the heavy chain of a full-length antibody, and the other expression vector comprises a polynucleotide sequence encoding the light chain of a full-length antibody, each coding sequence cloned in-frame into the MCS of the respective expression vector. For production of certain gene products such as antibodies, coding sequence optimization for the host organism (including adjustment for codon bias and GC-content, among other considerations) will determine the coding sequences to be inserted into the expression constructs of the coexpression system.

Referring again to FIG. 2, coexpression of gene products is induced by inexpensive exogenously applied chemical metabolites, L-arabinose and propionate (5). The level of induction of expression of each gene product is independently titrated with its own chemical inducer, thereby facilitating optimization of protein coexpression. This is useful for expression of protein complexes and proteins that require a binding partner for stabilization, and may facilitate expression of otherwise difficult to express proteins, such as those with poor solubility or cellular toxicity. In this example, upon induction, antibody heavy and short chains are each separately expressed, then the proteins join and form interchain disulfide bridges (within the cytoplasm of the bacterial host) which allows the formation and stabilization of full-length antibody comprised of the heavy and light chains. Proteins can be directed to various compartments of the host organism. For example, in *E. coli* the protein can be expressed in the cytoplasm, cell membrane, periplasm, or secreted into the medium. After an appropriate incubation time, cells and media are collected, and the total protein extracted, which includes the coexpressed gene products (6). After extraction, the desired product can be purified using a number of methods well known in the art depending on the nature of the gene products produced in the coexpression system (for example liquid chromatography). In the example shown in FIG. 2, the multimeric product (full-length antibody) is extracted and purified using chromatographic methods. Purified intact antibody is visualized on a non-denaturing gel using standard techniques, including protein-binding dyes or immunohistochemistry. The full-length antibody product can then be used for a number of research, diagnostic, or other applications.

Figure 4:
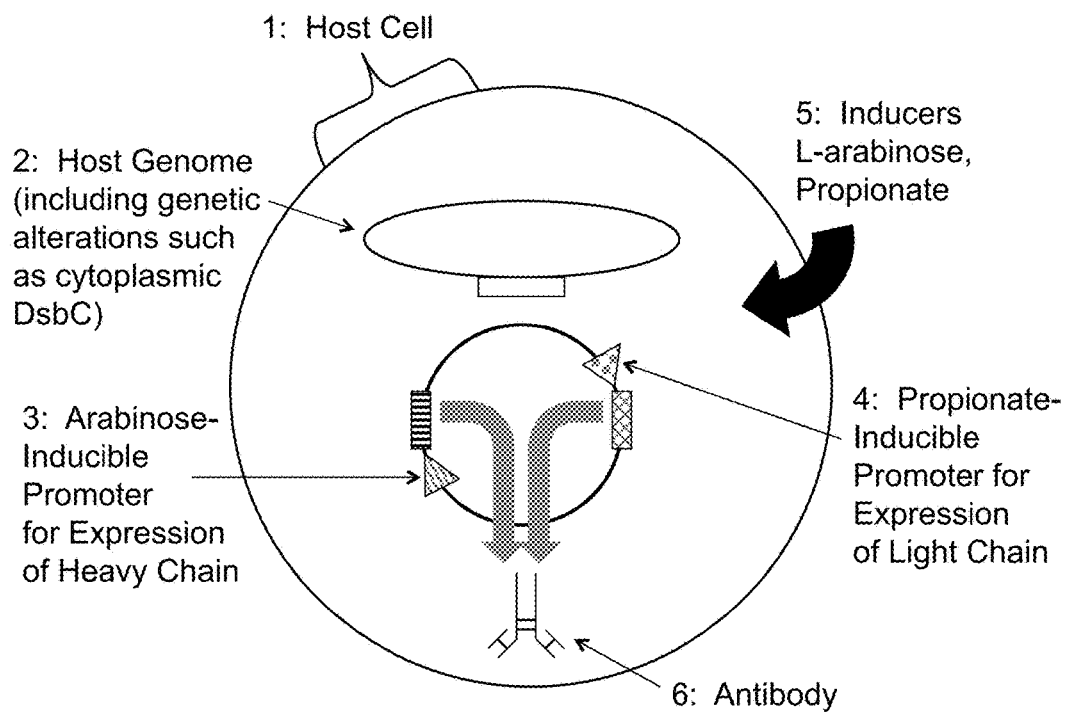
FIG. 4 is a schematic illustration of a particular use of the inducible coexpression system, in which the *E. coli* host cell genome (2) includes genetic alterations such as a cytoplasmic form of the disulfide isomerase DsbC which lacks a signal peptide; a multiple-promoter expression vector such as pSOL provides (3) L-arabinose-inducible expression of an immunoglobulin heavy chain and (4) propionate-inducible expression of an immunoglobulin light chain; forming upon induction (5) the multimeric antibody product (6).

FIG. 4 shows a schematic representation similar to that shown in FIG. 2, with an arabinose-inducible promoter (3), a propionate-inducible promoter (4), and coding sequences for antibody heavy and light chains present on the same expression vector. It is also possible to express the antibody heavy chain from the propionate-inducible promoter and the antibody light chain from the arabinose-inducible promoter.

Products Made by the Methods of the Invention

There is broad versatility in utilizing the inducible coexpression systems of the present invention in numerous coexpression applications, and in the properties of the products.

Glycosylation.

Gene products coexpressed by the methods of the invention may be glycosylated or unglycosylated. In one embodiment of the invention, the coexpressed gene products are polypeptides. Glycosylated polypeptides are polypeptides that comprise a covalently attached glycosyl group, and include polypeptides comprising all the glycosyl groups normally attached to particular residues of that polypeptide (fully glycosylated polypeptides), partially glycosylated polypeptides, polypeptides with glycosylation at one or more residues where glycosylation does not normally occur (altered glycosylation), and polypeptides glycosylated with at least one glycosyl group that differs in structure from the glycosyl group normally attached to one or more specified residues (modified glycosylation). An example of modified glycosylation is the production of "defucosylated" or "fucose-deficient" polypeptides, polypeptides lacking fucosyl moieties in the glycosyl groups attached to them, by expression of polypeptides in host cells lacking the ability to fucosylate polypeptides. Unglycosylated polypeptides are polypeptides that do not comprise a covalently bound glycosyl group. An unglycosylated polypeptide can be the result of deglycosylation of a polypeptide, or of production of an aglycosylated polypeptide. Deglycosylated polypeptides can be obtained by enzymatically deglycosylating glycosylated polypeptides, whereas aglycosylated polypeptides can be produced by expressing polypeptides in host cells that do not have the capability to glycosylate polypeptides, such as prokaryotic cells or cells in which the function of at least one glycosylation enzyme has been eliminated or reduced. In a particular embodiment, the coexpressed polypeptides are aglycosylated, and in a more specific embodiment, the aglycosylated polypeptides are coexpressed in prokaryotic cells such as E. coli.

Other Modifications of Gene Products.

Gene products coexpressed by the methods of the invention may be covalently linked to other types of molecules. Examples of molecules that may be covalently linked to coexpressed gene products, without limiting the scope of the invention, include polypeptides (such as receptors, ligands, cytokines, growth factors, polypeptide hormones, DNA-binding domains, protein interaction domains such as PDZ domains, kinase domains, antibodies, and fragments of any such polypeptides); water-soluble polymers (such as polyethylene glycol (PEG), carboxymethylcellulose, dextran, polyvinyl alcohol, polyoxyethylated polyols (such as glycerol), polyethylene glycol propionaldehyde, and similar compounds, derivatives, or mixtures thereof); and cytotoxic agents (such as chemotherapeutic agents, growth-inhibitory agents, toxins (such as enzymatically active toxins of bacterial, fungal, plant, or animal origin, or fragments thereof), and radioactive isotopes).

In addition, gene products to be coexpressed by the methods of the invention can be designed to include molecular moieties that aid in the purification and/or detection of the gene products. Many such moieties are known in the art; as one example, a polypeptide gene product can be designed to include a polyhistidine 'tag' sequence—a run of six or more histidines, preferably six to ten histidine residues, and most preferably six histidines—at its N- or C-terminus. The presence of a polyhistidine sequence on the end of a polypeptide allows it to be bound by cobalt- or nickel-based affinity media, and separated from other polypeptides. The polyhistidine tag sequence can be removed by exopeptidases. As another example, fluorescent protein sequences can be expressed as part of a polypeptide gene product, with the amino acid sequence for the fluorescent protein preferably added at the N- or C-terminal end of the amino acid sequence of the polypeptide gene product. The resulting fusion protein fluoresces when exposed to light of certain wavelengths, allowing the presence of the fusion protein to be detected visually. A well-known fluorescent protein is the green fluorescent protein of Aequorea victoria, and many other fluorescent proteins are commercially available, along with nucleotide sequences encoding them.

Antibodies.

In one embodiment of the invention, the coexpressed gene products are antibodies. The term 'antibody' is used in the broadest sense and specifically includes 'native' antibodies, fully-human antibodies, humanized antibodies, chimeric antibodies, multispecific antibodies (such as bispecific antibodies), monoclonal antibodies, polyclonal antibodies, antibody fragments, and other polypeptides derived from antibodies that are capable of binding antigen. Unless indicated otherwise herein, the numbering of the residues in an immunoglobulin heavy chain ('EU numbering') is that of the EU index (the residue numbering of the human IgG1 EU antibody) as in Kabat et al., Sequences of Proteins of Immunological Interest, Fifth Edition, 1991, National Institute of Health, Bethesda, Md.

'Native' antibodies are usually heterotetrameric glycoproteins of about 150,000 daltons, composed of two identical light (L) chains and two identical heavy (H) chains. Each light chain is linked to a heavy chain by one covalent disulfide bond, while the number of inter-chain disulfide linkages varies among the heavy chains of different immunoglobulin isotypes. Each heavy and light chain also has regularly spaced intrachain disulfide bridges. Each heavy chain has at its N-terminal end a variable domain ($V_H$) followed by a number of constant domains. Each light chain has a variable domain at it N-terminal end ($V_L$) and a constant domain at its C-terminal end; the constant domain of the light chain is aligned with the first constant domain of the heavy chain, and the light-chain variable domain is aligned with the variable domain of the heavy chain. The term 'variable' refers to the fact that certain portions of the variable domains differ extensively in sequence among antibodies and are used in the binding and specificity of each particular antibody for an antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, connected by three HVRs, and with the HVRs from the other chain, contribute to the formation of the antigen-binding site of antibodies.

The term 'Fc region' refers to a C-terminal region of an immunoglobulin heavy chain, and includes native Fc regions and variant Fc regions. Although the boundaries of the Fc region of an immunoglobulin heavy chain might vary, the human IgG heavy-chain Fc region can be defined to stretch from an amino acid residue at position Cys226, or from Pro230, to the carboxyl-terminus thereof. Alternatively, the Fc region can be defined to extend from the N-terminal residue (Ala231) of the conserved $C_H2$ immunoglobulin domain to the C-terminus, and may include multiple conserved domains such as $C_H2$, $C_H3$, and $C_H4$. The C-terminal lysine (residue 447 according to the EU numbering system) of the native Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. The Fc region of an antibody is crucial for recruitment of immunological cells and antibody dependent cytotoxicity (ADCC). In particular, the nature of the ADCC response elicited by antibodies depends on the interaction of the Fc region with receptors (FcRs) located on the surface of many cell types. Humans contain at least five different classes of Fc receptors. The binding of an antibody to FcRs determines its ability to recruit other immunological cells and the type of cell recruited. Hence, the ability to engineer antibodies with altered Fc regions that can recruit only certain kinds of cells can be critically important for therapy (US Patent Application 20090136936 A1, May 28, 2009, Georgiou, George). Native antibodies produced by mammalian cells typically comprise a branched, biantennary oligosaccharide that is generally attached by an N-linkage to Asn297 of the CH2 domain of the Fc region. In certain embodiments, antibodies produced by the methods of the invention are not glycosylated or are aglycosylated, for example, due to a substitution at residue 297 of the Fc region, or to expression in a host cell that does not have the capability to glycosylate polypeptides. Due to altered ADCC responses, unglycosylated antibodies may stimulate a lower level of inflammatory responses such as neuroinflammation. Also, since an antibody having an aglycosylated Fc region has very low binding affinity for Fc receptors, such antibodies would not bind to the large number of immune cells that bear these receptors. This is a significant advantage since it reduces non-specific binding, and also increases the half-life of the antibody in vivo, making this attribute very beneficial in therapeutics.

The terms 'full-length antibody', 'intact antibody', and 'whole antibody' are used interchangeably to refer to an antibody in its substantially intact 'native' form, not antibody fragments as defined below. The terms particularly refer to an antibody with heavy chains that each comprise a variable domain and an Fc region. 'Antibody fragments' comprise a portion of an intact antibody, preferably comprising the antigen-binding region thereof. Examples of antibody fragments include Fab, Fab', F(ab')$_2$, Fc, Fd, and Fv fragments; diabodies; linear antibodies; single-chain antibody molecules such as scFv; and multispecific antibodies formed from antibody fragments.

A 'human antibody' is one that possesses an amino-acid sequence corresponding to that of an antibody produced by a human. A 'chimeric' antibody is one in which a portion of the heavy and/or light chain is identical to, or shares a certain degree of amino acid sequence identity with, corresponding sequences in antibodies derived from a particular species or belonging to a particular antibody class or subclass, while the remainder of the chain(s) is identical to, or shares a certain degree of amino acid sequence identity with, corresponding sequences in antibodies derived from another species or belonging to another antibody class or subclass, as well as fragments of such antibodies. A 'humanized' antibody is a chimeric antibody that contains minimal amino acid residues derived from non-human immunoglobulin molecules. In one embodiment, a humanized antibody is a human immunoglobulin (recipient antibody) in which HVR residues of the recipient antibody are replaced by residues from an immunoglobulin HVR of a non-human species (donor antibody) such as mouse, rat, rabbit, or nonhuman primate. In some instances, FR residues of the human recipient antibody are replaced by corresponding non-human residues. Furthermore, humanized antibodies may comprise residues that are not found in the recipient antibody or in the donor antibody. The term 'monoclonal antibody' refers to an antibody obtained from a population of substantially homogeneous antibodies, in that the individual antibodies comprising the population are identical except for possible mutations, such as naturally occurring mutations, that may be present in minor amounts. Thus, the modifier 'monoclonal' indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against the same single determinant on an antigen. In addition to their specificity, monoclonal antibody preparations are advantageous in that they are typically uncontaminated by other immunoglobulins.

The 'binding affinity' of a molecule such as an antibody generally refers to the strength of the sum total of non-covalent interactions between a single binding site of a molecule and its binding partner (such as an antibody and the antigen it binds). Unless indicated otherwise, 'binding affinity' refers to intrinsic binding affinity that reflects a 1:1 interaction between members of a binding pair (such as antibody and antigen). The affinity of a molecule X for its partner Y can generally be represented by the dissociation constant (Kd). Low-affinity antibodies (higher Kd) generally bind antigen slowly and tend to dissociate readily, whereas high-affinity antibodies (lower Kd) generally bind antigen faster and tend to remain bound longer. A variety of ways to measure binding affinity are known in the art, any of which can be used for purposes of the present invention. Specific illustrative methods for measuring binding affinity are described in Example 8. Antibodies and antibody fragments produced by and/or used in methods of the invention preferably have binding affinities of less than 100 nM, more preferably have binding affinities of less than 10 nM, and most preferably have binding affinities of less than 2 nM, as measured by a surface-plasmon resonance assay as described in Example 8.

Antibodies (Secondary) that Recognize Aglycosylated Antibodies.

Production of antibodies in *E. coli*-based or other prokaryotic expression systems without glycosylation enzymes will generally yield aglycosylated antibodies, which can be used as primary antibodies. In addition to using the inducible coexpression systems of the invention to produce aglycosylated primary antibodies, the inducible coexpression systems of the invention can also be used to efficiently produce secondary antibodies that specifically recognize aglycosylated primary antibodies. One aspect of the present invention is a secondary antibody system capable of detecting an unglycosylated or aglycosylated primary antibody for research, analytic, diagnostic, or therapeutic purposes. As one example, a secondary antibody system is provided with the following components: epitope, primary antibody, secondary antibody, and detection system. The epitope is a portion of an antigen (usually a protein) which is the antigenic determinant that produces an immunological response when introduced into a live animal or is otherwise recognizable by an antibody. In practice, the epitope of interest may be present within a mixture or a tissue. In one embodiment, the epitope is a protein expressed in carcinoma cells in human tissue. The primary antibody is an antibody fragment, a single full-length antibody (monoclonal), or a mixture of different full-length antibodies (polyclonal), which recognizes and binds to the epitope, and preferably binds specifically to the epitope. A full-length antibody in this example comprises two heavy polypeptide chains and two light polypeptide chains joined by disulfide bridges. Each of the chains comprises a constant region (Fc) and a variable region (Fv). There are two antigen binding sites in the full-length antibody. In one embodiment of the present invention, the primary antibody is a full-length aglycosylated antibody (such as that produced in an *E. coli*-based expression system) which recognizes and binds an epitope of interest. The secondary antibody is an antibody fragment, a single full-length antibody (monoclonal), or a mixture of different full-length antibodies (polyclonal), which recognizes and binds to the aglycosylated primary antibody, and preferably binds specifically to the aglycosylated primary antibody. In one embodiment of the present invention, the secondary antibody is a full-length antibody which recognizes and binds the aglycosylated Fc portion of a full-length primary antibody. In this case, the antibody binding sites are selected and/or engineered to specifically recognize the Fc portion of the aglycosylated primary antibody, with or without the C-terminal lysine residue. In other embodiments, the secondary antibody could be engineered to recognize additional regions (epitopes) of the aglycosylated primary antibody, or additional engineered epitopes including but not limited to polypeptide sequences covalently attached to the primary antibody. The secondary antibody can be directed at single or multiple sites (epitopes) present on full-length aglycosylated antibodies molecules (including various immunoglobulin classes such as IgG, IgA, etc.) or antibody fragments such as Fc or Fab. Therefore, some secondary antibodies generated in this way would have broad specificity for any aglycosylated full-length antibody. The primary and secondary antibodies of the present invention can also include those produced by traditional methods (polyclonal antibody production using immunized rabbits or monoclonal antibody production using mouse hybridomas) and recombinant DNA technology such as phage display methods for identifying antigen-binding polypeptides.

Detection systems generally comprise an agent that is linked to or which binds the secondary antibody, enabling detection, visualization, and/or quantification of the secondary antibody. Various detection systems are well known in the art including but not limited to fluorescent dyes, enzymes, radioactive isotopes, or heavy metals. These may or may not involve direct physical linkage of additional polypeptides to the secondary antibody. Applications of this secondary antibody system include but are not limited to immunohistochemistry, Western blotting, and enzyme-linked immunosorbent assay (ELISA). For example, in one embodiment for use in immunohistochemistry, the epitope of interest would be present on a thin section of tissue, then an aglycosylated primary antibody would be applied to the tissue and allowed to bind the epitope. The unbound primary antibody would be removed, and then a secondary antibody capable of specifically binding the aglycosylated primary antibody is applied to the tissue and allowed to bind to the primary antibody. The unbound secondary antibody would be removed, and then detection system reagents applied. For example, if the secondary antibody were linked to an enzyme, then colorigenic enzymatic substrates would be applied to the tissue and allowed to react. Direct microscopic or fluoroscopic visualization of the reactive enzymatic substrates could then be performed. Other detection methods are well known in the art. The advantages of a system using secondary antibodies that recognize aglycosylated antibodies include, without limitation, the following: 1) increased specificity in immunohistochemistry because the secondary antibody is designed to bind the aglycosylated Fc portion of the primary antibody which is not otherwise present in eukaryotic tissues; 2) decreased background staining because of increased specificity for the primary antibody; 3) decreased cost of secondary antibody system production because the primary and/or secondary antibodies can be generated in prokaryotes such as *E. coli*; and 4) avoiding unnecessary utilization of mammals, including mice and rabbits, because the entire process of antibody development can be performed in prokaryotes such as *E. coli*.

Enzymes Used in Industrial Applications.

Many industrial processes utilize enzymes that can be produced by the methods of the invention. These processes include treatment of wastewater and other bioremediation and/or detoxification processes; bleaching of materials in the paper and textile industries; and degradation of biomass into material that can be fermented efficiently into biofuels. In many instances it would be desirable to produce enzymes for these applications in microbial host cells or preferably in bacterial host cells, but the active enzyme is difficult to express in large quantities due to problems with enzyme folding and/or a requirement for a cofactor. In certain embodiments of the invention, the inducible coexpression methods of the invention are used to produce enzymes with industrial applications, such as arabinose- and xylose-utilization enzymes (e.g. xylose isomerase (EC 5.3.1.5)) or lignin-degrading peroxidases (e.g. lignin peroxidase (EC 1.11.1.14), manganese peroxidase (EC 1.11.1.13), versatile peroxidase (EC 1.11.1.16), or laccase (EC 1.10.3.2)).

Example 1

Introduction of Genomic Alterations into Host Cells to Facilitate Coexpression

As described above, certain changes in host cell gene expression can improve the coexpression of the desired gene product(s). Certain host cells, *E. coli* ASE(DGH) cells, were derived from *E. coli* SHuffle® Express cells, and their genotype can be expressed as: *E. coli* SHuffle® Express ΔaraBAD Δsbm-ygfDGH ΔaraEp::J23104. The *E. coli* ASE (DGH) cells were produced as follows: deletions and alterations were made in the *E. coli* SHuffle® Express host cell genome by Gene Bridges GmbH (Heidelberg, Germany) using a recombineering method, described as deletion by counterselection, that seamlessly removes genomic sequences. A deletion of the host cell araBAD operon was made to reduce arabinose catabolism by the host cell, so that more of the arabinose inducer will be available for induction of a coexpressed gene product from an expression construct comprising the araBAD promoter. This deletion removes 4269 basepairs of the araBAD operon, corresponding to position 70,135 through 65,867 (minus strand) of the *E. coli* genome (positions within genomic nucleotide sequences are all given as in Table 1), so that most of the native araBAD promoter through all but a few codons of the AraD coding region are removed. The nucleotide sequence (minus strand) around the deletion junction (position 70,136|position 65,866) is: TTAT|TACG. Another deletion was made within the sbm-ygfDGH (also called scpA-argK-scpBC) operon, eliminating the function of genes involved in the biosynthesis of 2-methylcitrate, to increase sensitivity of the host cell's propionate-inducible promoter to exogenously supplied propionate. The sbm-ygfDGH deletion removes 5542 basepairs (position 3,058,754 through 3,064,295 of the *E. coli* genome), taking out the sbm-ygfDGH promoter and all of the operon except for the last codon of the ygfH coding sequence, while leaving the adjacent ygfI coding sequence and stop codon intact. The nucleotide sequence (plus strand) around the deletion junction (position 3,058,753|position 3,064,296) is: ACAA|GGGT. In addition to these deletions made in the *E. coli* SHuffle® Express host cell genome, Gene Bridges GmbH introduced a point mutation in the genomic rpsL gene coding sequence, which extends on the minus strand from position 3,472,574 through 3,472,200, changing the A at position 3,472,447 to a G, altering the codon for Lys43 to a codon for Arg, which results in a streptomycin-resistant phenotype when the mutant rpsL-Arg43 gene is expressed. Another alteration to the host cell genome, allowing for more tightly controlled inducible expression as described above, is to make the araE promoter constitutive rather than responsive to arabinose. Most of the native araE promoter, including CRP-cAMP and AraC binding sites, was removed by deleting 97 basepairs (position 2,980,335 through 2,980,239 (minus strand)) and replacing that sequence with the 35-basepair sequence of the constitutive J23104 promoter (SEQ ID NO:1; the nucleotide sequence of J23104 was obtained from the partsregistry.org website, parts.igem.org/Main_Page). The resulting junction site sequences within the altered araE promoter are: TGAA|TTGA . . . TAGC|TTCA. An *E. coli* host cell, such as an *E. coli* SHuffle® Express host cell, with any of these genomic alterations, or any combination of them, can be employed in the inducible coexpression of gene products.

Example 2

Expression Vectors Comprising an Inducible Promoter

A. Expression Vector pPRO43

The expression vector pPRO43 (SEQ ID NO:2) is used for expressing gene products of interest from the propionate-inducible prpBCDE promoter, and was constructed with reference to the nucleotide sequence of the pPRO33 expression vector. The nucleotide sequence of pPRO33 was compiled from the sequences of the pBAD18 vector (GenBank Accession No. X81838.1), the *E. coli* genomic sequence of the prpR-P$_{prpB}$ region, and the pBAD33 vector, as described in Guzman et al., "Tight regulation, modulation, and high-level expression by vectors containing the arabinose PBAD promoter", J Bacteriol 1995 July; 177(14): 4121-4130, and in U.S. Pat. No. 8,178,338 B2; May 15, 2012; Keasling, Jay. The nucleotide sequence of pPRO33 was confirmed by sequencing and is provided in SEQ ID NO:3.

In pPRO43 the nucleotide sequence encoding the transcriptional activator prpR has been optimized for expression in *E. coli* by DNA2.0 (Menlo Park, Calif.) using methods such as those described in Welch et al., "Design parameters to control synthetic gene expression in *Escherichia coli*", PLoS One 2009 Sep. 14; 4(9): e7002; doi: 10.1371/journal.pone.0007002. The optimized prpR sequences in pPRO43 include the RBS and other sequences upstream of the prpR coding sequence, which is nucleotides 1593 through 7 of SEQ ID NO:2, on the opposite strand from that shown. The pPRO43 vector also has only one HindIII restriction site, which is in the multiple cloning site (MCS), in contrast with pPRO33 which has two HindIII sites, one in the MCS and a second in the prpR coding sequence.

B. Expression Vectors pPRO430 and pPRO430 (CloDF13)

Expression vector pPRO430 (SEQ ID NO:4) was synthesized by DNA2.0, based on the nucleotide sequence of pPRO43 (SEQ ID NO:2). The pPRO430 vector is similar to pPRO43 in that both contain the p15 origin of replication, a gene conferring resistance to chloramphenical (Cm$^R$), the prpR coding sequence optimized for expression in *E. coli* described above, and a cloning site downstream of the propionate-inducible prpBCDE promoter into which a coding sequence can be inserted. The pPRO430 expression vector differs from pPRO43 in that it has an optimized RBS sequence—AGGAGGAAAACATA (nucleotides 3566-3579 of SEQ ID NO:4)—upstream of the cloning site. The pPRO430 expression vector has also been streamlined relative to pPRO43 by the removal of some nucleotide sequences and the use of shorter terminators, with the result that the pPRO430 nucleotide sequence (SEQ ID NO:4) has only 3698 bases, compared to the pPRO43 nucleotide sequence (SEQ ID NO:2) at 5883 bases. The pPRO430 (CloDF13) expression vector (SEQ ID NO:5) is identical to pPRO430 except that the p15 origin of replication in pPRO430, flanked by BfuAI restriction sites, is replaced by the higher-copy-number CloDF13 origin of replication in pPRO430(CloDF13).

C. Expression Vector pBAD240

The expression vector pBAD240 (SEQ ID NO:6) was synthesized by DNA2.0, based on the nucleotide sequence of pBAD24 (GenBank Database Accession No. X81837.1 (25 Oct. 1995)). The expression vector pBAD240 differs from pBAD24 in having an optimized RBS sequence—AGGAGGTAAAAA (nucleotides 3125-3136 of SEQ ID NO:6)—upstream of the cloning site into which a coding sequence can be inserted. The pBAD240 nucleotide sequence was also streamlined relative to pBAD24 by the removal of some nucleotide sequences and the use of shorter terminators, with the result that the pBAD240 nucleotide sequence (SEQ ID NO:C) has only 3255 bases, compared to the pBAD24 nucleotide sequence at 4542 bases. The pBAD240 expression vector also includes a gene conferring resistance to kanamycin (Kan$^R$), rather than the ampicillin-resistance gene that is in pBAD24.

D. Expression Vectors pPRO44 and pPRO45

Expression vectors pPRO44 (SEQ ID NO:7) and pPRO45 (SEQ ID NO:8) were created based on the nucleotide sequence of pPRO43 (SEQ ID NO:2), with different origins of replication to be used in the pPRO44 (RSF1030) and pPRO45 (CloDF13) expression vectors. Primers were designed for pPRO43, the RSF1030 origin of replication, and the CloDF13 origin of replication, in order to add a SpeI restriction site upstream and an AatII restriction site downstream of each origin of replication sequence. The pPRO43 and RSF1030 nucleotide sequences were amplified using those primers (SEQ ID Nos 9 and 10, and SEQ ID Nos 11 and 12, respectively), the amplified products were digested with SpeI and AatII, and the desired restriction fragments were gel purified and ligated together to create pPRO44 (SEQ ID NO:7). The resulting pPRO44 expression vector was sequenced to confirm that no mutations were introduced through PCR amplification. To create pPRO45, the CloDF13 nucleotide sequence was amplified using primers (SEQ ID Nos 13 and 14) to add SpeI and AatII sites, the CloDF13 amplification product and pPRO44 were digested with SpeI and AatII restriction enzymes and the desired fragments were gel purified, and then ligated together to form pPRO45 (SEQ ID NO:8). The CloDF13 portion of pPRO45 was sequenced to confirm that no mutations were introduced through PCR amplification.

Example 3

Use of Dual-Promoter Vector pSOL for Inducible Coexpression of Fluorescent Proteins in Bacterial Cells A. Construction of the Dual-Promoter pSOL Expression Vector.

Figure 5:
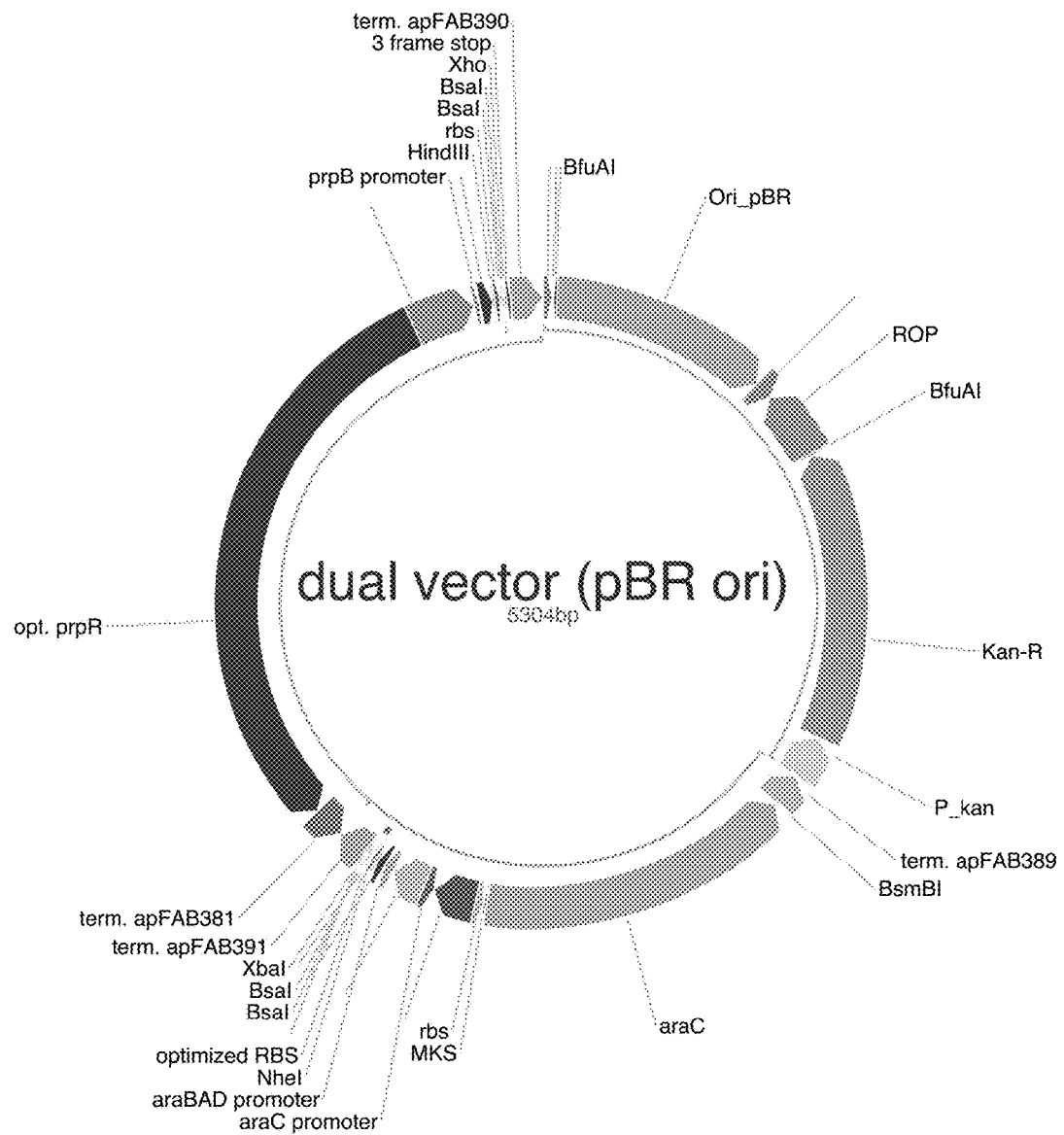
FIG. 5 is a schematic representation of a vector ("dual vector", also named "pSOL") for use in an inducible coexpression system.

An expression vector comprising two different inducible promoters, referred to as 'dual vector' or 'pSOL', is shown schematically in FIG. 5. This vector was synthesized by DNA2.0 (Menlo Park, Calif.) and contains several polynucleotide sequences, or 'elements', optimized for expression in E. coli host cells. A description of the polynucleotide elements utilized in pSOL is provided below as Table 4; the nucleotide sequence of pSOL is provided as SEQ ID NO:15.

TABLE 4

Polynucleotide Elements of pSOL Dual-Promoter Expression Vector

| Name of element: | Position of element in SEQ ID NO: 15 (or its complement): | Description of element: |
|---|---|---|
| BfuAI | complement (29-38) | BfuAI restriction site |
| Ori_pBR | 39-651 | pBR322 (pMB1) origin of replication |
| ROP | complement (703-894) | Coding sequence: E. coli regulatory protein rop (RNA one modulator rom) |
| BfuAI | 895-900 | BfuAI restriction site |
| Kan-R | complement (901-1710) | Coding sequence: kanamycin resistance protein |
| P_kan | complement (1711-1832) | Promoter for expression of kanamycin resistance protein |
| term. apFAB389 | complement (1833-1923) | Terminator apFAB389 (BIOFAB, Emeryville, California) |
| BsmBI | complement (1924-1929) | BsmBI restriction site |
| araC | complement (1930-2808) | Coding sequence: AraC transcriptional regulator protein |
| MKS | complement (2809-2817) | Coding sequence: MKS (methionine-lysine-serine) |
| rbs | complement (2818-2840) | Ribosome binding site |
| araC promoter | complement (2959-2987) | Promoter for expression of AraC |
| araBAD promoter | 3084-3111 | Promoter from araBAD operon for expression of inserted coding sequences |
| NheI | 3134-3139 | NheI restriction site |
| optimized RBS | 3140-3151 | Optimized ribosome binding site (as in pBAD240) |
| BsaI | complement (3158-3163) | BsaI restriction site |
| BsaI | 3164-3169 | BsaI restriction site |
| XbaI | 3172-3177 | XbaI restriction site |
| term. apFAB391 | 3178-3259 | Terminator apFAB391 (BIOFAB, Emeryville, California) |
| term. apFAB381 | complement (3260-3349) | Terminator apFAB391 (BIOFAB, Emeryville, California) |
| opt. prpR | complement (3350-4936) | Optimized coding sequence: PrpR transcriptional regulator protein |
| prpB promoter | 5114-5129 | Promoter from prpBCDE operon for expression of inserted coding sequences |
| HindIII | 5166-5171 | HindIII restriction site |
| rbs | 5172-5185 | Optimized ribosome binding site (as in pPRO430) |
| BsaI | complement (5186-5191) | BsaI restriction site |
| BsaI | 5192-5197 | BsaI restriction site |
| Xho | 5199-5204 | XhoI restriction site |
| 3 frame stop | 5205-5215 | Stop codons in all three forward reading frames |
| term. apFAB390 | 5216-5304 | Terminator apFAB390 (BIOFAB, Emeryville, California) |

In particular, the pSOL expression vector comprises two different inducible promoters that can be used for the inducible coexpression of proteins of interest: an arabinose-inducible araBAD promoter and a propionate-inducible prpBCDE promoter. Variants of pSOL can also be used for the inducible coexpression of proteins of interest, such as an expression vector based on pSOL in which the positions of the araBAD promoter and the prpBCDE promoter are switched relative to the origin of replication. Further useful variants of pSOL expression vectors include those in which the coding sequence for the AraC transcriptional activator and/or the coding sequence for the PrpR transcriptional activator are not present in the expression vector, but are instead expressed from a separate polynucleotide such as a different extrachromosomal element, or the host genome. Additional variants of pSOL expression vectors are those comprising a third inducible promoter inserted, for example, between pSOL nucleotide positions 5304 and 29 of SEQ ID NO:15, so that the third inducible promoter would be downstream of the prpB promoter and its associated cloning sites and terminator, and oriented in the same direction as the prpB promoter. The third inducible promoter in such variants of pSOL expression vectors could for example be a rhamnose-inducible promoter such as the rhaSR promoter, a xylose-inducible promoter such as the xylAB promoter, or a promoter inducible by phosphate depletion such as the phoA promoter.

B. Inducible Coexpression of Fluorescent Proteins.

To compare levels of coexpression from the dual-promoter pSOL vector with coexpression from a combination of pBAD24 and pPRO33 expression vectors, the pBAD24 and pPRO33 vectors were used to express a yellow fluorescent protein (YellowFP) and a red fluorescent protein (RedFP), respectively. The L-arabinose-inducible araBAD promoter in pSOL was used to express YellowFP, and the propionate-inducible prpBCDE promoter was used to express RedFP. The YellowFP has maximal emission at 528 nm-530 nm with excitation at 515 nm (Nagai et al., "A variant of yellow fluorescent protein with fast and efficient maturation for cell-biological applications", Nat Biotechnol 2002 January; 20(1): 87-90), and the RedFP has maximal emission at 610 nm with excitation at 587 nm (Shaner et al., "Improved monomeric red, orange and yellow fluorescent proteins derived from Discosoma sp. red fluorescent protein", Nat Biotechnol 2004 December; 22(12): 1567-1572; Epub 2004 Nov. 21).

To construct the pBAD24-YellowFP and pPRO33-RedFP plasmids, the coding sequences for YellowFP and RedFP were optimized for expression in E. coli by DNA 2.0. The optimized coding sequences for YellowFP and RedFP were digested with both NheI and SalI, and the digested inserts ligated into NheI/SalI-cut pBAD24 and pPRO33, respectively. In the case of pSOL, DNA2.0 used the amplification-based Electra cloning system to insert the optimized coding sequences for YellowFP and for RedFP into the pSOL expression vector downstream of the optimized ribosome binding sites in the araBAD promoter and prpBCDE promoter regions, respectively. The pBAD24-YellowFP and pPRO33-RedFP expression constructs were co-transformed into E. coli ASE(DGH) cells (E. coli ASE(DGH) cells are described in Example 1), and pSOL-YellowFP-RedFP expression constructs were also separately transformed into E. coli ASE(DGH) cells.

Cultures of pBAD24-YellowFP/pPRO33-RedFP in ASE (DGH) ('pBAD, pPRO') and pSOL-YellowFP-RedFP in ASE(DGH) ('pSOL') were grown overnight at 37 degrees C. with shaking at 275 RPM in LB medium containing chloramphenicol plus ampicillin or containing kanamycin, respectively. At an OD600 of 0.7, the cells were diluted in 2×6 mL of LB medium plus antibiotics to an OD600 of 0.01 and grown at 30 degrees C. with shaking at 275 RPM until reaching an OD600 of 0.75. Cells were pelleted at 3800×g for 7 minutes at 30 degrees C., and were resuspended in M9 medium plus antibiotics with no additional carbon source to an OD600 of 0.7. The resuspended cells were plated in a multi-well plate at 200 microliters per well as follows:

Rows A, B: pBAD24-YellowFP/pPRO33-RedFP in ASE (DGH) colony 1

Rows C, D: pBAD24-YellowFP/pPRO33-RedFP in ASE (DGH) colony 2

Rows E, F: pSOL-YellowFP-RedFP in ASE(DGH) colony 1

Row G, H: pSOL-YellowFP-RedFP in ASE(DGH) colony 2

Cells were induced by the addition of varying concentrations of propionate (by hand) and L-arabinose (by digital dispenser), with propionate concentrations of 0 mM, 1 mM, 2.5 mM, 5 mM, and 20 mM and L-arabinose concentrations of 0 micromolar, 0.67 micromolar, 3.33 micromolar, 6.66 micromolar, and 66.61 micromolar.

Figure 6:
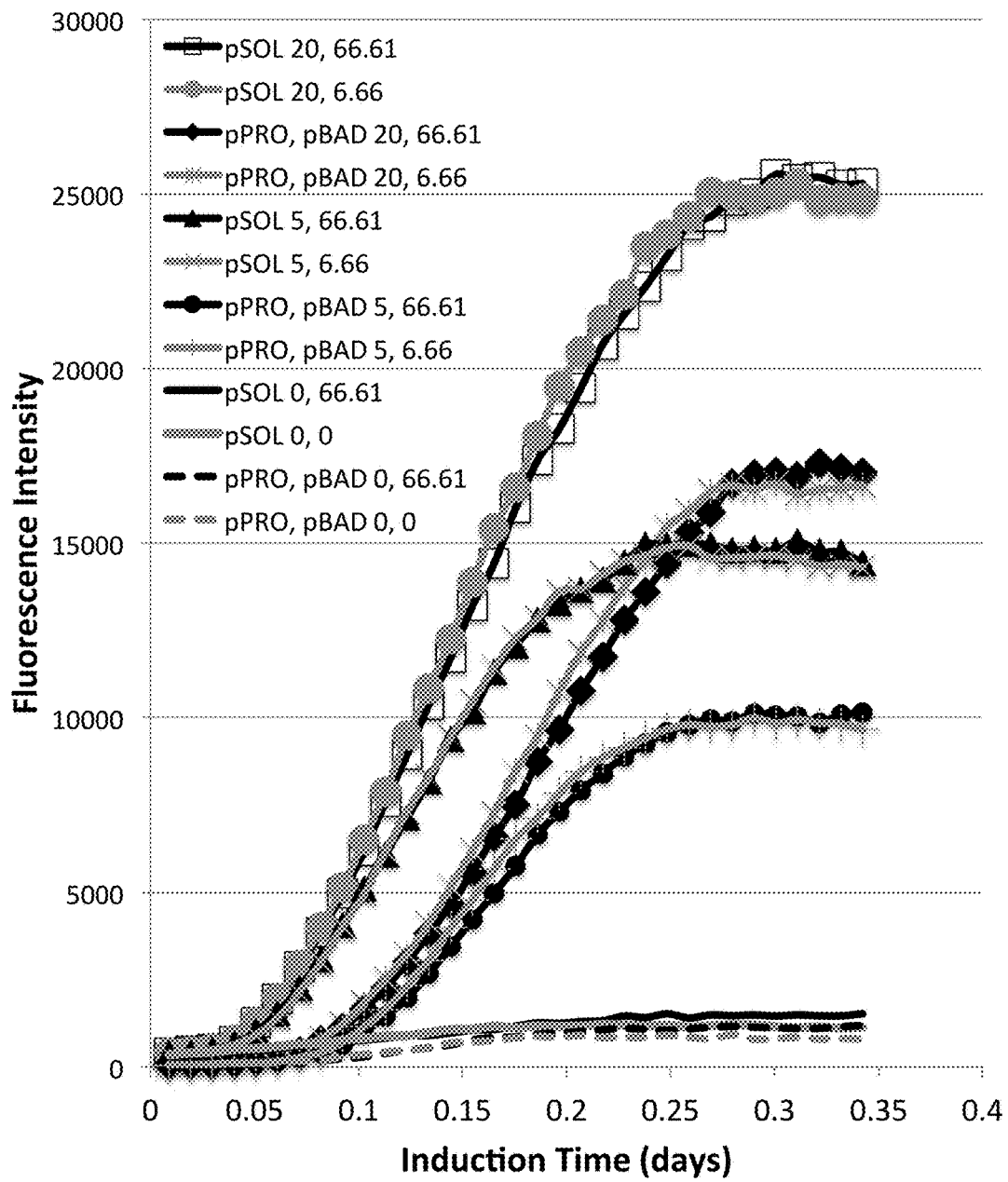
FIG. 6 shows a time course of coexpression of fluorescent proteins in bacterial cells; in this graph the fluorescence from a red fluorescent protein (RedFP), expressed from a propionate-inducible prpBCDE promoter, is shown. 'pSOL': pSOL-YellowFP-RedFP in *E. coli* ASE(DGH) cells. 'pPRO, pBAD': pBAD24-YellowFP/pPRO33-RedFP in *E. coli* ASE (DGH) cells. The inducer concentrations for each averaged group of samples are shown in the legend, with the propionate concentration listed first (0 mM, 5 mM, or 20 mM), followed by the L-arabinose concentration (0 micromolar, 6.66 micromolar, or 66.61 micromolar).
Figure 7:
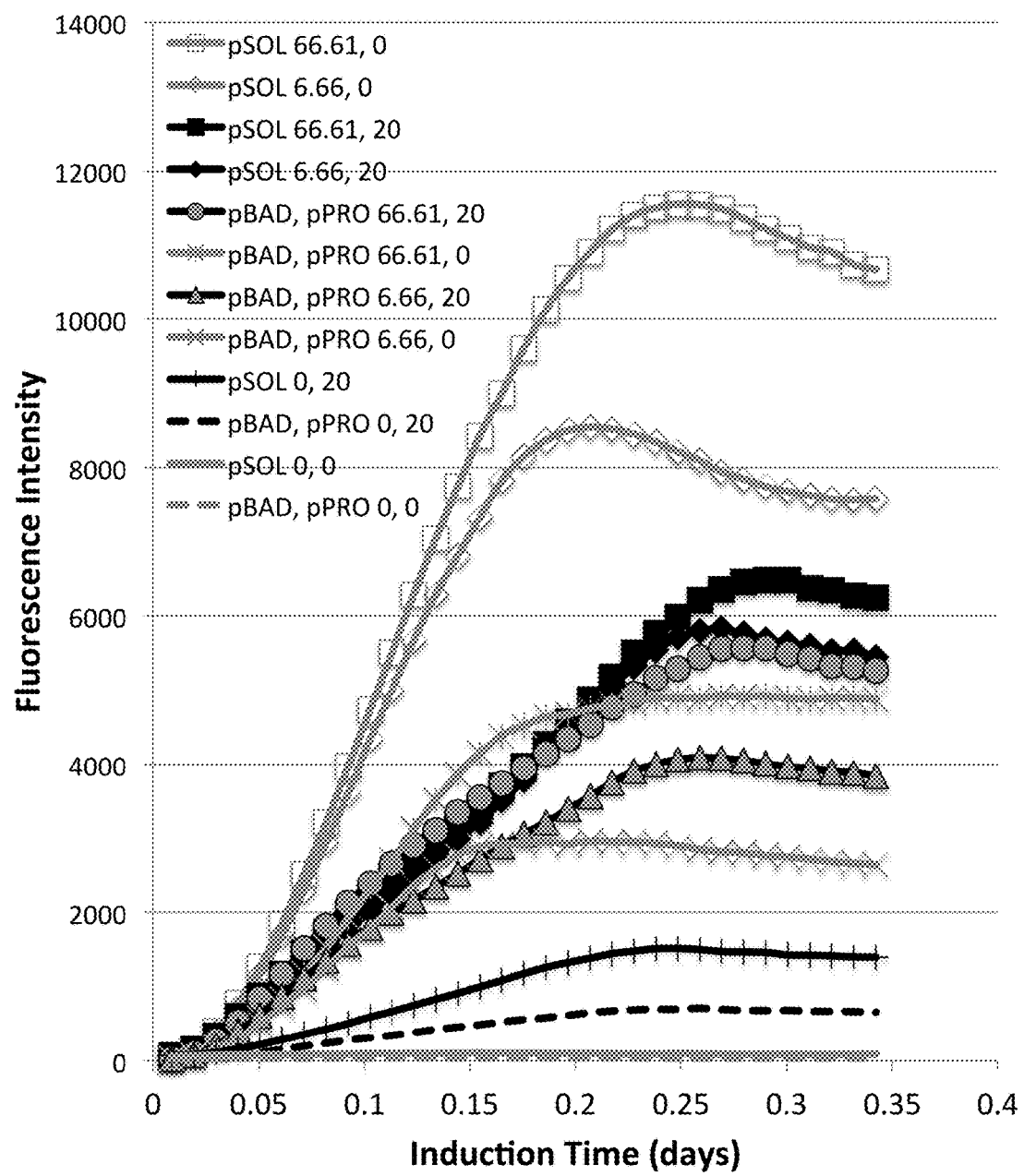
FIG. 7 shows a time course of coexpression of fluorescent proteins in bacterial cells; in this graph the fluorescence from a yellow fluorescent protein (YellowFP), expressed from an L-arabinose-inducible araBAD promoter, is shown. 'pSOL': pSOL-YellowFP-RedFP in *E. coli* ASE(DGH) cells. 'pBAD, pPRO': pBAD24-YellowFP/pPRO33-RedFP in *E. coli* ASE(DGH) cells. The inducer concentrations for each averaged group of samples are shown in the legend, with the L-arabinose concentration listed first (0 micromolar, 6.66 micromolar, or 66.61 micromolar), followed by the propionate concentration (0 mM, 5 mM, or 20 mM).

The plates were incubated in a Biotek Synergy™ 4 microplate reader (BioTek Instruments Inc., Winooski, Vt.) at 30 degrees C. using the "Fast" shake speed, and fluorescence was monitored every 15 minutes for 8 hours. Fluorescence values were averaged for samples cultured in the same inducer concentrations, and the fluorescence plotted over time as shown in FIGS. 6 and 7. FIG. 6 shows the levels of fluoresence from RedFP over time, expressed from a propionate-inducible prpBCDE promoter. The inducer concentrations for each averaged group of samples are shown in the legend, with the propionate concentration listed first, followed by the L-arabinose concentration. FIG. 7 shows the levels of fluoresence from YellowFP over time, expressed from an L-arabinose-inducible araBAD promoter. The inducer concentrations for each averaged group of samples are shown in the legend, with the L-arabinose concentration listed first, followed by the propionate concentration. For each combination of inducer concentrations, the expression of the fluorescent protein being measured, as indicated by the level of fluorescence observed, was higher from the inducible promoter present on the pSOL dual-promoter expression vector than from the corresponding inducible promoter present in the pBAD24-YellowFP/pPRO33-RedFP combination. This increased level of fluorescent protein expression from pSOL relative to pBAD24 and pPRO33 was observed not only for the combinations of inducer concentrations shown in FIGS. 6 and 7, but also for the combinations of inducer concentrations that were omitted from the graphs for the sake of clarity.

Example 4

Inducible Coexpression of Infliximab

Infliximab is a chimeric monoclonal antibody that binds to TNF-alpha, an inflammatory cytokine, and is used in the treatment of conditions that involve TNF-alpha such as autoimmune diseases (Crohn's disease, rheumatoid arthritis, psoriasis, etc.). Infliximab is formed from a heavy chain (amino acid sequence shown as SEQ ID NO:16) and a light chain (amino acid sequence shown as SEQ ID NO:17); each of these chains has a variable domain sequence derived from mouse anti-TNF-alpha antibodies, and a human constant domain. Codon optimization for expression in E. coli and synthesis of polynucleotides encoding SEQ ID NOs 16 and 17 was performed by DNA2.0 (Menlo Park, Calif.).

The DNA2.0 Electra cloning method (dna20.com) is used to create the infliximab expression constructs. The expression construct formed by inserting the optimized coding sequence for the infliximab heavy chain into the Electra cloning site of the pBAD240 expression vector is pBAD240-Infliximab_HC, which has the nucleotide sequence shown as SEQ ID NO:18. The expression construct formed by inserting the optimized coding sequence for the infliximab light chain into the Electra cloning site of the pPRO430 expression vector is pPRO430-Infliximab_LC, which has the nucleotide sequence shown as SEQ ID NO:19. Both the optimized infliximab heavy and light chain coding sequences were cloned into the pSOL expression vector (SEQ ID NO:15) in a similar way, with the heavy chain expressed from the araBAD promoter, and the light chain from the prpBCDE promoter. The resulting pSOL-Infliximab expression vector has the nucleotide sequence shown in SEQ ID NO:20. The pBAD240-Infliximab_HC and pPRO430-Infliximab_LC expression constructs are used to cotransform E. coli ASE(DGH) cells through heat shock at 42 degrees C., followed by growth at 37 degrees C. overnight, and the pSOL-Infliximab expression construct is similarly transformed into E. coli ASE(DGH) cells, creating ASE(DGH)(pBAD240-Infliximab_HC/pPRO430-Infliximab_LC) cells and ASE(DGH)(pSOL-Infliximab) cells.

These cells are grown generally as described in Example 3, including the addition of selective compounds such as kanamycin and/or chloramphenicol as needed, and for induction of antibody expression cells are resuspended in M9 medium with no additional carbon source at an OD600 of approximately 0.7 (0.6-1.0). The cells are then induced by addition of arabinose (initially at concentrations including 0.1%) and propionate (initially at concentrations including 50 mM). Adjustment of the concentrations of arabinose and propionate can be made as described in Example 5. After induction, the host cells in which antibodies have been produced are disrupted by chemical lysis using enzymes such as lysozyme, or by mechanical disruption methods such as sonication or microfluidization using a Microfluidics model M-110Y microfluidizer (Microfluidics International Corp., Westwood, Mass.). Centrifugation at 20,000×g for 15 minutes at room temperature is used to separate out the insoluble fraction, and the supernatant containing soluble protein including the expressed antibodies is collected.

The infliximab antibodies are detected and quantified using a capillary electrophoresis Western blot, run on a WES system (ProteinSimple, San Jose, Calif.), according to the manufacturer's instructions. Soluble protein extracts are loaded into the capillary set, proteins are electrophoretically separated by size, and then the antibodies in the samples are detected with a blocking step (instead of the use of a primary antibody), and incubation with an HRP-conjugated goat anti-human secondary antibody that recognizes human antibody heavy and light chains. Antibody detection is accomplished by addition of the chemiluminescent substrate to the capillary and the direct capture of the light emitted during the enzyme-catalyzed reaction. Molecular weight estimates are calculated using a standard curve generated using six biotinylated proteins ranging from 12 k to 230 kDa for each run. Fluorescent standards are included in the sample loading buffer, giving each sample an internal standard that is used to align the sample with the molecular weight standard.

To determine the amount of protein present at a given molecular weight, known amounts of a protein standard are run in some of the capillaries. In this case, serial dilutions are prepared of commerically available infliximab having a known protein concentration, starting for example at 10 micrograms/mL and diluted down to 1.0 nanograms/mL Approximately five WES system capillaries are used to run the serial dilution. For each infliximab protein band in both the experimental and the serial dilution capillaries, a curve is generated by the WES system software representing the protein band's chemiluminescence intensity, and the area under each curve is evaluated, with a standard curve of these areas plotted for the infliximab protein bands in the infliximab serial dilution capillaries. To determine the concentration of the experimental samples, the area under each curve representing the chemiluminescence intensity of an experimental infliximab sample can the compared to the standard curve generated for the samples of known infliximab concentration.

The infliximab antibodies can be further purified as described in Example 7, and additional characterization of the infliximab antibodies is described in Example 8 (measurement of antibody binding affinity) and Example 9 (characterizing the disulfide bonds present in coexpression products).

Example 5

Titration of Coexpression by Varying Inducer Concentration

To optimize production of a multimeric product using the inducible coexpression systems of the invention, it is possible to independently adjust or titrate the concentrations of the inducers. Host cells containing L-arabinose-inducible and propionate-inducible expression constructs are grown to the desired density (such as an $OD_{600}$ of approximately 0.5) in M9 minimal medium containing the appropriate antibiotics, then cells are aliquoted into small volumes of M9 minimal medium, optionally prepared with no carbon source such as glycerol, and with the appropriate antibiotics and varying concentrations of each inducer. The concentration of L-arabinose necessary to induce expression is typically less than 2%. In a titration experiment, the tested concentrations of L-arabinose can range from 2% to 1.5%, 1%, 0.5%, 0.2%, 0.1%, 0.05%, 0.04%, 0.03%, 0.02%, 0.01%, 0.005%, 0.002%, and 0.001%. The concentrations of L-rhamnose or D-xylose necessary to induce expression of L-rhamnose-inducible or D-xylose-inducible promoters are tested similarly, with the tested concentrations ranging from 5% to 0.01%. For each concentration 'x' of L-arabinose (or L-rhamnose or D-xylose) that is tested, the concentration of a different inducer such as propionate, added to each of the tubes containing concentration 'x' of the first inducer, is varied in each series of samples, which in the case of propionate range from 1 M to 750 mM, 500 mM, 250 mM, 100 mM, 75 mM, 50 mM, 25 mM, 10 mM, 5 mM, and 1 mM. Alternatively, titration experiments can start at a 'standard' combination of inducer concentrations, which is 0.002% of any of L-arabinose, L-rhamnose, or D-xylose, and/or 50 mM propionate, and test new combinations of inducer concentrations that vary from that of the 'standard' combination. Similar titration experiments can be performed with any combination of inducers used in an inducible coexpression system of the invention, including but not limited to L-arabinose, propionate, L-rhamnose, and D-xylose. After growth in the presence of inducers for 6 hours, the cells are pelleted, the desired product is extracted from the cells, and the yield of product per mass value of cells is determined by a quantitative immunological assay such as ELISA, or by purification of the product and quantification by UV absorbance at 280 nm.

It is also possible to titrate inducer concentrations using a high-throughput assay, in which the proteins to be expressed are engineered to include a fluorescent protein moiety, such as that provided by the mKate2 red fluorescent protein (Evrogen, Moscow, Russia), or the enhanced green fluorescent proteins from *Aequorea victoria* and *Bacillus cereus*. Another approach to determining the amount and activity of gene products produced by different concentrations of inducers in a high-throughput titration experiment, is to use a sensor capable of measuring biomolecular binding interactions, such as a sensor that detects surface plasmon resonance, or a sensor that employs bio-layer interferometry (BLI) (for example, an Octet® QK system from forteBIO, Menlo Park, Calif.).

Example 6

Measurement of the Strength of Promoters and the Homogeneity of Inducible Expression The strength of a promoter is measured as the amount of transcription of a gene product initiated at that promoter, relative to a suitable control. For constitutive promoters directing expression of a gene product in an expression construct, a suitable control could use the same expression construct, except that the 'wild-type' version of the promoter, or a promoter from a 'housekeeping' gene, is used in place of the promoter to be tested. For inducible promoters, expression of the gene product from the promoter can be compared under inducing and non-inducing conditions.

A. Measuring Promoter Strength Using Quantitative PCR to Determine Levels of RNA Transcribed from the Promoter The method of De Mey et al. ("Promoter knock-in: a novel rational method for the fine tuning of genes", BMC Biotechnol 2010 March 24; 10: 26) is used to determine the relative strength of promoters in host cells that can be grown in culture. Host cells containing an expression construct with the promoter to be tested, and control host cells containing a control expression construct, are grown in culture in triplicate. One-ml samples are collected at $OD_{600}=1.0$ for mRNA and protein collection. Total RNA extraction is done using an RNeasy mini kit (QIAGEN, The Netherlands). The purity of RNA is verified on a FA-agarose gel as recommended by QIAGEN and the RNA concentration is determined by measuring the absorbance at 260 nm Two micrograms of RNA is used to synthesize cDNA using a random primer and RevertAid H Minus M-MulV reverse transcriptase (Fermentas, Glen Burnie, Maryland). The strength of the promoter is determined by RT-qPCR carried out in an iCycler IQ® (Bio-Rad, Eke, Belgium) using forward and reverse primers designed to amplify the cDNA corresponding to the transcript produced from the promoter. (For this purpose, the De Mey et al. authors used the Fw-ppc-qPCR and Rv-ppc-qPCR primers, and the primers Fw-rpoB-qPCR and Rv-rpoB-qPCR from the control housekeeping gene rpoB.) SYBR GreenER qPCR supermix (Life Technologies, Grand Island, N.Y.) is used to perform a brief UDG (uracil DNA glycosylase) incubation (50° C. for 2 min) immediately followed by PCR amplification (95° C. for 8.5 min; 40 cycles of 95° C. for 15 s and 60° C. for 1 min) and melting curve analysis (95° C. for 1 min, 55° C. for 1 min and 80 cycles of 55° C.+0.5° C./cycles for 10 s) to identify the presence of primer dimers and analyze the specificity of the reaction. This UDG incubation step before PCR cycling destroys any contaminating dU-containing products from previous reactions. UDG is then inactivated by the high temperatures during normal PCR cycling, thereby allowing the amplification of genuine target sequences. Each sample is performed in triplicate. The relative expression ratios are calculated using the "Delta-delta ct method" of PE Applied Biosystems (PerkinElmer, Forster City, Calif.).

B. Measuring Inducible Promoter Strength and Homogeneity of Induction Using a Fluorescent Reporter Gene These experiments are performed using the methods of Khlebnikov et al. ("Regulatable arabinose-inducible gene expression system with consistent control in all cells of a culture", J Bacteriol 2000 December; 182(24): 7029-7034). Experiments measuring the induction of an inducible promoter are performed in C medium supplemented with 3.4% glycerol as a carbon source (Helmstetter, "DNA synthesis during the division cycle of rapidly growing *Escherichia coli* B/r", J Mol Biol 1968 Feb. 14; 31(3): 507-518). *E. coli* strains containing expression constructs comprising at least one inducible promoter controlling expression of a fluorescent reporter gene are grown at 37° C. under antibiotic selection to an optical density at 600 nm (OD600) of 0.6 to 0.8. Cells are collected by centrifugation (15,000×g), washed in C medium without a carbon source, resuspended in fresh C medium containing antibiotics, glycerol, and/or inducer (for the induction of gene expression) to an OD600 of 0.1 to 0.2, and incubated for 6 h. Samples are taken routinely during the growth period for analysis. Culture fluorescence is measured on a Versafluor Fluorometer (Bio-Rad Inc., Hercules, Calif.) with 360/40-nm-wavelength excitation and 520/10-nm-wavelength emission filters. The strength of expression from an inducible promoter upon induction can be expressed as the ratio of the maximum population-averaged fluorescence (fluorescence/OD ratio) of the induced cells relative to that of control (such as uninduced) cells. To determine the homogeneity of induction within the cell population, flow cytometry is performed on a Beckman-Coulter EPICS XL flow cytometer (Beckman Instruments Inc., Palo Alto, Calif.) equipped with an argon laser (emission at a wavelength of 488 nm and 15 mW) and a 525-nm-wavelength band pass filter. Prior to the analysis, sampled cells are washed with phosphate-buffered saline that had been filtered (filter pore size, 0.22 micrometers), diluted to an OD600 of 0.05, and placed on ice. For each sample, 30,000 events are collected at a rate between 500 and 1,000 events/s. The percentage of induced (fluorescent) cells in each sample can be calculated from the flow cytometry data.

Example 7

Purification of Antibodies

Antibodies produced by the inducible coexpression systems of the invention are purified by centrifuging samples of lysed host cells at 10,000×g for 10 minutes to remove any cells and debris. The supernatant is filtered through a 0.45 micrometer filter. A 1-ml Recombinant Protein G—Sepharose® 4B column (Life Technologies, Grand Island, N.Y.) is set up to achieve flow rates of 1 ml/min, and is used with the following buffers: binding buffer: 0.02 M sodium phosphate, pH 7.0; elution buffer: 0.1 M glycine-HCl, pH 2.7; and neutralization buffer: 1 M Tris-HCl, pH 9.0. The column is equilibrated with 5 column volumes (5 ml) of binding buffer, and then the sample is applied to the column. The column is washed with 5-10 column volumes of the binding buffer to remove impurities and unbound material, continuing until no protein is detected in the eluent (determined by UV absorbance at 280 nm) The column is then eluted with 5 column volumes of elution buffer, and the column is immediately re-equilibrated with 5-10 column volumes of binding buffer.

Example 8

Measurement of Antibody Binding Affinity

The antibody binding affinity, expressed as "Kd" or "Kd value", is measured by a radiolabeled antigen-binding assay (RIA) performed with the Fab version of an antibody of interest and its antigen as described by the following assay. Production of the Fab version of a full-length antibody is well known in the art. Solution-binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, for example, Chen et al., "Selection and analysis of an optimized anti-VEGF antibody: crystal structure of an affinity-matured Fab in complex with antigen", J Mol Biol 1999 Nov. 5; 293(4): 865-881). To establish conditions for the assay, microtiter plates (DYNEX Technologies, Inc., Chantilly, Va.) are coated overnight with 5 micrograms/ml of a capturing anti-Fab antibody (Cappel Labs, West Chester, Pa.) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620; Thermo Scientific, Rochester, N.Y.), 100 pM or 26 pM [$^{125}$I]-antigen are mixed with serial dilutions of a Fab of interest (e.g., consistent with assessment of the anti-VEGF antibody, Fab-12, in Presta et al., "Humanization of an anti-vascular endothelial growth factor monoclonal antibody for the therapy of solid tumors and other disorders", Cancer Res 1997 Oct. 15; 57(20): 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ surfactant in PBS. When the plates have dried, 150 microliters/well of scintillant (MICROSCINT-20™; PerkinElmer, Waltham, Mass.) is added, and the plates are counted on a TOPCOUNT™ gamma counter (PerkinElmer) for ten minutes. Concentrations of each Fab that give less than or equal to 20% of maximal binding are chosen for use in competitive-binding assays.

Alternatively, the Kd or Kd value is measured by using surface-plasmon resonance assays using a BIACORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylamino-propyl)-carbodiimide hydrochloride (EDC) and N-hydroxysuccinimide (NHS) according to the supplier's instructions. Antigen is diluted with 10 mM sodium acetate, pH 4.8, to 5 micrograms/ml (~0.2 micromolar) before injection at a flow rate of 5 microliters/minute to achieve approximately 10 RU of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 microliters/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. If the on-rate exceeds $10^6$ $M^{-1}s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

Another method for determining the equilibrium dissociation constant (Kd) for antibody-antigen binding uses the Octet Red system (ForteBio, Pall Corporation, Port Washington, N.Y.) (fortebio.com). The initial measurement step determines the baseline, followed by loading the His-tagged antigen at a concentration of 25 nM onto Ni-NTA biosensors for 10 minutes in 1×KB+ buffer (0.01% BSA, 0.002% Tween-20 in PBS, pH7.4), followed by another baseline measurement step (1×KB+ buffer only for 2 minutes). The sensor is then dipped into a well containing antibody (the association step) for 10 minutes, followed by a 20-minute wash in 1×KB+ buffer to measure dissociation. The equilibrium dissociation constant (Kd) is calculated as the ratio of $k_{off}/k_{on}$, with the Octet software determining the $k_{off}$ and $k_{on}$ rates.

Example 9

Characterizing the Disulfide Bonds Present in Coexpression Products

The number and location of disulfide bonds in protein coexpression products can be determined by digestion of the protein with a protease, such as trypsin, under non-reducing conditions, and subjecting the resulting peptide fragments to mass spectrometry (MS) combining sequential electron transfer dissociation (ETD) and collision-induced dissociation (CID) MS steps (MS2, MS3) (Nili et al., "Defining the disulfide bonds of insulin-like growth factor-binding protein-5 by tandem mass spectrometry with electron transfer dissociation and collision-induced dissociation", J Biol Chem 2012 Jan. 6; 287(2): 1510-1519; Epub 2011 Nov. 22).

Digestion of Coexpressed Protein.

To prevent disulfide bond rearrangements, any free cysteine residues are first blocked by alkylation: the coexpressed protein is incubated protected from light with the alkylating agent iodoacetamide (5 mM) with shaking for 30 minutes at 20° C. in buffer with 4 M urea. Alternatively and preferably, NEM is used as the alkylating reagent, with trypsin proteolysis in combination with reduction/alkylation conducted under denaturing conditions (6M GuaHCl). Following alkylation, the coexpressed protein is separated by non-reducing SDS-PAGE using precast gels. Alternatively, the coexpressed protein is incubated in the gel after electrophoresis with iodoacetamide or NEM, or without as a control. Protein bands are stained, de-stained with double-deionized water, excised, and incubated twice in 500 microliters of 50 mM ammonium bicarbonate, 50% (v/v) acetonitrile while shaking for 30 minutes at 20° C. Protein samples are dehydrated in 100% acetonitrile for 2 minutes, dried by vacuum centrifugation, and rehydrated with 10 mg/ml of trypsin or chymotrypsin in buffer containing 50 mM ammonium bicarbonate and 5 mM calcium chloride for 15 minutes on ice. Excess buffer is removed and replaced with 50 microliters of the same buffer without enzyme, followed by incubation for 16 hours at 37° C. or 20° C., for trypsin and chymotrypsin, respectively, with shaking. Digestions are stopped by addition of 3 microliters of 88% formic acid, and after brief vortexing, the supernatant is removed and stored at −20° C. until analysis. Alternative protein fragmentation methods (LysC, Glu-C, or CNBr) are used if trypsinolysis provides insufficient sequence coverage (<75%). Using the reducing agent TCEP (tris(2-carboxyethyl)phosphine) under acidic conditions in the presence of NEM provides access to fragments with partly intact disulfide linkages. The disulfide-intact digest map is compared to the reduced (DTT or TCEP) digest map.

Localization of Disulfide Bonds by Mass Spectrometry.

Peptides are injected onto a 1 mm×8 mm trap column (Michrom BioResources, Inc., Auburn, Calif.) at 20 microliters/minute in a mobile phase containing 0.1% formic acid. The trap car-tridge is then placed in-line with a 0.5 mm×250 mm column containing 5 mm Zorbax SB-C18 stationary phase (Agilent Technologies, Santa Clara, Calif.), and peptides separated by a 2-30% acetonitrile gradient over 90 minutes at 10 microliters/minute with a 1100 series capillary HPLC (Agilent Technologies); alternatively, a C18 column suitable for UPLC is used. Peptides are analyzed using a LTQ Velos linear ion trap with an ETD source (Thermo Fisher Scientific Inc., Waltham, Mass.). Electrospray ionization is performed using a Captive Spray source (Michrom Bioresources, Inc.), or preferably, an uncoated, pulled fused silica emitter (New Objective Inc., Woburn, Mass.) at 3.0 kV. Alternatively, analysis of medium-sized proteolytic fragments is performed using a Thermo LTQ-FT MS (7 Tesla) instrument, or a Synapt G2-Si quadrupole traveling wave ion mobility time-of-flight (ToF) mass spectrometer (Waters Corp., Milford, Mass.). Preferably, peptides are analyzed using an Orbitrap Fusion™ Tribrid™ mass spectrometer (Thermo Fisher Scientific). Disulfide-linked peptides have charge states of +4 or greater following trypsinization due to the presence of two N-termini and two basic residues (arginine or lysine) at the carboxy termini. These disulfide-linked peptides are preferentially isolated by the Orbitrap Fusion™ instrument so that the disulfide bonds can be broken using ETD fragmentation. Survey MS scans are followed by seven data-dependant scans consisting of CID and ETD MS2 scans on the most intense ion in the survey scan, followed by five MS3 CID scans on the first- to fifth-most intense ions in the ETD MS2 scan. CID scans use normalized collision energy of 35, and ETD scans use a 100 ins activation time with supplemental activation enabled. Minimum signals to initiate MS2 CID and ETD scans are 10,000, minimum signals for initiation of MS3 CID scans are 1000, and isolation widths for all MS2 and MS3 scans are 3.0 m/z. The dynamic exclusion feature of the software is enabled with a repeat count of 1, exclusion list size of 100, and exclusion duration of 30 seconds. Inclusion lists to target specific cross-linked species for collection of ETD MS2 scans are used. Separate data files for MS2 and MS3 scans are created by Bioworks 3.3 (Thermo Fisher Scientific) using ZSA charge state analysis. Matching of MS2 and MS3 scans to peptide sequences is performed by Sequest (V27, Rev 12, Thermo Fisher Scientific). The analysis is performed without enzyme specificity, a parent ion mass tolerance of 2.5, fragment mass tolerance of 1.0, and a variable mass of +16 for oxidized methionine residues. Results are then analyzed using the program Scaffold (V3_00_08, Proteome Software, Portland, Oreg.) with minimum peptide and protein probabilities of 95 and 99% being used. Software tools for data interpretation also include Proteome Discoverer™ 2.0 with the Disulfinator node (Thermo Fisher Scientific). Peptides from MS3 results are sorted by scan number, and cysteine containing peptides are identified from groups of MS3 scans produced from the five most intense ions observed in ETD MS2 scans. The identities of cysteine peptides participating in disulfide-linked species are further confirmed by manual examination of the parent ion masses observed in the survey scan and the ETD MS2 scan.

Example 10

Isolation of Coexpression Products from Bacterial Cell Periplasm, from Spheroplasts, and from Whole Cells The inducible coexpression system of the invention can be used to express gene products that accumulate in different compartments of the cell, such as the cytoplasm or periplasm. Host cells such as *E. coli* or *S. cerevisiae* have an outer cell membrane or cell wall, and can form spheroplasts when the outer membrane or wall is removed. Coexpressed proteins made in such hosts can be purified specifically from the periplasm, or from spheroplasts, or from whole cells, using the following method (Schoenfeld, "Convenient, rapid enrichment of periplasmic and spheroplasmic protein fractions using the new PeriPreps™ Periplasting Kit", Epicentre Forum 1998 5(1): 5; see epibio.com). This method, using the PeriPreps™ Periplasting Kit (Epicentre® Biotechnologies, Madison Wis.; protocol available at epibio.com), is designed for *E. coli* and other grain negative bacteria, but the general approach can be modified for other host cells such as *S. cerevisiae*.

1. The bacterial host cell culture is grown to late log phase only, as older cell cultures in stationary phase commonly demonstrate some resistance to lysozyme treatment. If the expression of recombinant protein is excessive, cells may prematurely lyse; therefore, cell cultures are not grown in rich medium or at higher growth temperatures that might induce excessive protein synthesis. Protein expression is then induced; the cells should be in log phase or early stationary phase.

2. The cell culture is pelleted by centrifugation at a minimum of 1,000×g for 10 minutes at room temperature. Note: the cells must be fresh, not frozen. The wet weight of the cell pellet is determined in order to calculate the amount of reagents required for this protocol.

3. The cells are thoroughly resuspended in a minimum of 2 ml of PeriPreps Periplasting Buffer (200 mM Tris-HCl pH 7.5, 20% sucrose, 1 mM EDTA, and 30 U/microliter Ready-Lyse Lysozyme) for each gram of cells, either by vortex mixing or by pipeting until the cell suspension is homogeneous. Note: excessive agitation may cause premature lysing of the spheroplasts resulting in contamination of the periplasmic fraction with cytoplasmic proteins.

4. Incubate for five minutes at room temperature. Ready-Lyse Lysozyme is optimally active at room temperature. Lysis at lower temperatures (0° C.-4° C.) requires additional incubation time; at such temperatures incubation times are extended 2- to 4-fold.

5. Add 3 ml of purified water at 4° C. for each gram of original cell pellet weight (Step 2) and mix by inversion.

6. Incubate for 10 minutes on ice.

7. The lysed cells are pelleted by centrifugation at a minimum of 4,000×g for 15 minutes at room temperature.

8. The supernatant containing the periplasmic fraction is transferred to a clean tube.

9. To degrade contaminating nucleic acids, OmniCleave Endonuclease is optionally added to PeriPreps Lysis Buffer. Inclusion of a nuclease will generally improve the yield of protein and the ease of handling of the lysates, but addition of a nuclease is undesirable in some cases: for example, the use of a nuclease should be avoided if residual nuclease activity or transient exposure to the magnesium cofactor will interfere with subsequent assays or uses of the purified protein. The addition of EDTA to the lysate to inactivate OmniCleave Endonuclease, likewise, may interfere with subsequent assay or use of the purified protein. If nuclease is to be added, 2 microliters of OmniCleave Endonuclease and 10 microliters of 1.0 M $MgCl_2$ are diluted up to 1 ml with PeriPreps Lysis Buffer (10 mM Tris-HCl pH 7.5, 50 mM KCl, 1 mM EDTA, and 0.1% deoxycholate) for each milliliter of Lysis Buffer needed in Step 10.

10. The pellet is resuspended in 5 ml of PeriPreps Lysis Buffer for each grain of original cell pellet weight.

11. The pellet is incubated at room temperature for 10 minutes (if included, OmniCleave Endonuclease activity will cause a significant decrease in viscosity; the incubation is continued until the cellular suspension has the consistency of water).

12. The cellular debris is pelleted by centrifugation at a minimum of 4,000×g for 15 minutes at 4° C.

13. The supernatant containing the spheroplast fraction is transferred to a clean tube.

14. If OmniCleave Endonuclease was added to the PeriPreps Lysis Buffer, 20 microliters of 500 mM EDTA is added for each milliliter of the resultant spheroplastic fraction, to chelate the magnesium (the final concentration of EDTA in the lysate is 10 mM). Following hydrolysis of nucleic acids with OmniCleave Endonuclease, lysates may contain substantial amounts of mono- or oligonucleotides. The presence of these degradation products may affect further processing of the lysate: for example, nucleotides may decrease the binding capacity of anion exchange resins by interacting with the resin.

The above protocol can be used to prepare total cellular protein with the following modifications. The cells pelleted in Step 2 can be fresh or frozen; at Step 4, the cells are incubated for 15 minutes; Steps 5 through 8 are omitted; at Step 10, 3 ml of PeriPreps Lysis Buffer is added for each gram of original cell pellet weight.

After preparation of periplasmic, or spheroplastic, or whole-cell protein samples, the samples can be analyzed by any of a number of protein characterization and/or quantification methods. In one example, the successful fractionation of periplasmic and spheroplastic proteins is confirmed by analyzing an aliquot of both the periplasmic and spheroplastic fractions by SDS-PAGE (two microliters of each fraction is generally sufficient for visualization by staining with Coomassie Brilliant Blue). The presence of unique proteins or the enrichment of specific proteins in a given fraction indicates successful fractionation. For example, if the host cell contains a high-copy number plasmid with the ampicillin resistance marker, then the presence of β-lactamase (31.5 kDa) mainly in the periplasmic fraction indicates successful fractionation. Other *E. coli* proteins found in the periplasmic space include alkaline phosphatase (50 kDa) and elongation factor Tu (43 kDa). The amount of protein found in a given fraction can be quantified using any of a number of methods (such as SDS-PAGE and densitometry analysis of stained or labeled protein bands, scintillation counting of radiolabeled proteins, enzyme-linked immunosorbent assay (ELISA), or scintillation proximity assay, among other methods.) Comparing the amounts of a protein found in the periplasmic fraction as compared to the spheroplastic fraction indicates the degree to which the protein has been exported from the cytoplasm into the periplasm.

Example 11

Determination of Polynucleotide or Amino Acid Sequence Similarity

Percent polynucleotide sequence or amino acid sequence identity is defined as the number of aligned symbols, i.e. nucleotides or amino acids, that are identical in both aligned sequences, divided by the total number of symbols in the alignment of the two sequences, including gaps. The degree of similarity (percent identity) between two sequences may be determined by aligning the sequences using the global alignment method of Needleman and Wunsch (J. Mol. Biol. 48:443, 1970), as implemented by the National Center for Biotechnology Information (NCBI) in the Needleman-Wunsch Global Sequence Alignment Tool, available through the website blast.ncbi.nlm.nih.gov/Blast.cgi. In one embodiment, the Needleman and Wunsch alignment parameters are set to the default values (Match/Mismatch Scores of 2 and −3, respectively, and Gap Costs for Existence and Extension of 5 and 2, respectively). Other programs used by those skilled in the art of sequence comparison may also be used to align sequences, such as, for example, the basic local alignment search tool or BLAST® program (Altschul et al., "Basic local alignment search tool", J Mol Biol 1990 Oct. 5; 215(3): 403-410), as implemented by NCBI, using the default parameter settings described at the blast.ncbi.nlm.nih.gov/Blast.cgi website. The BLAST algorithm has multiple optional parameters including two that may be used as follows: (A) inclusion of a filter to mask segments of the query sequence that have low compositional complexity or segments consisting of short-periodicity internal repeats, which is preferably not utilized or set to 'off', and (B) a statistical significance threshold for reporting matches against database sequences, called the 'Expect' or E-score (the expected probability of matches being found merely by chance; if the statistical significance ascribed to a match is greater than this E-score threshold, the match will not be reported). If this 'Expect' or E-score value is adjusted from the default value (10), preferred threshold values are 0.5, or in order of increasing preference, 0.25, 0.1, 0.05, 0.01, 0.001, 0.0001, 0.00001, and 0.000001.

In practicing the present invention, many conventional techniques in molecular biology, microbiology, and recombinant DNA technology are optionally used. Such conventional techniques relate to vectors, host cells, and recombinant methods. These techniques are well known and are explained in, for example, Berger and Kimmel, Guide to Molecular Cloning Techniques, Methods in Enzymology volume 152 Academic Press, Mc, San Diego, Calif.; Sambrook et al., Molecular Cloning—A Laboratory Manual (3rd Ed.), Vol. 1-3, Cold Spring Harbor Laboratory, Cold Spring Harbor, N.Y., 2000; and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, for example for cell isolation and culture and for subsequent nucleic acid or protein isolation, include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York); and Atlas and Parks (Eds.) The Handbook of Microbiological Media (1993) CRC Press, Boca Raton, Fla. Methods of making nucleic acids (for example, by in vitro amplification, purification from cells, or chemical synthesis), methods for manipulating nucleic acids (for example, by site-directed mutagenesis, restriction enzyme digestion, ligation, etc.), and various vectors, cell lines, and the like useful in manipulating and making nucleic acids are described in the above references. In addition, essentially any polynucleotide (including labeled or biotinylated polynucleotides) can be custom or standard ordered from any of a variety of commercial sources.

The present invention has been described in terms of particular embodiments found or proposed to comprise certain modes for the practice of the invention. It will be appreciated by those of ordinary skill in the art that, in light of the present disclosure, numerous modifications and changes can be made in the particular embodiments exemplified without departing from the intended scope of the invention.

All cited references, including patent publications, are incorporated herein by reference in their entirety. Nucleotide and other genetic sequences, referred to by published genomic location or other description, are also expressly incorporated herein by reference.

SEQUENCES PRESENTED IN THE SEQUENCE LISTING

| SEQ ID NO: | Length: | Type: | Organism: | Description; 'Other Information' |
|---|---|---|---|---|
| 1 | 35 | DNA | Artificial Sequence | J23104 promoter |
| 2 | 5883 | DNA | Artificial Sequence | Expression vector pPRO43 |
| 3 | 5882 | DNA | Artificial Sequence | pPRO33 vector |
| 4 | 3698 | DNA | Artificial Sequence | Expression vector pPRO430 |
| 5 | 3610 | DNA | Artificial Sequence | Expression vector pPRO430(CloDF13) |
| 6 | 3255 | DNA | Artificial Sequence | Expression vector pBAD240 |
| 7 | 5802 | DNA | Artificial Sequence | Expression vector pPRO44 |
| 8 | 5791 | DNA | Artificial Sequence | Expression vector pPRO45 |
| 9 | 25 | DNA | Artificial Sequence | pPRO_REV_SpeI primer |
| 10 | 28 | DNA | Artificial Sequence | pPRO_FOR_AatII primer |
| 11 | 46 | DNA | Artificial Sequence | RSF1030_FOR_SpeI primer |
| 12 | 52 | DNA | Artificial Sequence | RSF1030_REV_AatII primer |
| 13 | 46 | DNA | Artificial Sequence | CloDF13_FOR_SpeI primer |
| 14 | 56 | DNA | Artificial Sequence | CloDF13_REV_AatII primer |
| 15 | 5304 | DNA | Artificial Sequence | Dual-promoter vector, pSOL |
| 16 | 451 | PRT | Artificial Sequence | Infliximab chimeric (murine variable doman, human constant domain) heavy chain |
| 17 | 215 | PRT | Artificial Sequence | Infliximab chimeric (murine variable doman, human constant domain) light chain |
| 18 | 4594 | DNA | Artificial Sequence | pBAD240-Infliximab_HC expression construct |
| 19 | 4332 | DNA | Artificial Sequence | pPRO430-Infliximab_LC expression construct |
| 20 | 7288 | DNA | Artificial Sequence | pSOL-Infliximab expression construct |

What is claimed is:

1. An expression construct comprising a nucleotide sequence selected from the group consisting of:
   (a) a nucleotide sequence comprising a propionate-inducible promoter and having at least 97% sequence identity to at least 225 contiguous bases of nucleotides 4937 through 5185 of SEQ ID NO:15;
   (b) a nucleotide sequence comprising a propionate-inducible promoter and having at least 80% sequence identity to at least 300 contiguous bases of nucleotides 4937 through 5304 of SEQ ID NO:15;
   (c) a nucleotide sequence comprising an arabinose-inducible promoter and having at least 87% sequence identity to at least 350 contiguous bases of nucleotides 2818 through 3259 of SEQ ID NO:15; and
   (d) a nucleotide sequence comprising a propionate-inducible promoter and having at least 90% sequence identity to at least 450 contiguous bases of nucleotides 10 through 1822 of SEQ ID NO:2.

2. The expression construct of claim 1 comprising SEQ ID NO:15.

3. A host cell comprising the expression construct of claim 1.

4. The host cell of claim 3 wherein the host cell is a prokaryotic cell.

5. The host cell of claim 4 wherein the host cell is *E. coli*.

6. The host cell of claim 5 wherein the host cell has a reduced level of gene function of at least one gene encoding a protein that metabolizes an inducer of at least one inducible promoter.

7. The host cell of claim 6 wherein the gene encoding a protein that metabolizes an inducer of at least one said inducible promoter is selected from the group consisting of araA, araB, prpB, prpD, rhaA, rhaB, rhaD, xylA, and xylB.

8. The host cell of claim 6, wherein the host cell has a reduced level of function of at least one gene selected from the group consisting of araA and araB, and wherein the expression construct comprises at least one arabinose-inducible promoter and further comprises a polynucleotide sequence encoding AraC.

9. The host cell of claim 6, wherein the host cell has a reduced level of function of at least one gene selected from the group consisting of prpB and prpD, and further comprises a polynucleotide sequence encoding PrpR.

10. The host cell of claim 5 wherein the host cell has an alteration of gene function of at least one gene encoding a transporter protein for an inducer of at least one said inducible promoter.

11. The host cell of claim 10 wherein the gene encoding a transporter protein is selected from the group consisting of araE, araF, araG, araH, rhaT, xylF, xylG, and xylH.

12. The host cell of claim 11 wherein the gene encoding a transporter protein is araE, and the alteration of gene function of said araE gene is changing the promoter controlling expression of the host cell's chromosomal araE gene from an arabinose-inducible promoter to a constitutive promoter.

13. The host cell of claim 5 wherein the host cell has a reduced level of gene function of a gene that encodes a reductase.

14. The host cell of claim 13 wherein the gene that encodes a reductase is trxB.

15. The host cell of claim 5 wherein the host cell has an altered gene function of a gene selected from the group consisting of gor and gshB.

16. The host cell of claim 5 wherein the host cell expresses a mutant form of AhpC.

17. The host cell of claim 5 wherein the host cell further comprises one or more of the following: (a) a deletion of the araBAD genes; (b) an altered gene function of the araE and araFGH genes; (c) a lacY(A177C) gene; (d) a reduced gene function of the prpB and prpD genes; (e) a reduced gene function of the sbm/scpA-ygfD/argK-ygfGH/scpBC genes; (f) a reduced gene function of the gor and trxB genes; (g) a reduced gene function of the AscG gene; (h) a polynucleotide encoding a form of DsbC lacking a signal peptide; (i) a polynucleotide encoding Erv1p; and (j) a polynucleotide encoding a chaperone.

18. A host cell comprising the expression construct of claim 1, wherein the expression construct further comprises at least one polynucleotide sequence encoding at least one gene product to be transcribed from an inducible promoter.

19. A kit comprising the host cell of claim 1.

* * * * *

SEQUENCE LISTING

<160> NUMBER OF SEQ ID NOS: 20

<210> SEQ ID NO 1
<211> LENGTH: 35
<212> TYPE: DNA
<213> ORGANISM: Artificial Sequence
<220> FEATURE:
<223> OTHER INFORMATION: J23104 promoter

<400> SEQUENCE: 1
ttgacagcta gctcagtcct aggtattgtg ctagc                                35

<210> SEQ ID NO 2
<211> LENGTH: 5883
<212> TYPE: DNA
<213> ORGANISM: Artificial Sequence
<220> FEATURE:
<223> OTHER INFORMATION: Expression vector pPRO43

<400> SEQUENCE: 2
atcgatttag cttttcagac gacgccaaaa ggtcgtacgt gaaatacccca aatagttggc      60 cgcagccgtc ttgtcaccat taaacttctc aagcgcttgc tgcggggtca gcaaacgcgg     120
agccggcgtc tttgcgctct cacgcgccag ctccggcagc agcaactgca tgaattgcgg     180
agtcagatcc ggggtcggct caacggacag gaacagcgcc aggcgttcca tcatattacg     240
cagctcgcgg atgttacccg gccagtcata atgcagcagc accgtttcgc tcgcctgcag     300 accctggcg agtgccgcag agaacggtgc gctcagggct gccagcgaga ctttcaggaa      360
agactccgcc agcggtaaaa tgtcggcgac acgttcacgc aacggcggga gctgcagacg     420
cagaatgctc aggcggtaga acaggtcgcg acgaaaacgg ccctgttgca tatcctcttc     480
cagattgcag tgggtcgcgc taatcacgcg cacgtctacc ggaaccggtt gatgaccacc     540
gacgcgggtc acttctttct cttccagcac acgcagcaga cgggtttgca atggcagcgg     600
catctcaccg atctcgtcca ggaacaaggt gccgccgtgg gcaatttcaa acaaaccagc     660
acggccaccg cgacggctac ccgtgaatgc gccctcttcg tagccaaaca gctcagcttc     720
cagcaggctt ccgcgattg caccgcaatt aactgccaca aacggatgag atttcttacc      780
ctggcgggca tcgtgacggg cgaaatactc acgatggatt gcttgcgcag ccagttcctt     840
acccgtacca gtctcgcctt cgatcagaac agccgcgctg ctacgtgcat acagcagaat     900
ggtctggcga acttgctcca tttgagggct ttggcccagc atatcacccca ggacataacg     960 ggtacgcagc gcattacgcg tcgcatcgtg ggtgttgtgg cgcaggctca ttctggtcat    1020
gtccagggcg tcgctgaacg cctgacgcac cgttgccgcg ctgtagataa agatgcccgt    1080
catgcccgct tcttcggcca agtccgtgat cagacccgca ccaaccacag cctcggtacc    1140
gttcgctttc agttcgttga tctgccacg tgcatcttcc tcgtaatgt agctgcgttg      1200 gtccaggcgc agattaaagg tcttttgaaa cgcgaccagc gcaggatcg tttcctggta      1260 ggtgacaacg ccaatcgagg aggtcagttt gcctgccttc gccagcgcct gcaagacatc    1320
gtaaccgctc ggcttaatca ggatcaccgg cacggacaga cgggatttca ggtaggcacc    1380
attgctaccc gctgcgataa tggcgtcaca acgctcgttg ccagcttttt gcgaatgta     1440 ggtaacggct ttctcgaaac ccagctgaat cggagtgatg ttcgccaggt gatcaaactc    1500
caggctaatg tcgcggaaca actcgaacag acgggtgacg ctaacggtcc aaataactgg    1560
tttatcatcg ttcaaacgcg gtgggtgtgc catggtgaat acctcctgtt aagaaaccga    1620
atattgggtt taaacttgtt tcataattgt tgcaatgaaa cgcggtgaaa cattgcctga    1680

-continued

```
aacgttaact gaaacgcata tttgcggatt agttcatgac tttatctcta acaaattgaa   1740
attaaacatt taattttatt aaggcaattg tggcacaccc cttgctttgt ctttatcaac   1800
gcaaataaca agttgataac aagctagcga attcgagctc ggtacccggg gatcctctag   1860
agtcgacctg caggcatgca agcttggctg ttttggcgga tgagagaaga ttttcagcct   1920
gatacagatt aaatcagaac gcagaagcgg tctgataaaa cagaatttgc ctggcggcag   1980
tagcgcggtg gtcccacctg accccatgcc gaactcagaa gtgaaacgcc gtagcgccga   2040
tggtagtgtg gggtctcccc atgcgagagt agggaactgc caggcatcaa ataaaacgaa   2100
aggctcagtc gaaagactgg gcctttcgtt ttatctgttg tttgtcggtg aacgctctcc   2160
tgagtaggac aaatccgccg ggagcggatt tgaacgttgc gaagcaacgg cccggagggt   2220
ggcgggcagg acgccgcca taaactgcca ggcatcaaat taagcagaag gccatcctga   2280
cggatggcct ttttgcgttt ctacaaactc ttttgtttat ttttctaaat acattcaaat   2340
atgtatccgc tcatgagaca ataaccctga taaatgcttc aataatattg aaaaaggaag   2400
agtatgagta ttcaacattt ccgtgtcgcc cttattccct ttttgcggc attttgcctt   2460 cctgtttttg ctcacccaga aacgctggtg aaagtaaaag atgctgaaga tcagttgggt   2520
gcagcaaact attaactggc gaactactta ctctagcttc ccggcaacaa ttaatagact   2580
ggatggaggc ggataaagtt gcaggaccac ttctgcgctc ggcccttccg gctggctggt   2640
ttattgctga taaatctgga gccggtgagc gtgggtctcg cggtatcatt gcagcactgg   2700
ggccagatgg taagccctcc cgtatcgtag ttatctacac gacggggagt caggcaacta   2760
tggatgaacg aaatagacag atcgctgaga taggtgcctc actgattaag cattggtaac   2820
tgtcagacca agtttactca tatatacttt agattgattt acgcgcctg tagcggcgca   2880 ttaagcgcgg cgggtgtggt ggttacgcgc agcgtgaccg ctacacttgc cagcgcccta   2940
gcgcccgctc ctttcgcttt cttcccttcc tttctcgcca cgttcgccgg ctttccccgt   3000
caagctctaa atcgggggct ccctttaggg ttccgattta gtgctttacg gcacctcgac   3060
cccaaaaaac ttgatttggg tgatggttca cgtagtgggc catcgccctg atagacggtt   3120
tttcgccctt tgacgttgga gtccacgttc tttaatagtg gactcttgtt ccaaactgga   3180
acaacactca accctatctc gggctattct tttgatttat aagggatttt gccgatttcg   3240
gcctattggt taaaaatga gctgatttaa caaaaattta cgcgaattt taacaaaata   3300 ttaacgttta caatttaaaa ggatctaggt gaagatcctt tttgataatc tcatgaccaa   3360
aatcccttaa cgtgagtttt cgttccactg agcgtcagac cccgtagaaa agatcaaagg   3420
atcttcttga tccttttt ttctgcgcgt aatctgctgc ttgcaaacaa aaaaaccacc   3480
gctaccagcg gtggtttgtt tgccggatca agagctacca actctttttc cgaaggtaac   3540
tggcttcagc agagcgcaga taccaaatac tgtccttcta gtgtagccgt agttaggcca   3600
ccacttcaag aactctgtag caccgcctac atacctcgct ctgctaatcc tgttaccagt   3660
caggcatttg agaagcacac ggtcacactg cttccggtag tcaataaacc ggtaaaccag   3720
caatagacat aagcggctat ttaacgaccc tgccctgaac cgacgaccgg gtcgaatttg   3780
ctttcgaatt tctgccattc atccgcttat tatcacttat tcaggcgtag caaccaggcg   3840
tttaagggca ccaataactg ccttaaaaaa attacgcccc gccctgccac tcatcgcagt   3900
actgttgtaa ttcattaagc attctgccga catggaagcc atcacaaacg gcatgatgaa   3960
cctgaatcgc cagcggcatc agcaccttgt cgccttgcgt ataatatttg cccatggtga   4020
```

```
aaacgggggc gaagaagttg tccatattgg ccacgtttaa atcaaaactg gtgaaactca    4080
cccagggatt ggctgagacg aaaaacatat tctcaataaa cccctttaggg aaataggcca   4140
ggttttcacc gtaacacgcc acatcttgcg aatatatgtg tagaaactgc cggaaatcgt    4200
cgtggtattc actccagagc gatgaaaacg tttcagtttg ctcatggaaa acggtgtaac    4260
aagggtgaac actatcccat atcaccagct caccgtcttt cattgccata cggaattccg    4320
gatgagcatt catcaggcgg gcaagaatgt gaataaaggc cggataaaac ttgtgcttat    4380
ttttctttac ggtcttttaaa aaggccgtaa tatccagctg aacggtctgg ttataggtac   4440
attgagcaac tgactgaaat gcctcaaaat gttctttacg atgccattgg gatatatcaa    4500
cggtggtata tccagtgatt ttttttctcca ttttagcttc cttagctcct gaaaatctcg   4560
ataactcaaa aaatacgccc ggtagtgatc ttatttcatt atggtgaaag ttggaacctc    4620
ttacgtgccg atcaacgtct cattttcgcc aaaagttggc ccagggcttc ccggtatcaa    4680
cagggacacc aggatttatt tattctgcga agtgatcttc cgtcacaggt atttattcgg    4740
cgcaaagtgc gtcgggtgat gctgccaact tactgattta gtgtatgatg gtgttttttga  4800
ggtgctccag tggcttctgt ttctatcagc tgtccctcct gttcagctac tgacggggtg   4860
gtgcgtaacg gcaaaagcac cgccggacat cagcgctagt agcggagtgt atactggctt   4920
actatgttgg cactgatgag ggtgtcagtg aagtgcttca tgtggcagga gaaaaaaggc   4980
tgcaccggtg cgtcagcaga atatgtgata caggatatat tccgcttcct cgctcactga   5040
ctcgctacgc tcggtcgttc gactgcggcg agcggaaatg gcttacgaac ggggcggaga   5100
tttcctggaa gatgccagga agatacttaa cagggaagtg agagggccgc ggcaaagccg   5160
ttttttccata ggctccgccc ccctgacaag catcacgaaa tctgacgctc aaatcagtgg   5220
tggcgaaacc cgacaggact ataaagatac caggcgtttc ccctggcgg ctccctcgtg    5280
cgctctcctg ttcctgcctt tcggtttacc ggtgtcattc cgctgttatg gccgcgtttg    5340
tctcattcca cgcctgacac tcagttccgg gtaggcagtt cgctccaagc tggactgtat    5400
gcacgaaccc cccgttcagt ccgaccgctg cgccttatcc ggtaactatc gtcttgagtc    5460
caacccggaa agacatgcaa aagcaccact ggcagcagcc actggtaatt gatttagagg    5520
agttagtctt gaagtcatgc gccggttaag gctaaactga aaggacaagt tttggtgact    5580
gcgctcctcc aagccagtta cctcggttca aagagttggt agctcagaga accttcgaaa    5640
aaccgccctg caaggcggtt ttttcgtttt cagagcaaga gattacgcgc agaccaaaac    5700
gatctcaaga agatcatctt attaatcaga taaaatattt gctcatgagc ccgaagtggc    5760
gagcccgatc ttccccatcg gtgatgtcgg cgatataggc gccagcaacc gcacctgtgg    5820
cgccggtgat gccggccacg atgcgtccgg cgtagaggat ctgctcatgt ttgacagctt    5880
atc                                                                 5883

<210> SEQ ID NO 3
<211> LENGTH: 5882
<212> TYPE: DNA
<213> ORGANISM: Artificial Sequence
<220> FEATURE:
<223> OTHER INFORMATION: pPRO33 vector

<400> SEQUENCE: 3
atcgattcag cttttcagcc gccgccagaa cgtcgtccgg ctgatgccta aataattcgc      60
cgctgctgtt ttatcgccat taaatttctc cagtgcctgt tgtggtgtca gtaagcgtgg     120
agcgggagtt ttcgccgact cgcgcgccag ttccggcagt agcagttgca taaactgcgg    180
```

```
cgttaaatcc ggcgtcggtt ccacacttaa aaacagcgcc agtcgttcca tcatattgcg      240
cagttcacga atattgcctg gccagtcgta gtgcagcagc acagtttcac ttgcctgtaa      300
cccctggcgt aatgcagcag aaaatggggc ggagagcgcc gccagagaca ctttcaaaaa      360
gctttccgcc agcggaagaa tatccgccac ccgctcgcgc agtggtggca attgcagacg      420
caaaatactc agccgataaa acagatcacg gcgaaaacgt ccttgctgca tatcttcttc      480
cagattgcag tgagtggcgc taatgacccg tacatctacc ggaacaggct gatgcccgcc      540
gacgcgggtg acctcttttt cttccagcac ccgcagcagc cgggtctgca aggtagcgg       600 catttcgcca atctcatcca gaaacagcgt accgccgtgg gcaatttcga acagcccggc      660
gcgacctccg cgtcgcgagc cggtaaacgc cccttcctca tagccaaaca gttctgcttc      720
cagcagcgat tcggcaatcg ccccgcagtt gacggcaaca aacggatgcg acttttttgcc     780 ctgtcgcgca tcgtggcggg caaaatattc ccgatgaatc gcctgggccg ccagctcttt      840
gcccgtcccc gtttccccct caatcaacac cgccgcactg gagcgggcat acagcaaaat      900
agtctgccgt acttgttcca tctgtggtga ttgaccgagc atatcgccca gcacgtaacg      960
agtacgcagg gcgttgcggg tggcatcgtg agtgttatgg cgtaacgaca tgcgcgtcat     1020
atccagcgca tcgctgaacg cctggcgcac ggtggcggcg aatagataaa aaattccggt    1080
cattccggct tcttctgcca aatcggtaat cagccctgcg ccgaccaccg cttcggtgcc    1140
gttagctttt agctcgttaa tctgcccgcg tgcgtcttcc tcggtaatgt agctacgttg    1200
gtcgaggcgc aaattaaagg ttttttgaaa cgccaccagc gctggaatgg tttcctgata    1260
ggtgacaacg ccgatagaag aggtgagttt tccggctttt gccagtgcct gtaacacatc    1320
gtagccgctc ggtttaatca aaataactgg cactgacagg cggcttttca ggtacgcgcc    1380
gttagagcca gccgcgatga tggcgtcaca gcgttcgttt gccagtttct tgcggatgta    1440
ggtcactgct ttttcaaagc caagctgaat aggggtaatg ttcgccaggt gatcaaactc    1500
gaggctgata tcgcgaaaca gctcgaacag gcgcgttaca gataccgtcc agataaccgg    1560
tttgtcgtca ttaagccgtg gtggatgtgc catagcgcac cgcaaagtta agaaaccgaa    1620
tattgggttt agtcttgttt cataattgtt gcaatgaaac gcggtgaaac attgcctgaa    1680
acgttaactg aaacgcatat ttgcggatta gttcatgact ttatctctaa caaattgaaa    1740
ttaaacattt aattttatta aggcaattgt ggcacacccc ttgctttgtc tttatcaacg    1800
caaataacaa gttgataaca agctagcgaa ttcgagctcg gtacccgggg atcctctaga    1860
gtcgacctgc aggcatgcaa gcttggctgt tttggcggat gagagaagat tttcagcctg    1920
atacagatta aatcagaacg cagaagcggt ctgataaaac agaatttgcc tggcggcagt    1980
agcgcggtgg tcccacctga ccccatgccg aactcagaag tgaaacgccg tagcgccgat    2040
ggtagtgtgg ggtctcccca tgcgagagta gggaactgcc aggcatcaaa taaaacgaaa    2100
ggctcagtcg aaagactggg cctttcgttt tatctgttgt ttgtcggtga acgctctcct    2160
gagtaggaca atccgccgg gagcggattt gaacgttgcg aagcaacggc ccggagggtg    2220
gcgggcagga cgcccgccat aaactgccag gcatcaaatt aagcagaagg ccatcctgac    2280
ggatggcctt tttgcgtttc tacaaactct tttgtttatt tttctaaata cattcaaata    2340
tgtatccgct catgagacaa taaccctgat aaatgcttca ataatattga aaaggaaga    2400 gtatgagtat tcaacatttc cgtgtcgccc ttattccctt ttttgcggca ttttgccttc    2460 ctgttttgc tcacccagaa acgctggtga agtaaaaga tgctgaagat cagttgggtg     2520
```

```
cagcaaacta ttaactggcg aactacttac tctagcttcc cggcaacaat taatagactg      2580
gatggaggcg gataaagttg caggaccact tctgcgctcg gcccttccgg ctggctggtt      2640
tattgctgat aaatctggag ccggtgagcg tgggtctcgc ggtatcattg cagcactggg      2700
gccagatggt aagccctccc gtatcgtagt tatctcacac gacggggagtc aggcaactat      2760 ggatgaacga aatagacaga tcgctgagat aggtgcctca ctgattaagc attggtaact      2820
gtcagaccaa gtttactcat atatacttta gattgattta cgcgccctgt agcggcgcat      2880
taagcgcggc gggtgtggtg gttacgcgca gcgtgaccgc tacacttgcc agcgccctag      2940
cgcccgctcc tttcgctttc ttcccttcct ttctcgccac gttcgccggc tttccccgtc      3000
aagctctaaa tcggggggctc cctttagggt tccgatttag tgctttacgg cacctcgacc      3060
ccaaaaaact tgatttgggt gatggttcac gtagtgggcc atcgccctga tagacgtttt     3120
ttcgcccttt gacgttggag tccacgttct ttaatagtgg actcttgttc caaactggaa      3180
caacactcaa ccctatctcg ggctattctt tgatttata agggattttg ccgatttcgg      3240
cctattggtt aaaaaatgag ctgatttaac aaaaatttaa cgcgaatttt aacaaaatat      3300
taacgtttac aatttaaaag gatctaggtg aagatccttt ttgataatct catgaccaaa      3360
atcccttaac gtgagttttc gttccactga gcgtcagacc ccgtagaaaa gatcaaagga      3420
tcttcttgag atccttttt tctgcgcgta atctgctgct tgcaaacaaa aaaaccaccg      3480
ctaccagcgg tggtttgttt gccggatcaa gagctaccaa ctctttttcc gaaggtaact      3540
ggcttcagca gagcgcagat accaaatact gtccttctag tgtagccgta gttaggccac      3600
cacttcaaga actctgtagc accgcctaca tacctcgctc tgctaatcct gttaccagtc      3660
aggcatttga aagcacacg gtcacactgc ttccggtagt caataaaccg gtaaaccagc      3720
aatagacata gcggctatt taacgaccct gccctgaacc gacgacccgg tcgaatttgc      3780
tttcgaattt ctgccattca tccgcttatt atcacttatt caggcgtagc aaccaggcgt      3840
ttaagggcac caataactgc cttaaaaaaa ttacgccccg ccctgccact catcgcagta      3900
ctgttgtaat tcattaagca ttctgccgac atggaagcca tcacaaacgg catgatgaac      3960
ctgaatcgcc agcggcatca gcaccttgtc gccttgcgta taatatttgc ccatggtgaa      4020
aacgggggcg aagaagttgt ccatattggc cacgtttaaa tcaaaactgg tgaaactcac      4080
ccagggattg gctgagacga aaacatatt ctcaataaac cctttaggga ataggccag      4140 gttttcaccg taacacgcca catcttgcga atatatgtgt agaaactgcc ggaaatcgtc      4200
gtggtattca ctccagagcg atgaaaacgt ttcagtttgc tcatggaaaa cggtgtaaca      4260
agggtgaaca ctatcccata tcaccagctc accgtctttc attgccatac ggaattccgg      4320
atgagcattc atcaggcggg caagaatgtg aataaaggcc ggataaaact tgtgcttatt      4380
tttctttacg gtctttaaaa aggccgtaat atccagctga acggtctggt tataggtaca      4440
ttgagcaact gactgaaatg cctcaaaatg ttctttacga tgccattggg atatatcaac      4500
ggtggtatat ccagtgattt ttttctccat tttagcttcc ttagctcctg aaaatctcga      4560
taactcaaaa aatacgcccg gtagtgatct tatttcatta tggtgaaagt tggaacctct      4620
tacgtgccga tcaacgtctc attttcgcca aaagttggcc cagggcttcc cggtatcaac      4680
agggacacca ggatttattt attctgcgaa gtgatcttcc gtcacaggta tttattcggc      4740
gcaaagtgcg tcgggtgatg ctgccaactt actgatttag tgtatgatgg tgtttttgag      4800
gtgctccagt ggcttctgtt tctatcagct gtccctcctg ttcagctact gacggggtgg      4860
tgcgtaacgg caaaagcacc gccggacatc agcgctagta gcggagtgta tactggctta      4920
```

```
ctatgttggc actgatgagg gtgtcagtga agtgcttcat gtggcaggag aaaaaaggct    4980
gcaccggtgc gtcagcagaa tatgtgatac aggatatatt ccgcttcctc gctcactgac    5040
tcgctacgct cggtcgttcg actgcggcga gcggaaatgg cttacgaacg gggcggagat    5100
ttcctggaag atgccaggaa gatacttaac agggaagtga gagggccgcg gcaaagccgt    5160
ttttccatag gctccgcccc cctgacaagc atcacgaaat ctgacgctca atcagtggt     5220 ggcgaaaccc gacaggacta aagataccag gcgtttccc cctggcggc tccctcgtgc     5280 gctctcctgt tcctgccttt cggtttaccg gtgtcattcc gctgttatgg ccgcgtttgt    5340
ctcattccac gcctgacact cagttccggg taggcagttc gctccaagct ggactgtatg    5400
cacgaacccc ccgttcagtc cgaccgctgc gccttatccg gtaactatcg tcttgagtcc    5460
aacccggaaa gacatgcaaa agcaccactg gcagcagcca ctggtaattg atttagagga    5520
gttagtcttg aagtcatgcg ccggttaagg ctaaactgaa aggacaagtt ttggtgactg    5580
cgctcctcca agccagttac ctcggttcaa agagttggta gctcagagaa ccttcgaaaa    5640
accgccctgc aaggcggttt tttcgttttc agagcaagag attacgcgca gaccaaaacg    5700
atctcaagaa gatcatctta ttaatcagat aaaatatttg ctcatgagcc cgaagtggcg    5760
agcccgatct tccccatcgg tgatgtcggc gatataggcg ccagcaaccg cacctgtggc    5820
gccggtgatg ccggccacga tgcgtccggc gtagaggatc tgctcatgtt tgacagctta    5880
tc                                                                   5882

<210> SEQ ID NO 4
<211> LENGTH: 3698
<212> TYPE: DNA
<213> ORGANISM: Artificial Sequence
<220> FEATURE:
<223> OTHER INFORMATION: Expression vector pPRO430

<400> SEQUENCE: 4
ccccagaggc aggtctagcg gagtgtatac tggcttacta tgttggcact gatgagggtg      60
tcagtgaagt gcttcatgtg gcaggagaaa aaaggctgca ccggtgcgtc agcagaatat     120
gtgatacagg atatattccg cttcctcgct cactgactcg ctacgctcgg tcgttcgact     180
gcggcgagcg gaaatggctt acgaacgggg cggagatttc ctggaagatg ccaggaagat     240
acttaacagg gaagtgagag gccgcggca agccgttttt ccataggct ccgcccccct      300 gacaagcatc acgaaatctg acgctcaaat cagtggtggc gaaacccgac aggactataa     360
agataccagg cgtttccccc tggcggctcc ctcgtgcgct ctcctgttcc tgcctttcgg     420
tttaccggtg tcattccgct gttatggccg cgtttgtctc attccacgcc tgacactcag     480
ttccgggtag gcagttcgct ccaagctgga ctgtatgcac gaaccccccg ttcagtccga     540
ccgctgcgcc ttatccggta actatcgtct tgagtccaac ccggaaagac atgcaaaagc     600
accactggca gcagcactg gtaattgatt tagaggagt agtcttgaag tcatgcgccg      660
gttaaggcta aactgaaagg acaagttttg tgactgcgc tcctccaagc cagttacctc     720
ggttcaaaga gttggtagct cagagaacct tcgaaaaacc gccctgcaag gcggtttttt     780
cgttttcaga gcaagagatt acgcgcagac caaaacgatc tcaagaagat catcttatta     840
aacctgcctc taaaaacttt tattacgccc cgccctgcca ctcatcgcag tactgttgta     900
attcattaag cattctgccg acatggaagc catcacagac ggcatgatga acctgaatcg     960
ccagcggcat cagcaccttg tcgccttgcg tataatattt gcccatagtg aaaacgggg     1020
```

```
cgaagaagtt gtccatattg gccacgttta aatcaaaact ggtgaaactc acccagggat    1080
tggctgagac gaaaaacata ttctcaataa accctttagg gaaataggcc aggttttcac    1140
cgtaacacgc cacatcttgc gaatatatgt gtagaaactg ccggaaatcg tcgtggtatt    1200
cactccagag cgatgaaaac gtttcagttt gctcatggaa aacggtgtaa caagggtgaa    1260
cactatccca tatcaccagc tcaccgtctt tcattgccat acggaactcc ggatgagcat    1320
tcatcaggcg ggcaagaatg tgaataaagg ccggataaaa cttgtgctta ttttcttta    1380 cggtctttaa aaaggccgta atatccagct gaacggtctg gttataggta cattgagcaa    1440
ctgactgaaa tgcctcaaaa tgttctttac gatgccattg ggatatatca acggtggtat    1500
atccagtgat tttttctcc atcatattct tcctttttca atattattga agcatttatc    1560
agggttattg tctcatgagc ggatacatat ttgaatgtat ttagaaaaat aaacaaatag    1620
gggtcagtgt tacaaccaat taaccaattc tgatctcctg ttagtgaggg ttaatgcccg    1680
gaacgaagaa aggcccaccc gtgaaggtga gccagtgagt tggttacatt ttctcttgag    1740
ggtttagctt ttcagacgac gccaaaaggt cgtacgtgaa atacccaaat agttggccgc    1800
agccgtcttg tcaccattaa acttctcaag cgcttgctgc ggggtcagca aacgcggagc    1860
cggcgtcttt gcgctctcac gcgccagctc cggcagcagc aactgcatga attgcggagt    1920
cagatccggg gtcggctcaa cggacaggaa cagcgccagg cgttccatca tattacgcag    1980
ctcgcggatg ttacccggcc agtcataatg cagcagcacc gtttcgctcg cctgcagacc    2040
ctggcgcagt gccgcagaga acggtgcgct cagggctgcc agcgagactt tcaggaaaga    2100
ctccgccagc ggtaaaatgt cggcgacacg ttcacgcaac ggcgggagct gcagacgcag    2160
aatgctcagg cggtagaaca ggtcgcgacg aaaacggccc tgttgcatat cctcttccag    2220
attgcagtgg gtcgcgctaa tcacgcgcac gtctaccgga accggttgat gaccaccgac    2280
gcgggtcact tctttctctt ccagcacacg cagcagacgg gtttgcaatg gcagcggcat    2340
ctcaccgatc tcgtccagga acaaggtgcc gccgtgggca atttcaaaca aaccagcacg    2400
gccaccgcga cggctacccg tgaatgcgcc ctcttcgtag ccaaacagct cagcttccag    2460 caggcttttcc gcgattgcac cgcaattaac tgccacaaac ggatgagatt tcttaccctg    2520
gcgggcatcg tgacgggcga atactcacg atggattgct tgcgcagcca gttccttacc    2580
cgtaccagtc tcgccttcga tcagaacagc cgcgctgcta cgtgcataca gcagaatggt    2640
ctggcgaact tgctccattt gagggctttg gcccagcata tcacccagga cataacgggt    2700
acgcagcgca ttacgcgtcg catcgtgggt gttgtggcgc aggctcattc tggtcatgtc    2760
cagggcgtcg ctgaacgcct gacgcaccgt tgccgcgctg tagataaaga tgcccgtcat    2820
gcccgcttct tcggccaagt ccgtgatcag acccgcacca accacagcct cggtaccgtt    2880
cgctttcagt tcgttgatct ggccacgtgc atcttcctcg gtaatgtagc tgcgttggtc    2940
caggcgcaga ttaaaggtct tttgaaacgc gaccagcgca gggatcgttt cctggtaggt    3000
gacaacgcca atcgaggagg tcagtttgcc tgccttcgcc agcgcctgca agacatcgta    3060
accgctcggc ttaatcagga tcaccggcac ggacagacgg gatttcaggt aggcaccatt    3120 gctaccgct gcgataatgg cgtcacaacg ctcgttggcc agcttttgc gaatgtaggt    3180 aacggctttc tcgaaaccca gctgaatcgg agtgatgttc gccaggtgat caaactccag    3240
gctaatgtcg cggaacaact cgaacagacg ggtgacgcta acggtccaaa taactggttt    3300
atcatcgttc aaacgcggtg ggtgtgccat ggtgaatacc tcctgttaag aaaccgaata    3360
ttgggtttaa acttgtttca taattgttgc aatgaaacgc ggtgaaacat tgcctgaaac    3420
```

```
gttaactgaa acgcatattt gcggattagt tcatgacttt atctctaaca aattgaaatt    3480
aaacatttaa ttttattaag gcaattgtgg cacacccctt gctttgtctt tatcaacgca    3540
aataacaagt tgataacaaa agcttaggag gaaaacatag agaccggtct ctctcgagta    3600
actagttgat agagatcaag ccttaacgaa ctaagacccc cgcaccgaaa ggtccggggg    3660 tttttttttga ccttaaaaac ataaccgagg agcagaca                          3698
```

<210> SEQ ID NO 5
<211> LENGTH: 3610
<212> TYPE: DNA
<213> ORGANISM: Artificial Sequence
<220> FEATURE:
<223> OTHER INFORMATION: Expression vector pPRO430(CloDF13)

<400> SEQUENCE: 5

```
ccccagaggc aggtgcgctg cggacacata caaagttacc cacagattcc gtggataagc      60
aggggactaa catgtgaggc aaaacagcag ggccgcgccg gtggcgtttt tccataggct     120 ccgcccctcct gccagagttc acataaacag acgcttttcc ggtgcatctg tgggagccgt    180
gaggctcaac catgaatctg acagtacggg cgaaacccga caggacttaa agatccccac    240
cgtttccggc gggtcgctcc ctcttgcgct ctcctgttcc gaccctgccg tttaccggat    300
acctgttccg cctttctccc ttacgggaag tgtggcgctt tctcatagct cacacactgg    360
tatctcggct cggtgtaggt cgttcgctcc aagctgggct gtaagcaaga actccccgtt    420
cagcccgact gctgcgcctt atccggtaac tgttcacttg agtccaaccc ggaaaagcac    480
ggtaaaacgc cactggcagc agccattggt aactgggagt tcgcagagga tttgtttagc    540
taaacacgcg gttgctcttg aagtgtgcgc caaagtccgg ctacactgga aggacagatt    600
tggttgctgt gctctgcgaa agccagttac cacggttaag cagttcccca actgacttaa    660
ccttcgatca aaccacctcc ccaggtggtt ttttcgttta cagggcaaaa gattacgcgc    720
agaaaaaaag gatctcaaga agatcctttg atcacctgcc tctaaaaact tttattacgc    780
cccgccctgc cactcatcgc agtactgttg taattcatta agcattctgc cgacatggaa    840
gccatcacag acggcatgat gaacctgaat cgccagcggc atcagcacct tgtcgccttg    900
cgtataatat ttgcccatag tgaaaacggg ggcgaagaag ttgtccatat tggccacgtt    960
taaatcaaaa ctggtgaaac tcacccaggg attggctgag acgaaaaaca tattctcaat   1020
aaacccttta gggaaatagg ccaggttttc accgtaacac gccacatctt gcgaatatat   1080
gtgtagaaac tgccggaaat cgtcgtggta ttcactccag agcgatgaaa acgtttcagt   1140
ttgctcatgg aaaacggtgt aacaagggtg aacactatcc catatcacca gctcaccgtc   1200
tttcattgcc atacgaaact ccggatgagc attcatcagg cgggcaagaa tgtgaataaa   1260
ggccggataa aacttgtgct tatttttctt tacggtcttt aaaaaggccg taatatccag   1320
ctgaacggtc tggttatagg tacattgagc aactgactga atgcctcaa  atgttctttt   1380 acgatgccat tgggatatat caacggtggt atatccagtg atttttttct ccatcatatt   1440 cttcctttttt caatattatt gaagcattta tcagggttat tgtctcatga gcggatacat   1500
atttgaatgt atttagaaaa ataaacaaat agggtcagt gttacaacca attaccaat    1560 tctgatctcc tgttagtgag ggttaatgcc cggaacgaag aaaggcccac ccgtgaaggt   1620
gagccagtga gttggttaca ttttctcttg agggtttagc ttttcagacg acgccaaaag   1680
gtcgtacgtg aaatacccaa atagttggcc gcagccgtct tgtcaccatt aaacttctca   1740
```

```
agcgcttgct gcggggtcag caaacgcgga gccggcgtct ttgcgctctc acgcgccagc    1800
tccggcagca gcaactgcat gaattgcgga gtcagatccg gggtcggctc aacggacagg    1860
aacagcgcca ggcgttccat catattacgc agctcgcgga tgttacccgg ccagtcataa    1920
tgcagcagca ccgtttcgct cgcctgcaga ccctggcgca gtccgcagag aacggtgcg     1980 ctcagggctg ccagcgagac tttcaggaaa gactccgcca gcggtaaaat gtcggcgaca    2040
cgttcacgca acggcgggag ctgcagacgc agaatgctca ggcggtagaa caggtcgcga    2100
cgaaaacggc cctgttgcat atcctcttcc agattgcagt gggtcgcgct aatcacgcgc    2160
acgtctaccg gaaccggttg atgaccaccg acgcgggtca cttctttctc ttccagcaca    2220
cgcagcagac gggtttgcaa tggcagcggc atctcaccga tctcgtccag gaacaaggtg    2280
ccgccgtggg caatttcaaa caaccagca cggccaccgc gacggctacc cgtgaatgcg      2340
ccctcttcgt agccaaacag ctcagcttcc agcaggcttt ccgcgattgc accgcaatta    2400
actgccacaa acggatgaga tttcttaccc tggcgggcat cgtgacgggc gaaatactca    2460
cgatggattg cttgcgcagc cagttcctta cccgtaccag tctcgccttc gatcagaaca    2520
gccgcgctgc tacgtgcata cagcagaatg gtctggcgaa cttgctccat ttgagggctt    2580
tggcccagca tatcacccag gacataacgg gtacgcagcg cattacgcgt cgcatcgtgg    2640
gtgttgtggc gcaggctcat tctggtcatg tccagggcgt cgctgaacgc ctgacgcacc    2700
gttgccgcgc tgtagataaa gatgcccgtc atgcccgctt cttcggccaa gtccgtgatc    2760
agacccgcac caaccacagc ctcggtaccg ttcgctttca gttcgttgat ctggccacgt    2820
gcatcttcct cggtaatgta gctgcgttgg tccaggcgca gattaaaggt cttttgaaac    2880
gcgaccagcg cagggatcgt ttcctggtag gtgacaacgc caatcgagga ggtcagtttg    2940
cctgccttcg ccagcgcctg caagacatcg taaccgctcg gcttaatcag gatcaccggc    3000
acggacagac gggatttcag gtaggcacca ttgctacccg ctgcgataat ggcgtcacaa    3060
cgctcgttgg ccagcttttt gcgaatgtag gtaacggctt tctcgaaacc cagctgaatc    3120
ggagtgatgt tcgccaggtg atcaaactcc aggctaatgt cgcggaacaa ctcgaacaga    3180
cgggtgacgc taacgtgtcca aataactggt ttatcatcgt tcaaacgcgg tgggtgtgcc    3240
atggtgaata cctcctgtta agaaaccgaa tattgggttt aaacttgttt cataattgtt    3300
gcaatgaaac gcggtgaaac attgcctgaa acgttaactg aaacgcatat ttgcggatta    3360
gttcatgact ttatctctaa caaattgaaa ttaaacattt aattttatta aggcaattgt    3420
ggcacacccc ttgctttgtc tttatcaacg caaataacaa gttgataaca aaagcttagg    3480
aggaaaacat agagaccggt ctctctcgag taactagttg atagagatca agccttaacg    3540
aactaagacc cccgcaccga aaggtccggg ggttttttttt gaccttaaaa acataaccga    3600
ggagcagaca                                                           3610
```

<210> SEQ ID NO 6
<211> LENGTH: 3255
<212> TYPE: DNA
<213> ORGANISM: Artificial Sequence
<220> FEATURE:
<223> OTHER INFORMATION: Expression vector pBAD240

<400> SEQUENCE: 6

```
ggcctttctt cggtagaaac cccgagagca ggtatcaaag gatcttcttg agatcctttt      60
tttctgcgcg taatctgctg cttgcaaaca aaaaaaccac cgctaccagc ggtggtttgt     120
ttgccggatc aagagctacc aactcttttt ccgaggtaac tggcttcagc agagcgcaga    180
```

```
taccaaatac tgttcttcta gtgtagccgt agttaggcca ccacttcaag aactctgtag    240
caccgcctac atacctcgct ctgctaatcc tgttaccagt ggctgctgcc agtggcgata    300
agtcgtgtct taccggggttg gactcaagac gatagttacc ggataaggcg cagcggtcgg    360
gctgaacggg gggttcgtgc acacagccca gcttggagcg aacgacctac accgaactga    420
gatacctaca gcgtgagcta tgagaaagcg ccacgcttcc cgaagggaga aaggcggaca    480
ggtatccggt aagcggcagg gtcggaacag gagagcgcac gagggagctt ccaggggggaa    540 acgcctggta tctttatagt cctgtcgggt ttcgccacct ctgacttgag catcgatttt    600
tgtgatgctc gtcaggggg cggagcctat ggaaaaacgc cagcaacgca gaaaggccca    660
cccgaaggtg agccaggtga ttacatttgg gccctcatca gaggttttca ccgtcatcac    720
cgaaacgcgc gaggcagctg cggtaaagct catcagcgtg gtcgtgaagc gattcacaga    780
tgtctgcctg ttcatccgcg tccagctcgt tgagtttctc cagaagcgtt aatgtctggc    840
ttctgataaa gcgggccatg ttaagggcgg ttttttcctg tttggtcata cctgcttaga    900
aaaactcatc gagcatcaag tgaaactgca atttattcat atcaggatta tcaataccat    960 attttgaaa aagccgtttc tgtaatgaag gagaaaactc accgaggcag ttccatagga   1020
tggcaagatc ctggtatcgg tctgcgattc cgactcgtcc aacatcaata caacctatta   1080
atttcccctc gtcaaaaata aggttatcaa gtgagaaatc accatgagtg acgactgaat   1140
ccggtgagaa tggcaaaagc ttatgcattt cttttccagac ttgttcaaca ggccagccat   1200
tacgctcgtc atcaaaatca ctcgcaccaa ccaaaccgtt attcattcgt gattgcgcct   1260
gagcgagacg aaatacgcga tcgccgttaa aaggacaatt acaaacagga tcgaatgca   1320 accggcgcag gaacactgcc agcgcatcaa caatattttc acctgaatca ggatattctt   1380
ctaatacctg gaatgctgtt ttccctggga tcgcagtggt gagtaaccat gcatcatcag   1440
gagtacggat aaaatgcttg atggtcggaa gaggcataaa ttccgtcagc cagtttagcc   1500
tgaccatctc atctgtaaca tcattggcaa cgctaccttt gccatgtttc agaaacaact   1560
ctggcgcatc gggcttccca tacaatcgat agattgtcgc acctgattgc ccgacattat   1620
cgcgagccca tttatacccca tataaatcag catccatgtt ggaatttaat cgcggcctcg   1680
agcaagacgt ttcccgttga atatggctca tagctcctga aaatctcgat aactcaaaaa   1740 atacgcccg tagtgatctt atttcattat ggtgaaagtt ggaacctctt acgtgccgat   1800
caagtcaaaa gcctccgcgg gagagtgttc accgacaaac aacagataaa acaaaaggcc   1860
cagtcttccg actgagccctt tgttttatt tgatgtctgg cagttcccga gacgttatga   1920
caacttgacg gctacatcat tcacttttc ttcacaaccg gcacggaact cgctcgggct   1980
ggccccggtg cattttttaa atacccgcga gaaatagagt tgatcgtcaa accaacatt   2040 gcgaccgacg gtggcgatag gcatccgggt ggtgctcaaa agcagcttcg cctggctgat   2100
acgttggtcc tcgcgccagc ttaagacgct aatccctaac tgctggcgga aaagatgtga   2160
cagacgcgac ggcgacaagc aaacatgctg tgcgacgctg gcgatatcaa aattgctgtc   2220
tgccaggtga tcgctgatgt actgacaagc ctcgcgtacc cgattatcca tcggtggatg   2280
gagcgactcg ttaatcgctt ccatgcgccg cagtaacaat tgctcaagca gatttatcgc   2340
cagcagctcc gaatagcgcc cttccccttg cccggcgtta atgatttgcc caaacaggtc   2400
gctgaaatgc ggctggtgcg cttcatccgg gcgaaagaac cccgtattgg caaatattga   2460
cggccagtta agccattcat gccagtaggc gcgcggacga agtaaacccc actggtgata   2520
```

```
ccattcgcga gcctccggat gacgaccgta gtgatgaatc tctcctggcg ggaacagcaa    2580
aatatcaccc ggtcggcaaa caaattctcg tccctgattt ttcaccaccc cctgaccgcg    2640
aatggtgaga ttgagaatat aacctttcat tcccagcggt cggtcgataa aaaaatcgag    2700
ataaccgttg gcctcaatcg gcgttaaacc cgccaccaga tgggcattaa acgagtatcc    2760
cggcagcagg ggatcatttt gcgcttcagc catactttc atactcccgc cattcagaga    2820
agaaaccaat tgtccatatt gcatcagaca ttgccgtctc tgcgtctttt actggctctt    2880
ctcgctaacc aaaccggtaa ccccgcttat taaaagcatt ctgtaacaaa gcgggaccaa    2940
agccatgaca aaaacgcgta acaaaagtgt ctataatcac ggcagaaaag tccacattga    3000
ttatttgcac ggcgtcacac tttgctatgc catagcattt ttatccataa gattagcgga    3060
tcctacctga cgctttttat cgcaactctc tactgtttct ccatacccgt ttttttgggc    3120
tagcaggagg taaaaaaaat gtgagaccgg tctcggtcta gataactagt tgatcggtca    3180
gtttcacctg atttacgtaa aaacccgctt cggcgggttt ttgcttttgg aggggcagaa    3240
agatgaatga ctgtc                                                     3255

<210> SEQ ID NO 7
<211> LENGTH: 5802
<212> TYPE: DNA
<213> ORGANISM: Artificial Sequence
<220> FEATURE:
<223> OTHER INFORMATION: Expression vector pPRO44

<400> SEQUENCE: 7
atcgatttag cttttcagac gacgccaaaa ggtcgtacgt gaaataccca aatagttggc      60
cgcagccgtc ttgtcaccat taaacttctc aagcgcttgc tgcggggtca gcaaacgcgg     120
agccggcgta tttgcgctct cacgcgccag ctccggcagc agcaactgca tgaattgcgg     180
agtcagatcc ggggtcggct caacggacag gaacagcgcc aggcgttcca tcatattacg     240
cagctcgcgg atgttacccg gccagtcata atgcagcagc accgtttcgc tcgcctgcag     300
accctggcgc agtgccgcag agaacggtgc gctcagggct gccagcgaga cttttcaggaa    360 agactccgcc agcggtaaaa tgtcggcgac acgttcacgc aacggcggga gctgcagacg     420
cagaatgctc aggcggtaga acaggtcgcg acgaaaacgg ccctgttgca tatcctcttc     480
cagattgcag tgggtcgcgc taatcacgcg cacgtctacc ggaaccggtt gatgaccacc     540
gacgcgggtc acttctttct cttccagcac acgcagcaga cgggtttgca atggcagcgg     600
catctcaccg atctcgtcca ggaacaaggt gccgccgtgg gcaatttcaa acaaaccagc     660
acggccaccg cgacggctac ccgtgaatgc gccctcttcg tagccaaaca gctcagcttc     720
cagcaggctt tccgcgattg caccgcaatt aactgccaca aacggatgag atttcttacc     780
ctggcgggca tcgtgacggg cgaaatactc acgatggatt gcttgcgcag ccagttcctt     840
acccgtacca gtctcgcctt cgatcagaac agccgcgctg ctacgtgcat acagcagaat     900
ggtctggcga acttgctcca tttgagggct ttggcccagc atatcaccca ggacataacg     960
ggtacgcagc gcattacgcg tcgcatcgtg ggtgttgtgg cgcaggctca ttctggtcat    1020
gtccagggcg tcgctgaacg cctgacgcac cgttgccgcg ctgtagataa agatgcccgt    1080
catgcccgct tcttcggcca gtccgtgat cagacccgca ccaaccacag cctcggtacc     1140
gttcgctttc agtcgttga tctgccacg tgcatcttcc tcggtaatgt agctgcgttg     1200
gtccaggcgc agattaaagg tcttttgaaa cgcgaccagc gcaggatcg tttcctggta     1260 ggtgacaacg ccaatcgagg aggtcagttt gcctgccttc gccagcgcct gcaagacatc    1320
```

```
gtaaccgctc ggcttaatca ggatcaccgg cacggacaga cgggatttca ggtaggcacc    1380
attgctaccc gctgcgataa tggcgtcaca acgctcgttg gccagctttt tgcgaatgta    1440
ggtaacggct ttctcgaaac ccagctgaat cggagtgatg ttcgccaggt gatcaaactc    1500
caggctaatg tcgcgaaca actcgaacag acgggtgacg ctaacggtcc aaataactgg     1560
tttatcatcg ttcaaacgcg gtgggtgtgc catggtgaat acctcctgtt aagaaaccga    1620
atattgggtt taaacttgtt tcataattgt tgcaatgaaa cgcggtgaaa cattgcctga    1680
aacgttaact gaaacgcata tttgcggatt agttcatgac tttatctcta acaaattgaa    1740
attaaacatt taatttttatt aaggcaattg tggcacaccc cttgctttgt ctttatcaac   1800
gcaaataaca agttgataac aagctagcga attcgagctc ggtacccggg gatcctctag    1860
agtcgacctg caggcatgca agcttggctg ttttggcgga tgagagaaga ttttcagcct    1920
gatacagatt aaatcagaac gcagaagcgg tctgataaaa cagaatttgc ctggcggcag    1980
tagcgcggtg gtcccacctg accccatgcc gaactcagaa gtgaaagcgc gtagcgccga   2040
tggtagtgtg gggtctcccc atgcgagagt agggaactgc caggcatcaa ataaaacgaa    2100
aggctcagtc gaaagactgg gcctttcgtt ttatctgttg tttgtcggtg aacgctctcc    2160
tgagtaggac aaatccgccg ggagcggatt tgaacgttgc gaagcaacgg cccggagggt    2220
ggcgggcagg acgcccgcca taaactgcca ggcatcaaat taagcagaag gccatcctga    2280
cggatggcct ttttgcgttt ctacaaactc ttttgtttat ttttctaaat acattcaaat    2340
atgtatccgc tcatgagaca ataaccctga taaatgcttc aataatattg aaaaaggaag    2400
agtatgagta ttcaacattt ccgtgtcgcc cttattccct ttttttgcggc attttgcctt   2460
cctgtttttg ctcacccaga aacgctggtg aaagtaaaag atgctgaaga tcagttgggt    2520
gcagcaaact attaactggc gaactactta ctctagcttc ccggcaacaa ttaatagact    2580
ggatggaggc ggataaagtt gcaggaccac ttctgcgctc ggcccttccg gctggctggt    2640
ttattgctga taaatctgga gccggtgagc gtgggtctcg cggtatcatt gcagcactgg    2700
ggccagatgg taagcccctcc cgtatcgtag ttatctacac gacggggagt caggcaacta   2760
tggatgaacg aaatagacag atcgctgaga taggtgcctc actgattaag cattggtaac    2820
tgtcagacca agtttactca tatatacttt agattgattt acgcgccctg tagcggcgca    2880
ttaagcgcgg cgggtgtggt ggttacgcgc agcgtgaccg ctacacttgc cagcgcccta    2940
gcgcccgctc ctttcgcttt cttcccttcc tttctcgcca cgttcgccgg ctttccccgt    3000
caagctctaa atcgggggct ccctttaggg ttccgattta gtgctttacg gcacctcgac    3060
cccaaaaaac ttgatttggg tgatggttca cgtagtgggc catcgccctg atagacggtt    3120
tttcgccctt tgacgttgga gtccacgttc tttaatagtg gactcttgtt ccaaactgga    3180
acaacactca accctatctc gggctattct tttgatttat aagggatttt gccgatttcg    3240
gcctattggt taaaaaatga gctgatttaa caaaaattta cgcgaattt taacaaaata    3300
ttaacgttta caatttaaaa ggatctaggt gaagatcctt tttgataatc tcatgaccaa    3360
aatcccttaa cgtgagtttt cgttccactg agcgtcagac cccgtagaaa agatcaaagg    3420
atcttcttga gatccttttt ttctgcgcgt aatctgctgc ttgcaaacaa aaaaaccacc    3480
gctaccagcg gtggtttgtt tgccggatca agagctacca actcttttc cgaaggtaac    3540
tggcttcagc agagcgcaga taccaaatac tgtccttcta gtgtagccgt agttaggcca    3600
ccacttcaag aactctgtag caccgcctac atacctcgct ctgctaatcc tgttaccagt    3660
```

```
caggcatttg agaagcacac ggtcacactg cttccggtag tcaataaacc ggtaaaccag    3720
caatagacat aagcggctat ttaacgaccc tgccctgaac cgacgaccgg gtcgaatttg    3780
ctttcgaatt tctgccattc atccgcttat tatcacttat tcaggcgtag caaccaggcg    3840
tttaagggca ccaataactg ccttaaaaaa attacgcccc gccctgccac tcatcgcagt    3900
actgttgtaa ttcattaagc attctgccga catggaagcc atcacaaacg gcatgatgaa    3960
cctgaatcgc cagcggcatc agcaccttgt cgccttgcgt ataatatttg cccatggtga    4020 aaacggggc gaagaagttg tccatattgg ccacgtttaa atcaaaactg gtgaaactca    4080
cccagggatt ggctgagacg aaaaacatat tctcaataaa ccctttaggg aaataggcca    4140
ggttttcacc gtaacacgcc acatcttgcg aatatatgtg tagaaactgc cggaaatcgt    4200
cgtggtattc actccagagc gatgaaaacg tttcagtttg ctcatggaaa acggtgtaac    4260
aagggtgaac actatcccat atcaccagct caccgtcttt cattgccata cggaattccg    4320
gatgagcatt catcaggcgg gcaagaatgt gaataaaggc cggataaaac ttgtgcttat    4380
ttttctttac ggtcttttaaa aaggccgtaa tatccagctg aacggtctgg ttataggtac    4440
attgagcaac tgactgaaat gcctcaaaat gttctttacg atgccattgg gatatatcaa    4500
cggtggtata tccagtgatt ttttttctcca ttttagcttc cttagctcct gaaaatctcg    4560
ataactcaaa aaatacgccc ggtagtgatc ttatttcatt atggtgaaag ttggaacctc    4620
ttacgtgccg atcaacgtct catttttcgcc aaaagttggc ccaggcttc ccggtatcaa    4680 cagggacacc aggatttatt tattctgcga agtgatcttc cgtcacaggt atttattcgg    4740
cgcaaagtgc gtcgggtgat gctgccaact tactgattta gtgtatgatg gtgttttgta    4800
ggtgctccag tggcttctgt ttctatcagc tgtccctcct gttcagctac tgacggggtg    4860
gtgcgtaacg gcaaaagcac cgccggacat caactagtct tccgcttcct cgctcactga    4920
ctcgctacgc tcggtcgttc gactgcggcg agcggtgtca gctcactcaa aagcggtaat    4980
acggttatcc acagaatcag gggataaagc cggaaagaac atgtgagcaa aaagcaaagc    5040
accggaagaa gccaacgccg caggcgtttt tccataggct ccgccccct gacgagcatc    5100 acaaaaatcg acgctcaagc cagaggtggc gaaacccgac aggactataa agataccagg    5160
cgtttccccc tggaagctcc ctcgtgcgct ctcctgttcc gaccctgccg cttaccggat    5220
acctgtccgc ctttctccct cgggaagcg tggcgcttc tcatagctca cgctgttggt    5280
atctcagttc ggtgtaggtc gttcgctcca agctgggctg tgtgcacgaa ccccccgttc    5340
agcccgaccg ctgcgcctta tccggtaact atcgtcttga gtccaacccg gtaagacacg    5400
acttatcgcc actggcagca gccattggta actgatttag aggactttgt cttgaagtta    5460
tgcacctgtt aaggctaaac tgaaagaaca gatttggtg agtgcggtcc tccaacccac    5520
ttaccttggt tcaaagagtt ggtagctcag cgaaccttga gaaaaccacc gttggtagcg    5580 gtggttttc tttatttatg agatgatgaa tcaatcggtc tatcaagtca acgaacagct    5640
attccgttga cgtctatttg ctcatgagcc cgaagtggcg agcccgatct tccccatcgg    5700
tgatgtcggc gatataggcg ccagcaaccg cacctgtggc gccggtgatg ccggccacga    5760
tgcgtccggc gtagaggatc tgctcatgtt tgacagctta tc                       5802
```

<210> SEQ ID NO 8
<211> LENGTH: 5791
<212> TYPE: DNA
<213> ORGANISM: Artificial Sequence
<220> FEATURE:
<223> OTHER INFORMATION: Expression vector pPRO45

<400> SEQUENCE: 8

```
atcgatttag cttttcagac gacgccaaaa ggtcgtacgt gaaatacccaa aatagttggc      60
cgcagccgtc ttgtcaccat taaacttctc aagcgcttgc tgcggggtca gcaaacgcgg     120
agccggcgtc tttgcgctct cacgcgccag ctccggcagc agcaactgca tgaattgcgg     180
agtcagatcc ggggtcggct caacggacag gaacagcgcc aggcgttcca tcatattacg     240
cagctcgcgc atgttacccg gccagtcata atgcagcagc accgtttcgc tcgcctgcag     300
accctggcgc agtgccgcag agaacggtgc gctcagggct gccagcgaga ctttcaggaa     360
agactccgcc agcggtaaaa tgtcggcgac acgttcacgc aacggcggga gctgcagacg     420
cagaatgctc aggcggtaga acaggtcgcg acgaaaacgg ccctgttgca tatcctcttc     480
cagattgcag tgggtcgcgc taatcacgcg cacgtctacc ggaaccggtt gatgaccacc     540
gacgcgggtc acttctttct cttccagcac acgcagcaga cgggtttgca atggcagcgg     600
catctcaccg atctcgtcca ggaacaaggt gccgccgtgg gcaatttcaa acaaaccagc     660
acggccaccg cgacggctac ccgtgaatgc gccctcttcg tagccaaaca gctcagcttc     720
cagcaggctt tccgcgattg caccgcaatt aactgccaca aacggatgag atttcttacc     780
ctggcgggca tcgtgacggg cgaaatactc acgatggatt gcttgcgcag ccagttcctt     840
acccgtacca gtctcgcctt cgatcagaac agccgcgctg ctacgtgcat acagcagaat     900
ggtctggcga acttgctcca tttgagggct ttggcccagc atatcaccca ggacataacg     960
ggtacgcagc gcattacgcg tcgcatcgtg ggtgttgtgg cgcaggctca ttctggtcat    1020
gtccagggcg tcgctgaacg cctgacgcac cgttgccgcg ctgtagataa agatgcccgt    1080
catgcccgct tcttcggcca agtccgtgat cagacccgca ccaaccacag cctcggtacc    1140
gttcgctttc agtcgttga tctggccacg tgcatcttcc tcggtaatgt agctgcgttg     1200
gtccaggcgc agattaaagg tcttttgaaa cgcgaccagc gcaggatcg tttcctggta     1260
ggtgacaacg ccaatcgagg aggtcagttt gcctgccttc gccagcgcct gcaagacatc    1320
gtaaccgctc ggcttaatca ggatcaccgg cacggacaga cgggatttca ggtaggcacc    1380
attgctaccc gctgcgataa tggcgtcaca acgctcgttg gccagctttt tgcgaatgta    1440
ggtaacggct ttctcgaaac ccagctgaat cggagtgatg ttcgccaggt gatcaaactc    1500
caggctaatg tcgcggaaca actcgaacag acgggtgacg ctaacggtcc aaataactgg    1560
tttatcatcg ttcaaacgcg gtgggtgtgc catggtgaat acctcctgtt aagaaaccga    1620
atattgggtt taaacttgtt tcataattgt tgcaatgaaa cgcggtgaaa cattgcctga    1680
aacgttaact gaaacgcata tttgcggatt agttcatgac tttatctcta caaaattgaa    1740
attaaacatt taattttatt aaggcaattg tggcacaccc cttgctttgt ctttatcaac    1800
gcaaataaca agttgataac aagctagcga attcgagctc ggtacccggg gatcctctag    1860
agtcgacctg caggcatgca agcttggctg ttttggcgga tgagagaaga ttttcagcct    1920
gatacagatt aaatcagaac gcagaagcgg tctgataaaa cagaatttgc ctggcggcag    1980
tagcgcggtg gtcccacctg acccatgcc gaactcagaa gtgaaacgcc gtagcgccga    2040
tggtagtgtg gggtctcccc atgcgagagt agggaactgc caggcatcaa ataaaacgaa    2100
aggctcagtc gaaagactgg gcctttcgtt ttatctgttg tttgtcggtg aacgctctcc    2160
tgagtaggac aaatccgccg ggagcggatt tgaacgttgc gaagcaacgg cccgagggt    2220
ggcgggcagg acgcccgcca taaactgcca ggcatcaaat taagcagaag gccatcctga    2280
```

```
cggatggcct ttttgcgttt ctacaaactc ttttgtttat ttttctaaat acattcaaat   2340
atgtatccgc tcatgagaca ataaccctga taaatgcttc aataatattg aaaaaggaag   2400
agtatgagta ttcaacattt ccgtgtcgcc cttattccct ttttttgcggc attttgcctt   2460 cctgttttg ctcacccaga aacgctggtg aaagtaaaag atgctgaaga tcagttgggt    2520
gcagcaaact attaactggc gaactactta ctctagcttc ccggcaacaa ttaatagact   2580
ggatggaggc ggataaagtt gcaggaccac ttctgcgctc ggcccttccg gctggctggt   2640
ttattgctga taaatctgga gccggtgagc gtgggtctcg cggtatcatt gcagcactgg   2700
ggccagatgg taagccctcc cgtatcgtag ttatctacac gacggggagt caggcaacta   2760
tggatgaacg aaatagacag atcgctgaga taggtgcctc actgattaag cattggtaac   2820
tgtcagacca gtttactca tatatacttt agattgattt acgcgccctg tagcggcgca   2880
ttaagcgcgg cgggtgtggt ggttacgcgc agcgtgaccg ctacacttgc cagcgcccta   2940
gcgcccgctc ctttcgcttt cttcccttcc tttctcgcca cgttcgccgg ctttccccgt   3000
caagctctaa atcgggggct ccctttaggg ttccgattta gtgctttacg gcacctcgac   3060
cccaaaaaac ttgatttggg tgatggttca cgtagtgggc catcgccctg atagacggtt   3120
tttcgccctt tgacgttgga gtccacgttc tttaatagtg actcttgtt ccaaactgga    3180 acaacactca accctatctc gggctattct tttgatttat aagggatttt gccgatttcg   3240
gcctattggt taaaaatga gctgatttaa caaaaattta acgcgaattt taacaaaata    3300
ttaacgttta caatttaaaa ggatctaggt gaagatcctt tttgataatc tcatgaccaa   3360
aatcccttaa cgtgagtttt cgttccactg agcgtcagac cccgtagaaa agatcaaagg   3420
atcttcttga gatcctttt ttctgcgcgt aatctgctgc ttgcaaacaa aaaaaccacc    3480
gctaccagcg gtggtttgtt tgccggatca agagctacca actcttttc cgaaggtaac    3540 tggcttcagc agagcgcaga taccaaatac tgtccttcta gtgtagccgt agttaggcca   3600
ccacttcaag aactctgtag caccgcctac atacctcgct ctgctaatcc tgttaccagt   3660
caggcatttg agaagcacac ggtcacactg cttccggtag tcaataaacc ggtaaaccag   3720
caatagacat aagcggctat ttaacgaccc tgccctgaac cgacgaccgg gtcgaatttg   3780
ctttcgaatt tctgccattc atccgcttat tatcacttat tcaggcgtag caaccaggcg   3840
tttaagggca ccaataactg ccttaaaaaa attacgcccc gccctgccac tcatcgcagt   3900
actgttgtaa ttcattaagc attctgccga catggaagcc atcacaaacg gcatgatgaa   3960
cctgaatcgc cagcggcatc agcaccttgt cgccttgcgt ataatatttg cccatggtga   4020 aaacggggc gaagaagttg tccatattgg ccacgtttaa atcaaaactg gtgaaactca    4080
cccagggatt ggctgagacg aaaaacatat tctcaataaa ccctttaggg aaataggcca   4140
ggttttcacc gtaacacgcc acatcttgcg aatatatgtg tagaaactgc cggaaatcgt   4200
cgtggtattc actccagagc gatgaaaacg tttcagtttg ctcatggaaa acggtgtaac   4260
aagggtgaac actatcccat atcaccagct caccgtcttt cattgccata cggaattccg   4320
gatgagcatt catcaggcgg gcaagaatgt gaataaaggc cggataaaac ttgtgcttat   4380
ttttctttac ggtctttaaa aaggccgtaa tatccagctg aacggtctgg ttataggtac   4440
attgagcaac tgactgaaat gcctcaaaat gttctttacg atgccattgg gatatatcaa   4500
cggtggtata tccagtgatt tttttctcca ttttagcttc cttagctcct gaaaatctcg   4560
ataactcaaa aaatacgccc ggtagtgatc ttatttcatt atggtgaaag ttggaacctc   4620
ttacgtgccg atcaacgtct cattttcgcc aaaagttggc ccagggcttc ccggtatcaa   4680
```

```
cagggacacc aggatttatt tattctgcga agtgatcttc cgtcacaggt atttattcgg    4740
cgcaaagtgc gtcgggtgat gctgccaact tactgattta gtgtatgatg gtgttttga    4800 ggtgctccag tggcttctgt ttctatcagc tgtccctcct gttcagctac tgacggggtg    4860
gtgcgtaacg gcaaaagcac cgccggacat caactagtgc gctgcggaca catacaaagt    4920
tacccacaga ttccgtggat aagcagggga ctaacatgtg aggcaaaaca gcagggccgc    4980
gccggtggcg ttttccata  ggctccgccc tcctgccaga gttcacataa acagacgctt    5040
ttccggtgca tctgtgggag ccgtgaggct caaccatgaa tctgacagta cgggcgaaac    5100
ccgacaggac ttaaagatcc ccaccgtttc cggcgggtcg ctccctcttg cgctctcctg    5160
ttccgaccct gccgtttacc ggatacctgt tccgcctttc tcccttacgg aagtgtggc     5220 gctttctcat agctcacaca ctggtatctc ggctcggtgt aggtcgttcg ctccaagctg    5280
ggctgtaagc aagaactccc cgttcagccc gactgctgcg ccttatccgg taactgttca    5340
cttgagtcca acccggaaaa gcacggtaaa acgccactgg cagcagccat ggtaactgg     5400 gagttcgcag aggatttgtt tagctaaaca cgcggttgct cttgaagtgt gcgccaaagt    5460
ccggctacac tggaaggaca gatttggttg ctgtgctctg cgaaagccag ttaccacggt    5520
taagcagttc cccaactgac ttaaccttcg atcaaaccac ctccccaggt ggttttttcg    5580
tttacagggc aaaagattac gcgcagaaaa aaggatctc  aagaagatcc tttgatcgac    5640
gtctatttgc tcatgagccc gaagtggcga gcccgatctt ccccatcggt gatgtcggcg    5700
atataggcgc cagcaaccgc acctgtggcg ccggtgatgc cggccacgat gcgtccggcg    5760
tagaggatct gctcatgttt gacagcttat c                                   5791

<210> SEQ ID NO 9
<211> LENGTH: 25
<212> TYPE: DNA
<213> ORGANISM: Artificial Sequence
<220> FEATURE:
<223> OTHER INFORMATION: pPRO_REV_SpeI primer

<400> SEQUENCE: 9
gactgactag ttgatgtccg gcggt                                            25

<210> SEQ ID NO 10
<211> LENGTH: 28
<212> TYPE: DNA
<213> ORGANISM: Artificial Sequence
<220> FEATURE:
<223> OTHER INFORMATION: pPRO_FOR_AatII primer

<400> SEQUENCE: 10
tcagctgacg tctatttgct catgagcc                                         28

<210> SEQ ID NO 11
<211> LENGTH: 46
<212> TYPE: DNA
<213> ORGANISM: Artificial Sequence
<220> FEATURE:
<223> OTHER INFORMATION: RSF1030_FOR_SpeI primer

<400> SEQUENCE: 11
gcaaaagcac cgccggacat caactagtct tccgcttcct cgctca                     46

<210> SEQ ID NO 12
<211> LENGTH: 52
<212> TYPE: DNA
```

<213> ORGANISM: Artificial Sequence
<220> FEATURE:
<223> OTHER INFORMATION: RSF1030_REV_AatII primer

<400> SEQUENCE: 12

```
gccacttcgg gctcatgagc aaatagacgt caacggaata gctgttcgtt ga          52
```

<210> SEQ ID NO 13
<211> LENGTH: 46
<212> TYPE: DNA
<213> ORGANISM: Artificial Sequence
<220> FEATURE:
<223> OTHER INFORMATION: CloDF13_FOR_SpeI primer

<400> SEQUENCE: 13

```
gcaaaagcac cgccggacat caactagtgc gctgcggaca cataca              46
```

<210> SEQ ID NO 14
<211> LENGTH: 56
<212> TYPE: DNA
<213> ORGANISM: Artificial Sequence
<220> FEATURE:
<223> OTHER INFORMATION: CloDF13_REV_AatII primer

<400> SEQUENCE: 14

```
gccacttcgg gctcatgagc aaatagacgt cgatcaaagg atcttcttga gatcct      56
```

<210> SEQ ID NO 15
<211> LENGTH: 5304
<212> TYPE: DNA
<213> ORGANISM: Artificial Sequence
<220> FEATURE:
<223> OTHER INFORMATION: Dual-promoter vector, pSOL

<400> SEQUENCE: 15

```
ggcctttctt cggtagaagt cttccccag aggcaggtat caaaggatct tcttgagatc    60
cttttttct gcgcgtaatc tgctgcttgc aaacaaaaaa accaccgcta ccagcggtgg   120
tttgtttgcc ggatcaagag ctaccaactc ttttttccgag gtaactggct tcagcagagc   180
gcagatacca aatactgttc ttctagtgta gccgtagtta ggccaccact tcaagaactc   240
tgtagcaccg cctacatacc tcgctctgct aatcctgtta ccagtggctg ctgccagtgg   300
cgataagtcg tgtcttaccg ggttggactc aagacgatag ttaccggata aggcgcagcg   360
gtcgggctga acggggggtt cgtgcacaca gcccagcttg gagcgaacga cctacaccga   420
actgagatac ctacagcgtg agctatgaga aagcgccacg cttcccgaag ggagaaaggc   480
ggacaggtat ccggtaagcg gcagggtcgg aacaggagag cgcacgaggg agcttccagg   540
gggaaacgcc tggtatcttt atagtcctgt cgggtttcgc cacctctgac ttgagcatcg   600
attttttgtga tgctcgtcag ggggggcggag cctatggaaa aacgccagca acgcagaaag   660
gcccacccga aggtgagcca ggtgattaca tttgggccct catcagaggt tttcaccgtc   720
atcaccgaaa cgcgcgaggc agctgcggta agctcatca gcgtggtcgt gaagcgattc   780
acagatgtct gcctgttcat ccgcgtccag ctcgttgagt ttctccagaa gcgttaatgt   840
ctggcttctg ataaagcggg ccatgttaag gcggtttttt cctgtttgg tcatacctgc   900
ttagaaaaac tcatcgagca tcaaatgaaa ttgcaattta ttcatatcag gattatcaat   960
accatatttt tgaaaagcc gtttctgtaa tgaaggagaa aactcaccga ggcagttcca  1020
taggatggca agatcctggt atcggtctgc gattccgact cgtccaacat caatacaacc  1080
tattaattc cctcgtcaa aaataaggtt atcaagtgag aaatcaccat gagtgacgac  1140
```

| | |
|---|---|
| tgaatccggt gagaatggca aaagtttatg catttctttc cagacttgtt caacaggcca | 1200 |
| gccattacgc tcgtcatcaa aatcactcgc atcaaccaaa ccgttattca ttcgtgattg | 1260 |
| cgcctgagcg aggcgaaata cgcgatcgct gttaaaagga caattacaaa caggaatcga | 1320 |
| gtgcaaccgg cgcaggaaca ctgccagcgc atcaacaata ttttcacctg aatcaggata | 1380 |
| ttcttctaat acctggaacg ctgttttttcc ggggatcgca gtggtgagta accatgcatc | 1440 |
| atcaggagta cggataaaat gcttgatggt cggaagtggc ataaattccg tcagccagtt | 1500 |
| tagtctgacc atctcatctg taacatcatt ggcaacgcta cctttgccat gtttcagaaa | 1560 |
| caactctggc gcatcgggct tcccatacaa gcgatagatt gtcgcacctg attgcccgac | 1620 |
| attatcgcga gcccatttat acccatataa atcagcatcc atgttggaat taatcgcgg | 1680 |
| cctcgacgtt tcccgttgaa tatggctcat agctcctgaa atctcgata actcaaaaaa | 1740 |
| tacgcccggt agtgatctta tttcattatg gtgaaagttg gaacctctta cgtgccgatc | 1800 |
| aagaagacgg tcaaaagcct ccggtcggag gccgggagag tgttcaccga caacaacag | 1860 |
| ataaaacaaa aggcccagtc ttccgactga gccttttgtt ttatttgatg tctggcagtt | 1920 |
| cccgagacgt tatgacaact tgacggctac atcattcact ttttcttcac aaccggcacg | 1980 |
| gaactcgctc gggctggccc cggtgcattt tttaaatacc cgcgagaaat agagttgatc | 2040 |
| gtcaaaacca acattgcgac cgacggtggc gataggcatc cggtggtgc tcaaaagcag | 2100 |
| cttcgcctgg ctgatacgtt ggtcctcgcg ccagcttaag acgctaatcc ctaactgctg | 2160 |
| gcggaaaaga tgtgacagac gcgacggcga caagcaaaca tgctgtgcga cgctggcgat | 2220 |
| atcaaaattg ctgtctgcca ggtgatcgct gatgtactga caagcctcgc gtacccgatt | 2280 |
| atccatcggt ggatggagcg actcgttaat cgcttccatg cgccgcagta acaattgctc | 2340 |
| aagcagattt atcgccagca gctccgaata gcgcccttcc ccttgcccgg cgttaatgat | 2400 |
| ttgcccaaac aggtcgctga atgcggctg gtgcgcttca tccgggcgaa agaaccccgt | 2460 |
| attggcaaat attgacggcc agttaagcca ttcatgccag taggcgcgcg gacgaaagta | 2520 |
| aacccactgg tgataccatt cgcgagcctc cggatgacga ccgtagtgat gaatctctcc | 2580 |
| tggcgggaac agcaaaatat cacccggtcg gcaaacaaat tctcgtccct gattttttcac | 2640 |
| cacccctga ccgcgaatgg tgagattgag aatataacct ttcattccca gcggtcggtc | 2700 |
| gataaaaaa tcgagataac cgttggcctc aatcggcgtt aaacccgcca ccagatgggc | 2760 |
| attaaacgag tatcccggca gcagggatc attttgcgct tcagccatac ttttcatact | 2820 |
| cccgccattc agagaagaaa ccaattgtcc atattgcatc agacattgcc gtctctgcgt | 2880 |
| cttttactgg ctcttctcgc taaccaaacc ggtaaccccg cttattaaaa gcattctgta | 2940 |
| acaaagcggg accaaagcca tgacaaaaac gcgtaacaaa agtgtctata atcacggcag | 3000 |
| aaaagtccac attgattatt tgcacggcgt cacactttgc tatgccatag cattttttatc | 3060 |
| cataagatta gcggatccta cctgacgctt tttatcgcaa ctctctactg tttctccata | 3120 |
| cccgtttttt tgggctagca ggaggtaaaa aaaatgtgag accggtctcg gtctagatcg | 3180 |
| gtcagtttca cctgatttac gtaaaaaaccc gcttcggcgg ttttttgctt ttggagggc | 3240 |
| agaaagatga atgactgtct ctcctgttag tgagggttaa tgcccggaac gaagaaaggc | 3300 |
| ccacccgtga aggtgagcca gtgagttggt tacattttct cttgagggtt tagcttttca | 3360 |
| gacgacgcca aaaggtcgta cgtgaaatac ccaaatagtt ggccgcagcc gtcttgtcac | 3420 |
| cattaaactt ctcaagcgct tgctgcgggg tcagcaaacg cggagccggc gtctttgcgc | 3480 |

-continued

```
tctcacgcgc cagctccggc agcagcaact gcatgaattg cggagtcaga tccggggtcg   3540
gctcaacgga caggaacagc gccaggcgtt ccatcatatt acgcagctcg cggatgttac   3600
ccggccagtc ataatgcagc agcaccgttt cgctcgcctg cagaccctgg cgcagtgccg   3660
cagagaacgg tgcgctcagg gctgccagcg agactttcag gaaagactcc gccagcggta   3720
aaatgtcggc gacacgttca cgcaacggcg ggagctgcag acgcagaatg ctcaggcggt   3780
agaacaggtc gcgacgaaaa cggccctgtt gcatatcctc ttccagattg cagtgggtcg   3840
cgctaatcac gcgcacgtct accggaaccg gttgatgacc ccgacgcgg gtcacttctt   3900
tctcttccag cacacgcagc agacgggttt gcaatggcag cggcatctca ccgatctcgt   3960
ccaggaacaa ggtgccgccg tgggcaattt caaacaaacc agcacggcca ccgcgacggc   4020
tacccgtgaa tgcgccctct cgtagccaa acagctcagc ttccagcagg ctttccgcga   4080
ttgcaccgca attaactgcc acaaacggat gagatttctt accctggcgg gcatcgtgac   4140
gggcgaaata ctcacgatgg attgcttgcg cagccagttc cttacccgta ccagtctcgc   4200
cttcgatcag aacagccgcg ctgctacgtg catacagcag aatggtctgg cgaacttgct   4260
ccatttgagg gctttggccc agcatatcac ccaggacata cgggtacgc agcgcattac   4320
gcgtcgcatc gtgggtgttg tggcgcaggc tcattctggt catgtccagg gcgtcgctga   4380
acgcctgacg caccgttgcc gcgctgtaga taaagatgcc cgtcatgccc gcttcttcgg   4440
ccaagtccgt gatcagaccc gcaccaacca cagcctcggt accgttcgct ttcagttcgt   4500
tgatctggcc acgtgcatct tcctcggtaa tgtagctgcg ttggtccagg cgcagattaa   4560
aggtcttttg aaacgcgacc agcgcaggga tcgtttcctg gtaggtgaca acgccaatcg   4620
aggaggtcag tttgcctgcc ttcgccagcg cctgcaagac atcgtaaccg ctcggcttaa   4680
tcaggatcac cggcacggac agacgggatt tcaggtaggc accattgcta cccgctgcga   4740
taatggcgtc acaacgctcg ttggccagct ttttgcgaat gtaggtaacg gctttctcga   4800
aacccagctg aatcggagtg atgttcgcca ggtgatcaaa ctccaggcta atgtcgcgga   4860
acaactcgaa cagacgggtg acgctaacgg tccaaataac tggtttatca tcgttcaaac   4920
gcggtgggtg tgccatggtg aatacctcct gttaagaaac cgaatattgg gtttaaactt   4980
gtttcataat tgttgcaatg aaacgcggtg aaacattgcc tgaaacgtta actgaaacgc   5040
atatttgcgg attagttcat gactttatct ctaacaaatt gaaattaaac atttaatttt   5100
attaaggcaa ttgtggcaca ccccttgctt tgtctttatc aacgcaaata acaagttgat   5160
aacaaaagct taggaggaaa acatagagac cggtctctct cgagtaacta gttgatagag   5220
atcaagcctt aacgaactaa gaccccccgca ccgaaaggtc cgggggtttt ttttgacctt   5280
aaaaacataa ccgaggagca gaca                                          5304
```

<210> SEQ ID NO 16
<211> LENGTH: 451
<212> TYPE: PRT
<213> ORGANISM: Artificial Sequence
<220> FEATURE:
<223> OTHER INFORMATION: Infliximab chimeric (murine variable doman, human constant domain) heavy chain

<400> SEQUENCE: 16

Met Glu Val Lys Leu Glu Glu Ser Gly Gly Gly Leu Val Gln Pro Gly
1               5                   10                  15

Gly Ser Met Lys Leu Ser Cys Val Ala Ser Gly Phe Ile Phe Ser Asn
            20                  25                  30

His Trp Met Asn Trp Val Arg Gln Ser Pro Glu Lys Gly Leu Glu Trp
            35                  40                  45

Val Ala Glu Ile Arg Ser Lys Ser Ile Asn Ser Ala Thr His Tyr Ala
 50                  55                  60

Glu Ser Val Lys Gly Arg Phe Thr Ile Ser Arg Asp Asp Ser Lys Ser
 65                  70                  75                  80

Ala Val Tyr Leu Gln Met Thr Asp Leu Arg Thr Glu Asp Thr Gly Val
                 85                  90                  95

Tyr Tyr Cys Ser Arg Asn Tyr Tyr Gly Ser Thr Tyr Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys

<210> SEQ ID NO 17
<211> LENGTH: 215
<212> TYPE: PRT
<213> ORGANISM: Artificial Sequence
<220> FEATURE:
<223> OTHER INFORMATION: Infliximab chimeric (murine variable doman, human constant domain) light chain

<400> SEQUENCE: 17

```
Met Asp Ile Leu Leu Thr Gln Ser Pro Ala Ile Leu Ser Val Ser Pro
1               5                   10                  15

Gly Glu Arg Val Ser Phe Ser Cys Arg Ala Ser Gln Phe Val Gly Ser
            20                  25                  30

Ser Ile His Trp Tyr Gln Gln Arg Thr Asn Gly Ser Pro Arg Leu Leu
        35                  40                  45

Ile Lys Tyr Ala Ser Glu Ser Met Ser Gly Ile Pro Ser Arg Phe Ser
    50                  55                  60

Gly Ser Gly Ser Gly Thr Asp Phe Thr Leu Ser Ile Asn Thr Val Glu
65                  70                  75                  80

Ser Glu Asp Ile Ala Asp Tyr Tyr Cys Gln Gln Ser His Ser Trp Pro
                85                  90                  95

Phe Thr Phe Gly Ser Gly Thr Asn Leu Glu Val Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 18
<211> LENGTH: 4594
<212> TYPE: DNA
<213> ORGANISM: Artificial Sequence
<220> FEATURE:
<223> OTHER INFORMATION: pBAD240-Infliximab_HC expression construct

<400> SEQUENCE: 18

```
ggcctttctt cggtagaaac cccgagagca ggtatcaaag gatcttcttg agatcctttt      60
tttctgcgcg taatctgctg cttgcaaaca aaaaaaccac cgctaccagc ggtggtttgt     120
ttgccggatc aagagctacc aactcttttt ccgaggtaac tggcttcagc agagcgcaga     180
taccaaatac tgttcttcta gtgtagccgt agttaggcca ccacttcaag aactctgtag     240
caccgcctac atacctcgct ctgctaatcc tgttaccagt ggctgctgcc agtggcgata     300
agtcgtgtct taccgggttg gactcaagac gatagttacc ggataaggcg cagcggtcgg     360
gctgaacggg gggttcgtgc acacagccca gcttggagcg aacgacctac accgaactga     420
```

```
gatacctaca gcgtgagcta tgagaaagcg ccacgcttcc cgaagggaga aaggcggaca    480
ggtatccggt aagcggcagg gtcggaacag gagagcgcac gagggagctt ccaggggggaa   540
acgcctggta tctttatagt cctgtcgggt ttcgccacct ctgacttgag catcgatttt    600
tgtgatgctc gtcaggggggg cggagcctat ggaaaaacgc cagcaacgca gaaaggccca   660
cccgaaggtg agccaggtga ttacatttgg gccctcatca gaggttttca ccgtcatcac    720
cgaaacgcgc gaggcagctg cggtaaagct catcagcgtg gtcgtgaagc gattcacaga    780
tgtctgcctg ttcatccgcg tccagctcgt tgagtttctc cagaagcgtt aatgtctggc    840
ttctgataaa gcgggccatg ttaagggcgg ttttttcctg tttggtcata cctgcttaga    900
aaaactcatc gagcatcaag tgaaactgca atttattcat atcaggatta tcaataccat    960
attttgaaa aagccgtttc tgtaatgaag gagaaaactc accgaggcag ttccatagga   1020
tggcaagatc ctggtatcgg tctgcgattc cgactcgtcc aacatcaata caacctatta   1080
atttccctc gtcaaaaata aggttatcaa gtgagaaatc accatgagtg acgactgaat   1140
ccggtgagaa tggcaaaagc ttatgcattt ctttccagac ttgttcaaca ggccagccat   1200
tacgctcgtc atcaaaatca ctcgcaccaa ccaaaccgtt attcattcgt gattgcgcct   1260
gagcgagacg aaatacgcga tcgccgttaa aaggacaatt acaaacagga tcgaatgca   1320
accggcgcag gaacactgcc agcgcatcaa caatatttc acctgaatca ggatattctt   1380
ctaatacctg gaatgctgtt ttccctggga tcgcagtggt gagtaaccat gcatcatcag   1440
gagtacggat aaaatgcttg atggtcggaa gaggcataaa ttccgtcagc cagtttagcc   1500
tgaccatctc atctgtaaca tcattggcaa cgctacctt gccatgtttc agaaacaact   1560
ctggcgcatc gggcttccca tacaatcgat agattgtcgc acctgattgc ccgacattat   1620
cgcgagccca tttataccca tataaatcag catccatgtt ggaatttaat cgcggcctcg   1680
agcaagacgt ttcccgttga atatggctca tagctcctga aaatctcgat aactcaaaaa   1740
atacgcccgg tagtgatctt atttcattat ggtgaaagtt ggaacctctt acgtgccgat   1800
caagtcaaaa gcctccgcgg gagagtgttc accgacaaac aacagataaa acaaaaggcc   1860
cagtcttccg actgagcctt ttgttttatt tgatgtctgg cagttcccga gacgttatga   1920
caacttgacg gctacatcat tcacttttc ttcacaaccg gcacggaact cgctcgggct   1980
ggcccccggtg cattttttaa atacccgcga gaaatagagt tgatcgtcaa accaacatt   2040
gcgaccgacg gtggcgatag gcatccgggt ggtgctcaaa agcagcttcg cctggctgat   2100
acgttggtcc tcgcgccagc ttaagacgct aatccctaac tgctggcgga aaagatgtga   2160
cagacgcgac ggcgacaagc aaacatgctg tgcgacgctg gcgatatcaa aattgctgtc   2220
tgccaggtga tcgctgatgt actgacaagc ctcgcgtacc cgattatcca tcggtggatg   2280
gagcgactcg ttaatcgctt ccatgcgccg cagtaacaat tgctcaagca gatttatcgc   2340
cagcagctcc gaatagcgcc cttcccctttg cccggcgtta atgatttgcc caaacaggtc   2400
gctgaaatgc ggctggtgcg cttcatccgg gcgaaagaac cccgtattgg caaatattga   2460
cggccagtta agccattcat gccagtaggc gcgcggacga aagtaaaccc actggtgata   2520
ccattcgcga gcctccggat gacgaccgta gtgatgaatc tctcctggcg ggaacagcaa   2580
aatatcaccc ggtcggcaaa caaattctcg tccctgattt ttcaccaccc cctgaccgcg   2640
aatggtgaga ttgagaatat aacctttcat tcccagcggt cggtcgataa aaaaatcgag   2700
ataaccgttg gcctcaatcg gcgttaaacc cgccaccaga tggcattaa acgagtatcc   2760
cggcagcagg ggatcatttt gcgcttcagc catactttc atactccgc cattcagaga   2820
```

```
agaaaccaat tgtccatatt gcatcagaca ttgccgtctc tgcgtctttt actggctctt    2880
ctcgctaacc aaaccggtaa ccccgcttat taaaagcatt ctgtaacaaa gcgggaccaa    2940
agccatgaca aaaacgcgta acaaaagtgt ctataatcac ggcagaaaag tccacattga    3000
ttatttgcac ggcgtcacac tttgctatgc catagcattt ttatccataa gattagcgga    3060
tcctacctga cgcttttat cgcaactctc tactgtttct ccatacccgt ttttttgggc    3120
tagcaggagg taaaaaaat ggaagttaaa ttagaagaaa gcggcggcgg tttggtgcaa    3180
cctggcggtt cgatgaagtt gagctgcgtc gcaagcggtt tcattttttc caaccactgg    3240
atgaactggg tgcgccagtc tccggaaaag ggtctggaat gggttgcgga gatccgtagc    3300
aagagcatca atagcgcgac gcattatgcc gagagcgtca aaggccgctt caccatttct    3360
cgtgacgaca gcaaaagcgc tgtgtatctg caaatgaccg acttgcgtac cgaggacacg    3420
ggcgtgtatt actgctcccg caactattac ggttccacct acgactactg gggccagggt    3480
acgaccctga ccgttagctc ggcgagcacc aagggtccga gcgtctttcc gctggcaccg    3540
agcagcaaaa gcaccagcgg tggtaccgcc gcactgggtt gcctggtgaa agattacttc    3600
ccggaaccgg ttactgtgag ctggaacagc ggcgcgctga cctctggcgt gcacacgttc    3660
ccggcagttc tgcaaagcag cggcctgtac tccctgtcca gcgtcgtcac cgtgccgagc    3720
agcagcctgg gtacgcaaac ctatatttgt aacgtcaatc acaagccgag caacaccaaa    3780
gtggacaaaa aagtcgaacc gaaaagctgc gataaaaccc atacttgtcc gccgtgcccg    3840
gccccggagc ttctgggtgg tccaagcgtt tttctgttcc cgccgaagcc gaaagacacc    3900
ctgatgatca gccgcacccc tgaggtgacc tgtgtggtag ttgacgtttc ccacgaagat    3960
ccagaggtca gtttaactg gtatgtggat ggcgtcgaag ttcacaatgc aaagaccaag    4020
ccgcgtgaag aacagtataa ctctacgtac cgtgtcgtga gcgttctgac tgttctgcac    4080
caggattggc tgaacggcaa agagtacaag tgcaaggtta gcaataaagc gctgccggct    4140
ccgatcgaga aaaccatttc taaggctaaa ggtcagccgc gtgagccgca agtttacacc    4200
ctgccaccga gccgtgatga gctgacgaaa aatcaagtat ctctgacctg tctggtcaaa    4260 ggttttacc aagcgatat cgcggttgaa tgggagagca cggcagcc ggagaataat    4320 tacaagacga cgcctccggt gctggatagc gatggttcgt ttttcctgta cagcaagttg    4380
acggttgata aagccgttg gcaacagggt aacgtgttct cctgttccgt catgcatgaa    4440
gcgctgcaca accattatac tcagaaaagc ctcagcctgt ccccgggtaa ataagtctag    4500
ataactagtt gatcggtcag tttcacctga tttacgtaaa aacccgcttc ggcgggtttt    4560
tgcttttgga ggggcagaaa gatgaatgac tgtc                                 4594

<210> SEQ ID NO 19
<211> LENGTH: 4332
<212> TYPE: DNA
<213> ORGANISM: Artificial Sequence
<220> FEATURE:
<223> OTHER INFORMATION: pPRO430-Infliximab_LC expression construct

<400> SEQUENCE: 19
ccccagaggc aggtctagcg gagtgtatac tggcttacta tgttggcact gatgagggtg      60
tcagtgaagt gcttcatgtg gcaggagaaa aaaggctgca ccggtgcgtc agcagaatat     120
gtgatacagg atatattccg cttcctcgct cactgactcg ctacgctcgg tcgttcgact     180
gcggcgagcg gaaatggctt acgaacgggg cggagatttc ctggaagatg ccaggaagat     240
```

```
acttaacagg gaagtgagag ggccgcggca aagccgtttt tccataggct ccgcccccct    300
gacaagcatc acgaaatctg acgctcaaat cagtggtggc gaaacccgac aggactataa    360
agataccagg cgtttccccc tggcggctcc ctcgtgcgct ctcctgttcc tgcctttcgg    420
tttaccggtg tcattccgct gttataggcc gctttgtctc attccacgcc tgacactcag    480
ttccgggtag gcagttcgct ccaagctgga ctgtatgcac gaaccccccg ttcagtccga    540
ccgctgcgcc ttatccggta actatcgtct tgagtccaac ccggaaagac atgcaaaagc    600
accactggca gcagccactg gtaattgatt tagaggagtt agtcttgaag tcatgcgccg    660
gttaaggcta aactgaaagg acaagttttg gtgactgcgc tcctccaagc cagttacctc    720
ggttcaaaga gttggtagct cagagaacct tcgaaaaacc gccctgcaag gcggtttttt    780
cgttttcaga gcaagagatt acgcgcagac caaaacgatc tcaagaagat catcttatta    840
aacctgcctc taaaaacttt tattacgccc cgccctgcca ctcatcgcag tactgttgta    900
attcattaag cattctgccg acatggaagc catcacagac ggcatgatga acctgaatcg    960
ccagcggcat cagcaccttg tcgccttgcg tataatattt gcccatagtg aaaacggggg   1020
cgaagaagtt gtccatattg ccacgtttta atcaaaact ggtgaaactc acccagggat   1080
tggctgagac gaaaaacata ttctcaataa acccttttagg gaaataggcc aggttttcac   1140
cgtaacacgc cacatcttgc gaatatatgt gtagaaactg ccggaaatcg tcgtggtatt   1200
cactccagag cgatgaaaac gtttcagttt gctcatggaa aacggtgtaa caagggtgaa   1260
cactatccca tatcaccagc tcaccgtctt tcattgccat acggaactcc ggatgagcat   1320
tcatcaggcg gcaagaatg tgaataaagg ccggataaaa cttgtgctta tttttctttta   1380
cggtctttaa aaaggccgta atatccagct gaacggtctg gttataggta cattgagcaa   1440
ctgactgaaa tgcctcaaaa tgttctttac gatgccattg ggatatatca acggtggtat   1500
atccagtgat ttttttctcc atcatattct tccttttttca atattattga agcatttatc   1560
agggttattg tctcatgagc ggatacatat ttgaatgtat ttagaaaaat aaacaaatag   1620
gggtcagtgt tacaaccaat taaccaattc tgatctcctg ttagtgaggg ttaatgcccg   1680
gaacgaagaa aggcccaccc gtgaaggtga gccagtgagt tggttacatt ttctcttgag   1740
ggtttagctt ttcagacgac gccaaaaggt cgtacgtgaa atacccaaat agttggccgc   1800
agccgtcttg tcaccattaa acttctcaag cgcttgctgc ggggtcagca aacgcggagc   1860
cggcgtcttt gcgctctcac gcgccagctc cggcagcagc aactgcatga attgcggagt   1920
cagatccggg gtcggctcaa cggacaggaa cagcgccagg cgttccatca tattacgcag   1980
ctcgcggatg ttacccggcc agtcataatg cagcagcacc gtttcgctcg cctgcagacc   2040
ctggcgcagt gccgcagaga acggtgcgct cagggctgcc agcgagactt tcaggaagaa   2100
ctccgccagc ggtaaaatgt cggcgacacg ttcacgcaac ggcgggagct gcagacgcag   2160
aatgctcagg cggtagaaca ggtcgcgacg aaaacggccc tgttgcatat cctcttccag   2220
attgcagtgg gtcgcgctaa tcacgcgcac gtctaccgga accggttgat gaccaccgac   2280
gcgggtcact tctttctctt ccagcacacg cagcagacgg gtttgcaatg gcagcggcat   2340
ctcaccgatc tcgtccagga acaaggtgcc gccgtgggca atttcaaaca aaccagcacg   2400
gccaccgcga cggctacccg tgaatgcgcc ctcttcgtag ccaaacagct cagcttccag   2460
caggcttttcc gcgattgcac cgcaattaac tgccacaaac ggatgagatt tcttaccctg   2520
gcgggcatct gacgggcga aatactcacg atggattgct tgcgcagcca gttccttacc   2580
cgtaccagtc tcgccttcga tcagaacagc cgcgctgcta cgtgcataca gcagaatggt   2640
```

```
ctggcgaact tgctccattt gagggctttg gcccagcata tcacccagga cataacgggt    2700
acgcagcgca ttacgcgtcg catcgtgggt gttgtggcgc aggctcattc tggtcatgtc    2760
cagggcgtcg ctgaacgcct gacgcaccgt tgccgcgctg tagataaaga tgcccgtcat    2820
gcccgcttct tcggccaagt ccgtgatcag acccgcacca accacagcct cggtaccgtt    2880
cgctttcagt tcgttgatct ggccacgtgc atcttcctcg gtaatgtagc tgcgttggtc    2940
caggcgcaga ttaaaggtct tttgaaacgc gaccagcgca gggatcgttt cctggtaggt    3000
gacaacgcca atcgaggagg tcagtttgcc tgccttcgcc agcgcctgca agacatcgta    3060
accgctcggc ttaatcagga tcaccggcac ggacagacgg gatttcaggt aggcaccatt    3120
gctacccgct gcgataatgg cgtcacaacg ctcgttggcc agcttttgc gaatgtaggt    3180 aacggctttc tcgaaaccca gctgaatcgg agtgatgttc gccaggtgat caaactccag    3240
gctaatgtcg cggaacaact cgaacagacg ggtgacgcta acggtccaaa taactggttt    3300
atcatcgttc aaacgcggtg ggtgtgccat ggtgaatacc tcctgttaag aaaccgaata    3360
ttgggtttaa acttgtttca taattgttgc aatgaaacgc ggtgaaacat tgcctgaaac    3420
gttaactgaa acgcatattt gcggattagt tcatgacttt atctctaaca aattgaaatt    3480
aaacatttaa ttttattaag gcaattgtgg cacccccctt gctttgtctt tatcaacgca    3540
aataacaagt tgataacaaa agcttaggag gaaaacatat ggatatttta ttgacccaaa    3600
gcccagccat tctgtctgtt tccccgggcg agcgtgtttc ttttagctgc cgtgcaagcc    3660
agttcgttgg ttcatcgatc cactggtacc aacagcgtac gaacggtagc ccgcgtctgc    3720
tgattaagta cgcgagcgaa agcatgagcg gtatcccgag ccgcttcagc ggtagcggca    3780
gcggcacgga cttcacgctg agcatcaata cggttgaaag cgaggacatc gcggactatt    3840
actgccagca gagccattct tggccgttta cctttggcag cggtaccaat ctggaagtta    3900
aacgcaccgt ggcagcgccg tccgttttca ttttttcctcc gtccgatgag caactgaaat    3960
cgggcacggc cagcgtcgtg tgtctgttga caacttcta cccgcgtgag gcgaaggtgc    4020
agtggaaagt ggacaacgcg ctgcaatccg gtaatagcca ggaaagcgtc accgaacaag    4080
atagcaagga cagcacctac agcctgagct ctactctgac cctgagcaag ctgattatg    4140 agaaacacaa ggtctatgca tgtgaggtga cccatcaggg tctgtccagc ccggtcacca    4200
aaagcttcaa tcgcggtgag tgctaactcg agtaactagt tgatagagat caagccttaa    4260
cgaactaaga ccccgcacc gaaaggtccg ggggttttt ttgaccttaa aaacataacc    4320
gaggagcaga ca                                                        4332
```

<210> SEQ ID NO 20
<211> LENGTH: 7288
<212> TYPE: DNA
<213> ORGANISM: Artificial Sequence
<220> FEATURE:
<223> OTHER INFORMATION: pSOL-Infliximab expression construct

<400> SEQUENCE: 20

```
agctcctgaa aatctcgata actcaaaaaa tacgcccggt agtgatctta tttcattatg      60
gtgaaagttg gaacctctta cgtgccgatc aagaagacgt tcaaaagcct ccggtcggag     120
gccgggagag tgttcaccga caaacaacag ataaaacaaa aggcccagtc ttccgactga     180 gcctttgtt ttatttgatg tctggcagtt cccgagacgt tatgcaacaa ctgacggctac     240 atcattcact ttttcttcac aaccggcacg gaactcgctc gggctggccc cggtgcattt     300
```

-continued

```
tttaaatacc cgcgagaaat agagttgatc gtcaaaacca acattgcgac cgacggtggc    360
gataggcatc cgggtggtgc tcaaaagcag cttcgcctgg ctgatacgtt ggtcctcgcg    420
ccagcttaag acgctaatcc ctaactgctg gcggaaaaga tgtgacagac gcgacggcga    480
caagcaaaca tgctgtgcga cgctggcgat atcaaaattg ctgtctgcca ggtgatcgct    540
gatgtactga caagcctcgc gtacccgatt atccatcggt ggatggagcg actcgttaat    600
cgcttccatg cgccgcagta acaattgctc aagcagattt atcgccagca gctccgaata    660
gcgcccttcc ccttgccggg cgttaatgat ttgcccaaac aggtcgctga aatgcggctg    720
gtgcgcttca tccgggcgaa agaacccgt attggcaaat attgacgcc agttaagcca    780
ttcatgccag taggcgcgcg gacgaaagta aacccactgg tgataccatt cgcgagcctc    840
cggatgacga ccgtagtgat gaatctctcc tggcgggaac agcaaaatat cacccggtcg    900
gcaaacaaat tctcgtccct gattttcac cacccctga ccgcgaatgg tgagattgag     960
aatataacct ttcattccca gcggtcggtc gataaaaaaa tcgagataac cgttggcctc   1020
aatcggcgtt aaacccgcca ccagatgggc attaaacgag tatcccggca gcaggggatc   1080
attttgcgct tcagccatac ttttcatact cccgccattc agagaagaaa ccaattgtcc   1140
atattgcatc agacattgcc gtctctgcgt cttttactgg ctcttctcgc taaccaaacc   1200
ggtaaccccg cttattaaaa gcattctgta acaaagcggg accaaagcca tgacaaaaac   1260
gcgtaacaaa agtgtctata atcacggcag aaaagtccac attgattatt gcacggcgt    1320
cacactttgc tatgccatag cattttatc cataagatta gcggatccta cctgacgctt   1380
tttatcgcaa ctctctactg tttctccata cccgttttt tgggctagca ggaggtaaaa    1440
aaaatggaag ttaaattaga agaaagcggc ggcggtttgg tgcaacctgg cggttcgatg   1500
aagttgagct gcgtcgcaag cggttttcatt tttccaacc actggatgaa ctgggtgcgc    1560
cagtctccgg aaaagggtct ggaatgggtt gcggagatcc gtagcaagag catcaatagc   1620
gcgacgcatt atgccgagag cgtcaaaggc cgcttcacca tttctcgtga cgacagcaaa   1680
agcgctgtgt atctgcaaat gaccgacttg cgtaccgagg acacgggcgt gtattactgc   1740
tcccgcaact attacggttc cacctacgac tactggggcc agggtacgac cctgaccgtt   1800
agctcggcga gcaccaaggg tccgagcgtc tttccgctgg caccgagcag caaaagcacc   1860
agcggtggta ccgccgcact gggttgcctg gtgaaagatt acttcccgga accggttact   1920
gtgagctgga acagcggcgc gctgacctct ggcgtgcaca cgttcccggc agttctgcaa   1980
agcagcggcc tgtactccct gtccagcgtc gtcaccgtgc cgagcagcag cctgggtacg   2040
caaacctata tttgtaacgt caatcacaag ccgagcaaca ccaaagtgga caaaaaagtc   2100
gaaccgaaaa gctgcgataa acccatact tgtccgccgt gcccggcccc ggagcttctg    2160
ggtggtccaa gcgttttcct gttcccgccg aagccgaaag acaccctgat gatcagccgc   2220
accctgaggt tgacctgtgt ggtagttgac gtttccacg aagatccaga ggtcaagttt    2280
aactggtatg tggatggcgt cgaagttcac aatgcaaaga ccaagccgcg tgaagaacag   2340
tataactcta cgtaccgtgt cgtgagcgtt ctgactgttc tgcaccagga ttggctgaac   2400
ggcaaagagt acaagtgcaa ggttagcaat aaagcgctgc cggctccgat cgagaaaacc   2460
atttctaagg ctaaaggtca gccgcgtgag ccgcaagttt acaccctgcc accgagccgt   2520
gatgagctga cgaaaaatca agtatctctg acctgtctgg tcaaaggttt tacccaagc    2580
gatatcgcgt tgaatgggga gagcaacggc cagccggaga taattacaa gacgacgcct    2640
ccggtgctgg atagcgatgg ttcgttttc ctgtacagca agttgacggt tgataaaagc    2700
```

```
cgttggcaac agggtaacgt gttctcctgt tccgtcatgc atgaagcgct gcacaaccat    2760
tatactcaga aaagcctcag cctgtccccg ggtaaataag tctagataac tagttgatcg    2820
gtcagtttca cctgatttac gtaaaaaccc gcttcggcgg ttttttgctt ttggaggggc    2880
agaaagatga atgactgtct ctcctgttag tgagggttaa tgcccggaac gaagaaaggc    2940
ccacccgtga aggtgagcca gtgagttggt tacattttct cttgagggtt tagcttttca    3000
gacgacgcca aaaggtcgta cgtgaaatac ccaaatagtt ggccgcagcc gtcttgtcac    3060
cattaaactt ctcaagcgct tgctgcgggg tcagcaaacg cggagccggc gtctttgcgc    3120
tctcacgcgc cagctccggc agcagcaact gcatgaattg cggagtcaga tccggggtcg    3180
gctcaacgga caggaacagc gccaggcgtt ccatcatatt acgcagctcg cggatgttac    3240
ccggccagtc ataatgcagc agcaccgttt cgctcgcctg cagaccctgg cgcagtgccg    3300
cagagaacgg tgcgctcagg gctgccagcg agactttcag gaaagactcc gccagcggta    3360
aaatgtcggc gacacgttca cgcaacgcgg ggagctgcag acgcagaatg ctcaggcggt    3420
agaacaggtc gcgacgaaaa cggccctgtt gcatatcctc ttccagattg cagtgggtcg    3480
cgctaatcac gcgcacgtct accggaaccg gttgatgacc accgacgcgg gtcacttctt    3540
tctcttccag cacacgcagc agacgggttt gcaatggcag cggcatctca ccgatctcgt    3600
ccaggaacaa ggtgccgccg tgggcaattt caaacaaacc agcacggcca ccgcgacggc    3660
tacccgtgaa tgcgccctct tcgtagccaa acagctcagc ttccagcagg ctttccgcga    3720
ttgcaccgca attaactgcc acaaacggat gagatttctt accctggcgg gcatcgtgac    3780
gggcgaaata ctcacgatgg attgcttgcg cagccagttc cttacccgta ccagtctcgc    3840
cttcgatcag aacagccgcg ctgctacgtg catacagcag aatggtctgg cgaacttgct    3900
ccatttgagg gctttggccc agcatatcac ccaggacata acgggtacgc agcgcattac    3960
gcgtcgcatc gtgggtgttg tggcgcaggc tcattctggt catgtccagg gcgtcgctga    4020
acgcctgacg caccgttgcc gcgctgtaga taaagatgcc cgtcatgccc gcttcttcgg    4080
ccaagtccgt gatcagaccc gcaccaacca cagcctcggt accgttcgct ttcagttcgt    4140
tgatctggcc acgtgcatct tcctcggtaa tgtagctgcg ttggtccagg cgcagattaa    4200
aggtcttttg aaacgcgacc agcgcaggga tcgtttcctg gtaggtgaca acgccaatcg    4260
aggaggtcag tttgcctgcc ttcgccagcg cctgcaagac atcgtaaccg ctcggcttaa    4320
tcaggatcac cggcacggac agacgggatt tcaggtaggc accattgcta cccgctgcga    4380
taatggcgtc acaacgctcg ttggccagct ttttgcgaat gtaggtaacg gctttctcga    4440
aacccagctg aatcggagtg atgttcgcca ggtgatcaaa ctccaggcta atgtcgcgga    4500
acaactcgaa cagacgggtg acgctaacgg tccaaataac tggtttatca tcgttcaaac    4560
gcggtgggtg tgccatggtg aatacctcct gttaagaaac cgaatattgg gtttaaactt    4620
gtttcataat tgttgcaatg aaacgcggtg aaacattgcc tgaaacgtta actgaaacgc    4680
atatttgcgg attagttcat gactttatct ctaacaaatt gaaattaaac atttaatttt    4740
attaaggcaa ttgtggcaca ccccttgctt tgtctttatc aacgcaaata acaagttgat    4800
aacaaaagct taggaggaaa acatatggat attttattga cccaaagccc agccattctg    4860
tctgtttccc cgggcgagcg tgtttctttt agctgccgtg caagccagtt cgttggttca    4920
tcgatccact ggtaccaaca gcgtacgaac ggtagcccgc gtctgctgat taagtacgcg    4980
agcgaaagca tgagcggtat cccgagccgc ttcagcggta gcggcagcgg cacggacttc    5040
```

```
acgctgagca tcaatacggt tgaaagcgag gacatcgcgg actattactg ccagcagagc      5100
cattcttggc cgtttacctt tggcagcggt accaatctgg aagttaaacg caccgtggca      5160
gcgccgtccg ttttcatttt tcctccgtcc gatgagcaac tgaaatcggg cacggccagc      5220
gtcgtgtgtc tgttgaacaa cttctacccg cgtgaggcga aggtgcagtg gaaagtggac      5280
aacgcgctgc aatccggtaa tagccaggaa agcgtcaccg aacaagatag caaggacagc      5340
acctacagcc tgagctctac tctgaccctg agcaaggctg attatgagaa acacaaggtc      5400
tatgcatgtg aggtgaccca tcagggtctg tccagcccgg tcaccaaaag cttcaatcgc      5460
ggtgagtgct aactcgagta actagttgat agagatcaag ccttaacgaa ctaagacccc      5520
cgcaccgaaa ggtccggggg ttttttttga ccttaaaaac ataaccgagg agcagacagg      5580
cctttcttcg gtagaagtct tcccccagag gcaggtatca aaggatcttc ttgagatcct      5640
ttttttctgc gcgtaatctg ctgcttgcaa acaaaaaaac caccgctacc agcggtggtt      5700
tgtttgccgg atcaagagct accaactctt tttccgaggt aactggcttc agcagagcgc      5760
agataccaaa tactgttctt ctagtgtagc cgtagttagg ccaccacttc aagaactctg      5820
tagcaccgcc tacatacctc gctctgctaa tcctgttacc agtggctgct gccagtggcg      5880
ataagtcgtg tcttaccggg ttggactcaa gacgatagtt accggataag cgcagcggt      5940 cgggctgaac ggggggttcg tgcacacagc ccagcttgga gcgaacgacc tacaccgaac      6000
tgagatacct acagcgtgag ctatgagaaa gcgccacgct tcccgaaggg agaaaggcgg      6060
acaggtatcc ggtaagcggc agggtcggaa caggagagcg cacgagggag cttccagggg      6120
gaaacgcctg gtatctttat agtcctgtcg ggtttcgcca cctctgactt gagcatcgat      6180
ttttgtgatg ctcgtcaggg gggcggagcc tatggaaaaa cgccagcaac gcagaaaggc      6240
ccacccgaag gtgagccagg tgattacatt tgggccctca tcagaggttt tcaccgtcat      6300
caccgaaacg cgcgaggcag ctgcggtaaa gctcatcagc gtggtcgtga agcgattcac      6360
agatgtctgc ctgttcatcc gcgtccagct cgttgagttt ctccagaagc gttaatgtct      6420
ggcttctgat aaagcgggcc atgttaaggg cggttttttc ctgtttggtc atacctgctt      6480
agaaaaactc atcgagcatc aaatgaaatt gcaatttatt catatcagga ttatcaatac      6540
catatttttg aaaaagccgt ttctgtaatg aaggagaaaa ctcaccgagg cagttccata      6600
ggatggcaag atcctggtat cggtctgcga ttccgactcg tccaacatca atacaaccta      6660
ttaatttccc ctcgtcaaaa ataaggttat caagtgagaa atcaccatga gtgacgactg      6720
aatccggtga gaatggcaaa agtttatgca tttctttcca gacttgttca acaggccagc      6780
cattacgctc gtcatcaaaa tcactcgcat caaccaaacc gttattcatt cgtgattgcg      6840
cctgagcgag gcgaaatacg cgatcgctgt taaaaggaca attacaaaca ggaatcgagt      6900
gcaaccggcg caggaacact gccagcgcat caacaatatt ttcacctgaa tcaggatatt      6960
cttctaatac ctggaacgct gtttttccgg ggatcgcagt ggtgagtaac catgcatcat      7020
caggagtacg gataaaatgc ttgatggtcg gaagtggcat aaattccgtc agccagttta      7080
gtctgaccat ctcatctgta acatcattgg caacgctacc tttgccatgt ttcagaaaca      7140
actctggcgc atcgggcttc ccatacaagc gatagattgt cgcacctgat tgcccgacat      7200
tatcgcgagc ccatttatac ccatataaat cagcatccat gttggaattt aatcgcggcc      7260
tcgacgtttc ccgttgaata tggctcat                                         7288
```